US011261255B2

(12) United States Patent
Jiang et al.

(10) Patent No.: US 11,261,255 B2
(45) Date of Patent: Mar. 1, 2022

(54) ANTI-EPIDERMAL GROWTH FACTOR RECEPTOR (EGFR) ANTIBODIES

(71) Applicant: Shanghai Henlius Biotech, Inc., Shanghai (CN)

(72) Inventors: Weidong Jiang, San Jose, CA (US); Pei-Hua Lin, Sunnyvale, CA (US)

(73) Assignee: Shanghai Henlius Biotech, Inc., Shanghai (CN)

( * ) Notice: Subject to any disclaimer, the term of this patent is extended or adjusted under 35 U.S.C. 154(b) by 196 days.

(21) Appl. No.: 16/784,166

(22) Filed: Feb. 6, 2020

(65) Prior Publication Data

US 2020/0223929 A1 Jul. 16, 2020

Related U.S. Application Data

(63) Continuation of application No. 15/315,371, filed as application No. PCT/US2015/033402 on May 29, 2015, now Pat. No. 10,584,171.

(60) Provisional application No. 62/005,887, filed on May 30, 2014.

(51) Int. Cl.
*C07K 16/28* (2006.01)
*A61K 47/68* (2017.01)
*A61K 39/395* (2006.01)
*G01N 33/574* (2006.01)
*A61K 39/00* (2006.01)

(52) U.S. Cl.
CPC .... *C07K 16/2863* (2013.01); *A61K 39/39591* (2013.01); *A61K 47/6803* (2017.08); *A61K 47/6849* (2017.08); *G01N 33/5748* (2013.01); *A61K 2039/505* (2013.01); *C07K 2317/24* (2013.01); *C07K 2317/31* (2013.01); *C07K 2317/41* (2013.01); *C07K 2317/565* (2013.01); *C07K 2317/71* (2013.01); *C07K 2317/73* (2013.01); *C07K 2317/732* (2013.01); *C07K 2317/92* (2013.01); *G01N 2333/71* (2013.01)

(58) Field of Classification Search
None
See application file for complete search history.

(56) References Cited

U.S. PATENT DOCUMENTS

| 4,179,337 | A | 12/1979 | Davis |
| 4,301,144 | A | 11/1981 | Iwashita |
| 4,485,045 | A | 11/1984 | Regen |
| 4,496,689 | A | 1/1985 | Mitra |
| 4,544,545 | A | 10/1985 | Ryan |
| 4,640,835 | A | 2/1987 | Shimizu |
| 4,670,417 | A | 6/1987 | Iwasaki |
| 4,676,980 | A | 6/1987 | Segal et al. |
| 4,791,192 | A | 12/1988 | Nakagawa |
| 4,816,567 | A | 3/1989 | Cabilly |
| 4,933,294 | A | 6/1990 | Waterfield |
| 4,994,560 | A | 2/1991 | Kruper, Jr. |
| 5,013,556 | A | 5/1991 | Woodle |
| 5,229,275 | A | 7/1993 | Goroff |
| 5,274,119 | A | 12/1993 | Frazier |
| 5,342,604 | A | 8/1994 | Wilson |
| 5,401,638 | A | 3/1995 | Carney |
| 5,428,130 | A | 6/1995 | Capon |
| 5,428,139 | A | 6/1995 | Kiefer |
| 5,435,990 | A | 7/1995 | Cheng |
| 5,489,425 | A | 2/1996 | Kruper, Jr. |
| 5,500,362 | A | 3/1996 | Robinson |
| 5,505,931 | A | 4/1996 | Pribish |
| 5,545,806 | A | 8/1996 | Lonberg |
| 5,545,807 | A | 8/1996 | Surani et al. |
| 5,565,332 | A | 10/1996 | Hoogenboom |
| 5,567,610 | A | 10/1996 | Borrebaeck |
| 5,569,825 | A | 10/1996 | Lonberg |
| 5,573,905 | A | 11/1996 | Lerner |
| 5,591,669 | A | 1/1997 | Krimpenfort |
| 5,591,828 | A | 1/1997 | Bosslet |
| 5,625,126 | A | 4/1997 | Lonberg |
| 5,633,425 | A | 5/1997 | Lonberg |
| 5,641,870 | A | 6/1997 | Rinderknecht |
| 5,652,361 | A | 7/1997 | Simon |
| 5,661,016 | A | 8/1997 | Lonberg |

(Continued)

FOREIGN PATENT DOCUMENTS

| EP | 0308936 A2 | 2/1989 |
| EP | 0308936 B1 | 3/1989 |

(Continued)

OTHER PUBLICATIONS

Baumann et al. (Jun. 2007, e-pub. May 14, 2007). "EGFR-Targeted Anti-Cancer Drugs in Radiotherapy: Preclinical Evaluation of Mechanisms," Radiother. Oncol. 83(2):238-248.

Boerner, P. et al. (Jul. 1, 1991). "Production of Antigen-Specific Human Monoclonal Antibodies From in Vitro—Primed Human Splenocytes," J. Immunol. 147(1):86-95.

(Continued)

*Primary Examiner* — Nelson B Moseley, II

(74) *Attorney, Agent, or Firm* — Morrison & Foerster LLP

(57) ABSTRACT

Provided are anti-epidermal growth factor receptor (EGFR) antibodies, aglycosylated CDR-H2 anti-EGFR antibodies, and antigen binding fragments thereof. Also provided are isolated nucleic acid molecules that encode the anti-EGFR antibodies or antigen binding fragments thereof, related expression vectors, and host cells. Provided are methods of making anti-epidermal growth factor receptor (EGFR) antibodies, aglycosylated CDR-H2 anti-EGFR antibodies, and antigen binding fragments thereof. Also provided are related pharmaceutical compositions and methods of their use to treat subjects.

14 Claims, 25 Drawing Sheets

Specification includes a Sequence Listing.

(56) References Cited

U.S. PATENT DOCUMENTS

| | | | |
|---|---|---|---|
| 5,696,239 | A | 12/1997 | Wilson |
| 5,714,631 | A | 2/1998 | Wilson |
| 5,756,065 | A | 5/1998 | Wilson |
| 5,808,003 | A | 9/1998 | Subramanian |
| 5,821,337 | A | 10/1998 | Carter |
| 6,013,605 | A | 1/2000 | Rees |
| 6,194,551 | B1 | 2/2001 | Idusogie |
| 6,946,292 | B2 | 9/2005 | Kanda |
| 7,332,581 | B2 | 2/2008 | Presta |
| 7,723,484 | B2 | 5/2010 | Beidler |
| 10,584,171 | B2 | 3/2020 | Jiang et al. |
| 2004/0093621 | A1 | 5/2004 | Shitara et al. |
| 2005/0054048 | A1 | 3/2005 | Grasso |
| 2005/0152894 | A1 | 7/2005 | Krummen |
| 2005/0249722 | A1 | 11/2005 | Beliard |
| 2005/0272916 | A1 | 12/2005 | Hanai |
| 2006/0134709 | A1 | 6/2006 | Stavenhagen |
| 2011/0117110 | A1 | 5/2011 | Akamatsu |
| 2012/0156217 | A1* | 6/2012 | Setiady ............ A61P 5/38 424/158.1 |
| 2015/0079088 | A1 | 3/2015 | Lowman |
| 2017/0218073 | A1 | 8/2017 | Jiang |

FOREIGN PATENT DOCUMENTS

| | | |
|---|---|---|
| EP | 0308936 A3 | 2/1990 |
| EP | 0404097 A2 | 12/1990 |
| EP | 0404097 A3 | 10/1991 |
| EP | 0404097 B1 | 9/1996 |
| JP | 2009515878 A | 4/2009 |
| JP | 2014500711 A | 1/2014 |
| WO | WO199100360 A1 | 1/1991 |
| WO | WO199105264 A1 | 4/1991 |
| WO | WO199200373 A1 | 1/1992 |
| WO | WO199308829 A1 | 5/1993 |
| WO | WO199311161 A1 | 6/1993 |
| WO | WO199411026 A2 | 5/1994 |
| WO | WO199411026 A3 | 8/1994 |
| WO | WO199704801 A1 | 2/1997 |
| WO | WO199717852 A1 | 5/1997 |
| WO | WO199728267 A1 | 8/1997 |
| WO | WO199845479 A1 | 10/1998 |
| WO | WO199856418 A1 | 12/1998 |
| WO | WO199951642 A1 | 10/1999 |
| WO | WO199954342 A1 | 10/1999 |
| WO | WO200042072 A2 | 7/2000 |
| WO | WO200061739 A1 | 10/2000 |
| WO | WO200042072 A3 | 11/2000 |
| WO | WO2003035835 A2 | 5/2003 |
| WO | WO2003055993 A1 | 7/2003 |
| WO | WO2003035835 A3 | 10/2003 |
| WO | WO2004065540 A2 | 8/2004 |
| WO | WO2005011735 A1 | 2/2005 |
| WO | WO2004065540 A3 | 3/2005 |
| WO | WO2005018572 A2 | 3/2005 |
| WO | WO2005027966 A2 | 3/2005 |
| WO | WO2005044859 A2 | 5/2005 |
| WO | WO2005044859 A3 | 8/2005 |
| WO | WO2005027966 A3 | 9/2005 |
| WO | WO2006009694 A2 | 1/2006 |
| WO | WO2005018572 A3 | 4/2006 |
| WO | WO2006009694 A3 | 10/2006 |
| WO | WO2006114700 A2 | 11/2006 |
| WO | WO2006116260 A2 | 11/2006 |
| WO | WO2006116260 A3 | 2/2007 |
| WO | WO2007031875 A2 | 3/2007 |
| WO | WO2006114700 A3 | 4/2007 |
| WO | WO2007058823 A2 | 5/2007 |
| WO | WO2007058823 A3 | 5/2007 |
| WO | WO2007058823 A4 | 5/2007 |
| WO | WO2007031875 A3 | 2/2008 |
| WO | WO2012058588 A2 | 5/2012 |
| WO | WO2012058588 A3 | 5/2012 |
| WO | WO2012130471 A1 | 10/2012 |
| WO | WO2013134743 A1 | 9/2013 |
| WO | WO2014138449 A1 | 9/2014 |

OTHER PUBLICATIONS

Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.

Brüggemann et al. (1993). "Designer Mice: The Production of Human Antibody Repertoires in Transgenic Animals," Year in Immuno. 7:33-40.

Burton, D.R. (1985). "Immunoglobulin G: Functional Sites," Molec. Immunol. 22(3):161-206.

Capel, P.J. et al. (Feb. 1994). "Heterogeneity of Human IgG Fc receptors," Immunomethods 4(1):25-34.

Caron, P.C. et al. (Oct. 1, 1992). "Engineering Humanized Dimeric Forms of IgG Are More Effective Antibodies," J. Exp Med. 176:1191-1195.

Chang, K.-H. et al. (Aug. 2012). "Affinity Maturation of an Epidermal Growth Factor Receptor Targeting Human Monoclonal Antibody ER414 by CDR Mutation," Immune Network 12(4):155-164.

Chari, R.V.J. (2008, e-pub. Aug. 18, 2007). "Targeted Cancer Therapy: Conferring Specificity to Cytotoxic Drugs," Acc. Chem. Res. 41(1):98-107.

Chothia, C. et al. (Aug. 20, 1987). "Canonical Structures for the Hypervariable Regions of Immunoglobulins," J. Mol. Biol. 196(4):901-917.

Chowdhury, P.S. (2008). "Engineering Hot Spots for Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

Clynes, R. et al. (Jan. 1998). "Fc Receptors are Required in Passive and Active Immunity to Melanoma," Proc. Natl. Acad. Sci. U.S.A. 95:652-656.

Cole, S.P.C. et al. (1985). "THE EBV-Hybridoma Technique and its Application to Human Lung Cancer," Monoclonal Antibodies and Cancer Therapy, Alan R. Liss, Inc., New York, New York, pp. 77-96.

Creighton, T.E. (1983). Proteins: Structure and Molecular Properties, W.H. Freeman & Co., San Francisco, pp. 79-86.

Cummings, R.D. (2009). "Chapter 45: Antibodies and Lectins in Glycan Analysis" in Essentials of Glycobiology. 2nd edition Cold Spring Harbor (NY): Cold Spring Harbor Laboratory Press, 9 pages.

Daëron, M. (1997). "Fc receptor biology," Ann. Rev. Immunol. 15:203-234.

De Haas, M. et al. (1995). "Fcγ Receptor of Phagocytes," J. Lab. Clin. Med. 126(4):330-341.

Di Nicolantonio, F. et al. (2008, e-pub. Nov. 10, 2008). "Wild-Type BRAF is Required for Response to Panitumumab or Cetuximab in Metastatic Colorectal Cancer," J. Clin. Oncol. 26:5705-5712, 10 pages.

Dolgin, E. (2009, e-pub. Aug. 24, 2009). "FDA Narrows Drug Label Usage," Nature 460:1069, 3 pages.

Ellison, G. et al. (2013, e-pub. Nov. 20, 2012). "EGFR Mutation Testing in Lung Cancer: A Review of Available Methods and Their Use for Analysis of Tumour Tissue and Cytology Samples," J. Clin. Pathol. 66(2):79-89.

Eppstein, D.A. et al. (Jun. 1985). "Biological Activity of Liposome-Encapsulated Murine Interferon γ is Mediated by a Cell Membrane Receptor," Proc. Natl. Acad. Sci. USA 82:3688-3692.

European Examination Report, dated Aug. 16, 2018, for European Patent Application No. 15800314.5, filed Dec. 29, 2016, 20 pages.

Evan, G.I. et al. (Dec. 1985). "Isolation of Monoclonal Antibodies Specific for Human c-myc Proto-Oncogene Product," Mol. Cell. Biol. 5(12):3610-3616.

Extended European Search Report, dated Jan. 27, 2020, for European Patent Application No. 19201262.3, 12 pages.

Extended European Search Report, dated Sep. 28, 2017, for European Patent Application No. 15800314.5, filed Dec. 29, 2016, 12 pages.

(56) References Cited

OTHER PUBLICATIONS

Fernandes, D. (2005). "Demonstrating Comparability of Antibody Glycosylation During Biomanufacturing," European Biopharmaceutical Review. pp. 106-110.
Field, J. et al. (May 1988). "Purification of a RAS-Responsive Adenylyl Cyclase Complex from *Saccharomyces cerevisiae* by Use of an Epitope Addition Method," Mol. Cell. Biol. 8(5):2159-2165.
Fishwild et al. "High-avidity human IgGK Monoclonal Antibodies from a Novel Strain of Minilocus Transgenic Mice," Nature Biotechnol. 14:845-851, (Jul. 1996).
Friedman, M. et al. (2008, e-pub. Jan. 4, 2008). "Directed Evolution to Low Nanomolar Affinity of a Tumor-Targeting Epidermal Growth Factor Receptor-Binding Affibody Molecule," J. Mol. Biol. 376:1388-1402.
Gabizon, A. et al. (Oct. 4, 1989). "Pharmacokinetics and Issue Distribution of Doxorubicin Encapsulated in Stable Liposomes With Long Circulation Times," J. National Cancer Inst. 81(19)1484-1488.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Gerdes, C. et al. (Mar. 1, 2013, e-pub. Dec. 3, 2012). "GA201 (RG7160): a Novel, Humanized, Glycoengineered Anti-EGFR Antibody With Enhanced ADCC and Superior In Vivo Efficacy Compared With Cetuximab," Clin. Cancer Res. 19(5):1126-1138.
Ghetie, V. et al. (2000). "Multiple Roles for the Major Histocompatibility Complex Class I-Related Receptor FcRn," Annu. Rev. Immunol. 18:739-766.
Goding, J.W. (1983). "Production of Monoclonal Antibodies," Chapter 3 in Monoclonal Antibodies: Principles and Practice, Academic Press:59-103.
Goodman, J.W. et al. (1994). "Immunoglobulin Proteins," Chapter 6 in Basic and Clinical Immunology, Eighth Edition, Appleton & Lange: Norwalk, Conneticut, pp. 66-79.
Griffiths, A.D. et al. (1993). "Human Anti-Self Antibodies With High Specificity From Phage Display Libraries," EMBO J. 12(2):725-734.
Gruber, M. et al. (1994). "Efficient Tumor Cell Lysis Mediated by a Bispecific Single Chain Antibody Expressed in *Escherichia coli*," J. Immunol. 152:5368-5374.
Guha, M. et al. (Jun. 21, 2013). "DISSECT Method Using PNA-LNA Clamp Improves Detection of EGFR T790m Mutation," PloS One 8(6):e67782, 5 pages.
Gupta, R. et al. (2009, e-pub. Nov. 7, 2008). "Evaluation of EGFR Abnormalities in Patients With Pulmonary Adenocarcinoma: The Need to Test Neoplasms With More Than One Method," Mod. Pathol. 22(1):128-133.
Guyer, R.L. et al. (Aug. 1976). "Immunoglobulin Binding by Mouse Intestinal Epithelial Cell Receptors," J. Immunol. 117(2):587-593.
Hollinger, P. et al. (Jul. 1993). "'Diabodies": Small Bivalent and Bispecific Antibody Fragments," Proc. Natl. Acad. Sci. Usa 90:6444-6448.
Hoogenboom, H.R. et al. (1992). "By-Passing Immunisation. Human Antibodies From Synthetic Repertoires of Germline VH Gene Segments Rearranged in Vitro," J. Mol. Biol. 227:381-388.
Hoogenboom, H.R. et al. (2001). "Overview of Antibody Phage-Display Technology and Its Applications," Chapter 1 in Methods in Molecular Biology, O'Brien et al., ed., Human Press, Totowa, New Jersey, 178:1-37.
Hopp, T.P. et al. (1988). "A Short Polypeptide Marker Sequence Useful for Recombinant Protein Identification and Purification," Bio/Technology 6:1204-1210.
Hwang, K.J. et al. (Jul. 1980). "Hepatic Uptake and Degradation of Unilamellar Sphingomyelin/Cholesterol Liposomes: A Kinetic Study." Proc. Natl. Acad. Sci. USA 77:4030-4034.
Idusogie, E.E. et al. (2000). "Mapping of the C1q Binding Site on Rituxan, a Chimeric Antibody With a Human IgG1 Fc," J. Imrmmol. 164:4178-4184.
Imai-Nishiya, Harue et al. "Double Knockdown of a1 ,6-Fucosyltransferase (FUTB) and GDP-Man Nose 4,6-Dehydratase (GMO) in Antibody-Producing Cells: A New Strategy for Generating Fully Non-Fucosylated Therapeutic Antibodies With Enhanced ADCC," BMC Biotechnology (Nov. 30, 2007); 7:84; 13 pages.
International Preliminary Report on Patentability, dated Dec. 6, 2016, for PCT Application No. PCT/US2015/033402, filed May 29, 2015, 8 pages.
International Search Report, dated Nov. 23, 2015, for PCT Application No. PCT/US2015/033402, filed May 29, 2015, 5 pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
Jalkanen, M. et al. (Dec. 1987). "Cell Surface Proteoglycan of Mouse Mammary Epithelial Cells is Shed by Cleavage of Its Matrix-Binding Ectodomain From Its Membrane-Associated Domain," J. Cell. Biol. 105(6):3087-3096.
Jalkanen, M. et al. (Sep. 1985). "Heparan Sulfate Proteoglycans From Mouse Mammary Epithelial Cells: Localization on the Cell Surface With a Monoclonal Antibody," J. Cell. Biol. 101:976-985.
Japanese Office Action, dated Apr. 2, 2019, for Japanese Patent Application No. 2016-571061, 3 pages.
Johnson, K.S. et al. (1993). "Human Antibody Engineering," Current Opinion in Structural Biology 3:564-571.
Jones, P.T. et al. (May 29, 1986). "Replacing the Complementarity-Determining Regions in a Human Antibody With Those From a Mouse," Nature 321:522-525.
Jung, S.T. et al. (Dec. 2011, e-pub. Mar. 21, 2011). "Bypassing Glycosylation: Engineering Aglycosylated Full-Length IgG Antibodies for Human Therapy," Curr. Op. Biotechnol. 22(6):858-867.
Kabat, E.A. et al. (1991). Sequences of Proteins of Immunological Interest, 5th Ed. Public Health Service, National Institutes of Health, Bethesda MD., Table of Contents, 21 pages.
Kabat, E.A. et al. (Oct. 10, 1977). "Unusual Distribution of Amino Acids in Complementarity-Determining (Hypervariable) Segments of Heavy and Light Chains of Immunoglobulins and Their Possible Roles in Specificity of Antibody-Combining Sites," J. Biol. Chem. 252(19):6609-6616.
Kanda, Y. et al. (2006, e-pub. Apr. 11, 2006). "Comparison of Cell Line for Stable Production of Fucose-Negative Antibodies with Enhanced ADCC," Biotechnol. Bioeng. 94(4):680-688.
Kanda, Y. et al. (Jun. 19, 2007, e-pub. May 6, 2007). "Establishment of a GDP-Mannose 4,6-Dehydratase (GMD) Knockout Host Cell Line: A New Strategy for Generating Completely Non-Fucosylated Recombinant Therapeutics," Journal of Biotechnology 130(3):300-310.
Kim, J-K. et al. (1994). "Localization of the Site of the Murine IgGI Molecule That is Involved in Binding to the Murine Intestinal Fc Receptor," Eur. J. Immunol. 24:2429-2434.
Kinet, J.V. (1991). "Fc Receptors," Annu. Rev. Immunol 9:457-492.
Kostelny, S.A. et al. (Mar. 1, 1992). "Formation of a Bispecific Antibody by the Use of Leucine Zippers," J. Immunol. 148(5):1547-1553.
Kozbor et al. (Dec. 1984). "A Human Hybrid Myeloma for Production of Human Monoclonal Antibodies," J. Immunol. 133(6):3001-3005.
Köhler, G. et al. (Aug. 7, 1975). "Continuous Cultures of Fused Cells Secreting Antibody of Predefined Specificity," Nature 256:495-197.
Leymarie, N. et al. (Apr. 3, 2012). "Effective Use of Mass Spectrometry for Glycan and Glycopeptide Structural Analysis," Anal. Chem. 84(7):3040-3048, 19 pages.
Li, S. et al. (Apr. 2005). "Structural Basis for Inhibition of the Epidermal Growth Factor Receptor by Cetuximab," Cancer Cell 7(4):301-311.
Lippow, S.M. et al. (Oct. 2007, e-pub. Sep. 23, 2007). "Computational Design of Antibody-Affinity Improvement Beyond in vivo Maturation," Nature Biotechnology 25(10):1171-1176.

(56) References Cited

OTHER PUBLICATIONS

Lonberg, N. et al. (Apr. 28, 1994). "Antigen-Specific Human Antibodies From Mice Comprising Four Distinct Genetic Modifications," Nature 368:856-859.
Lonberg, N. et al. (1995). "Human Antibodies From Transgenic Mice," Intern. Rev. Immunol. 13:65-93.
Lopez-Rios, F. et al. (2013, e-pub. Feb. 5, 2013). "Comparison of Molecular Testing Methods for the Detectior of EGFR Mutations in Formalin-Fixed Paraffin-Embedded Tissue Specimens of Non-Small Cell Lung Cancer," J. Clin. Pathol. 66(5):381-385.
Lutz-Freyermuth, C. et al. (Aug. 1990). "Quantitative Determination That One of Two Potential RNA-Binding Domains of the A Protein Component of the U1 Small Nuclear Ribonucleoprotein Complex Binds with High Affinity to Stem-Loop II of U1 RNA," Proc. Natl. Acad. Sci. USA 87:6393-6397.
MacCallum, R.M. et al. (1996). "Antibody-Antigen Interactions: Contact Analysis and Binding Site Topography," J. Mol. Biol. 262:732-745.
Marasco, W.A. et al. (Aug. 1993). "Design, intracellular Expression, and Activity of a Human Anti-Human Immunodeficiency Virus Type 1 gp120 Single-Chain Antibody," Proc. Natl. Acad. Sci. USA 90:7889-7893.
Mariuzza, R.A. et al. (1987). "The Structural Basis of Antigen-Antibody Recognition," Annu. Rev. Biophys. Biophys. Chem. 16:139-159.
Marks, J.D. et al. (1991). "By-Passing Immunization. Human Antibodies From V-Gene Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10: 779-783.
Martin, F.J. et al. (1982). "Irreversible Coupling of Immunoglobulin Fragments to Preformed Vesicles," J. Biol. Chem. 257(1):286-288.
Martin, G.A. el al. (Jan. 10, 1992). "GAP Domains Responsible for Ras P21-Dependent Inhibition of Muscarinic Atrial K+ Channel Currents," Science 255(5041):192-194.
McCafferty, J. et al. (Dec. 6, 1990). "Phage Antibodies: Filamentous Phage Displaying Antibody Variable Domains," Nature 348:552-554.
Milstein, C. et al. (Oct. 6, 1983). "Hybrid Hybridomas and Their Use in Immunohistochemistry," Nature 305:537-540.
Moorhouse, K.G. et al. (Dec. 1997). "Validation of an HPLC Method for the Analysis of the Charge Heterogeneity of the Recombinant Monoclonal Antibody IDEC-C2B8 After Papain Digestion," J. Pharm. Biomed. Anal. 16(4):593-603.
Mori, Katsuhiro et al. "Engineering Chinese Hamster Ovary Cells to Maximize Effector Function of Produced Antibodies Using FUT8 siRNA," Biotechnology and Bioengineering (Aug. 26, 2004); 88(7):901-908.
Morrison, S.L. (Apr. 28, 1994). "Success in Specification," Nature 368:812-813.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Mosmann, T. (1983). "Rapid Colorimetric Assay for Cellular Growth and Survival: Application to Proliferation and Cytotoxicity Assays," J. Immunol. Methods 65:55-63.
Mulloy, B. (2009). "Chapter 47: Structural Analysis of Glycans," in Essentials of Glycobiology. 2nd edition. Cold Spring Harbor (NY): Cold Spring Harbor Laboratory Press, 10 pages.
Munson, P.J. et al. (1980). "Ligand: A Versatile Computerized Approach for Characterization of Ligand-Binding Systems," Anal. Biochem. 107:220-239.
Nakanishi, T. et al. (2012, e-pub. Oct. 31, 2012). "Development of an Affinity-Matured Humanized Anti-Epidermal Growth Factor Receptor Antibody for Cancer Immunotherapy," Protein Engineering, Design & Selection pp. 1-10.
Nakanishi, T. et al. (2013, e-pub. Oct. 31, 2012). "Development of an Affinity-Matured Humanized Anti-Epidermal Growth Factor Receptor Antibody for Cancer Immunotherapy," Protein Engineering Design and Selection 26(2):113-122.
Neuberger, M. (Jul. 1996). "Generating High-Avidity Human Mabs in Mice," Nature Biotechnol. 14:826.
Niwa, R. et al. (2005). "IgG Subclass-Independent Improvement of Antibody-Dependent Cellular Cytotoxicity by Fucose Removal From Asn297-Linked Oligosaccharides," J. Immunol. Methods 306:151-160.
Oroudjev, E. et al. (Oct. 2010). "Maytansinoid-Antibody Conjugates Induce Mitotic Arrest by Suppressing Microtubule Dynamic Instability," Mol. Cancer Ther. 9(10):2700-2713, 22 pages.
Paborsky, L.R. et al. (1990). "Mammalian Cell Transient Expression of Tissue Factor for the Production of Antigen," Protein Eng. 3(6):547-553.
Plückthun, A. (1994). "Antibodies from *Escherichia coli*," in Chapter 11 the Pharmacology of Monoclonal Antibodies, vol. 113, Rosenburg and Moore eds., SpringerVerlag, New York, pp. 269-315.
Presta, L.G. (1992). "Antibody Engineering," Current Opinion in Structural Biology 2:593-596.
Presta, L.G. et al. (2002). "Engineering Therapeutic Antibodies for Improved Function," Biochemical Society Transactions 30(4):487-490.
Raju, T.S. (2013, e-pub. Feb. 8, 2013). "Assessing Fc Glycan Heterogeneity of Therapeutic Recombinant Monoclonal Antibodies Using NP-HPLC," Methods Mol. Biol. 988:169-180.
Raju, T.S. (Apr. 2003). "Glycosylation Variations with Expression Systems and Their Impact on Biological Activity of Therapeutic Immunoglobulins," BioProcess International 1(4): 44-53.
Ravetch, J.V. et al. (1991). "Fc Receptors," Annu. Rev. Immunol. 9:457-492.
Remillard, S. et al. (Sep. 19, 1975). "Antimitotic Activity of the Potent Tumor Inhibitor Maytansine," Science 189(4207):1002-1005.
Riechmann, L. et al. (Mar. 24, 1988). "Reshaping Human Antibodies for Therapy," Nature 332:323-327.
Routier, F.H. et al. (1997). "The Glycosylation Pattern of a Humanized IgGI Antibody (D1.3) Expressed in CHO Cells," Glycoconjugate Journal 14:201-207.
Schwarze, S.R. et al. (Sep. 3, 1999). "In Vivo Protein Transduction: Delivery of a Biologically Active Protein into the Mouse," Science 285:1569-1572.
Shields, R.L. et al. (Mar. 2, 2001). "High Resolution Mapping of the Binding Site on Human IgG1 for FcγRI, FcγII. FcγIII, and FcRn and Design of IgG1 Variants With Improved Binding to the FcγR," J. Biol. Chem. 276(9):6591-6604.
Shinkawa, Toyohide et al., "The Absence of Fucose But Not the Presence of Galactose or Bisecting N-Acetylglucosamine of Human IgG1 Complex-Type Oligosaccharides Shows the Critical Role of Enhancing Antibody-Dependent Cellular Cytotoxicity," Journal of Biological Chemistry, (Jan. 31, 2003); 278(5):3466-3473.
Shopes, B. et al. (May 1, 1992). "A Genetically Engineered Human IgG Mutant With Enhanced Cytolytic Activity," J. Imniunol. 148:2918-2922.
Sias, P.E. et al. (1990). "ELISA for Quantitation of the Extracellular Domain of p185HER2 in Biological Fluids," J. Immunol. Methods 132:73-80.
Skinner, R.H. et al. (Aug. 5, 1991). "Use of the Glu-Glu-Phe C-terminal Epitope for Rapid Purification of the Catalytic Domain of Normal and Mutant ras GTPase-Activating Proteins," J. Biol. Chem. 266(22):14163-14166.
Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.
Suresh, M.R. et al. (1986). "Bispecific Monoclonal Antibodies From Hybrid Hybridomas," Methods in Enzymology 121:210-228, 19 pages.
Suzuki et al. (Mar. 15, 2007). "A Nonfucosylated Anti-HER2 Antibody Augments Antibody-Dependent Cellular Cytotoxicity in Breast Cancer Patients," Clin. Cancer Res. 13(6): 1875-1882.
Taiwanese Office Action/Search report, dated Jun. 28, 2019, for Taiwanese Patent Application No. 104117520, 6 pages.

(56) References Cited

OTHER PUBLICATIONS

Traunecker, A. et al. (1991). "Bispecific Single Chain Molecules (Janusins) Target Cytotoxic Lymphocytes on HIV Infected Cells," EMBO J. 10(12):3655-3659.

Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.

Umaña, P. et al. (Feb. 1999). "Engineered Glycoforms of an Antineuro-Blastoma IgG 1 With Optimized Antibody-Dependent Cellular Cytotoxic Activity," Nat. Biotechnol. 17:176-180.

Verhoeyen, M. et al. (Mar. 25, 1988). "Reshaping Human Antibodies: Grafting an Antilysozyme Activity," Science 239:1534-1536.

Vitetta, E.S. et al. (Nov. 20, 1987). "Redesigning Nature's Poisons to Create Anti-tumor Reagents," Science 238:1098-1104.

Wolff, E.A. et al. (Jun. 1993). "Monoclonal Antibody Homodimers: Enhanced Antitumor Activity in Nude Mice," Can Res 53:2560-2565.

Written Opinion of the International Searching Authority, dated Nov. 23, 2015, for PCT Application No. PCT/US2015/033402, filed May 29, 2015, 7 pages.

Yamamoto, N. et al. (Jan. 16, 2008, e-pub. Dec. 18, 2007). J. Am. Chem. Soc. 130(2):501-510.

Yamane-Ohnuki, N. et al. (2004, e-pub. Aug. 6, 2004). "Establishment of FUT8 Knockout Chinese hamster Ovary Cells: An Ideal Host Cell Line for Producing Completely Defucosylated Antibodies With Enhances Antibody-Dependent Cellular Cytotoxicity," Biotech. Bioeng. 87:614-622.

Yamane-Ohnuki, N. et al. (May/Jun. 2009). "Production of Therapeutic Antibodies With Controlled Fucosylation," mAbs 1(3):230-236.

Yazawa S. et al. (Apr. 29, 1986). "Alpha-L-Fucosidase From Aspergillus Niger: Demonstration of a Novel Alpha-L-1-6)-Fucosidase Acting on Glycopeptides," Biochem Biophys Res Commun. 136:563-569.

Zapata, G. et al. (1995). "Engineering Linear F(ab')2 Fragments for Efficient Production in *Escherichia coli* and Enhanced Antiproliferative Activity," Protein Eng. 8(10):1057-1062.

\* cited by examiner

Fig. 6A (Whole IgG)

| Area % | HPLC 2-AB Labeled Glycan Analysis | | | |
|---|---|---|---|---|
| | G0 | G0F | G1F | G2F |
| ERBITUX KGaA | 1.6 | 51.1 | 39.5 | 7.8 |
| HLX05 | 2.5 | 61.2 | 32.4 | 3.8 |
| 1-26/2-68 | 1.8 | 73.9 | 22.6 | 1.7 |
| 1-26/3-67 | 3.2 | 78.4 | 17.2 | 1.2 |
| 8/33 | 2.0 | 70.2 | 25.8 | 2.0 |
| 34/33 | 1.3 | 56.0 | 37.4 | 5.3 |

(130619) Conclusion of Glycan on Fab/Fc (Separate Fab & Fc)

| Sample | Fragment | Glycan Profile |
|---|---|---|
| Erbitux (Merk) KGaA | Fc | G0F<br>G1F<br>G2F (trace) |
|  | Fab | G2F+2*Gal<br>G2F+Gal+SA(NeuGc) |
| HLX05 | Fc | G0F<br>G1F<br>G2F (trace) |
|  | Fab | G2F<br>G2F+SA(NeuAc)<br>G2F+2*SA(NeuAc) |
| 1-26/3-67 | Fc | G0F<br>G1F |
|  | Fab | --- |

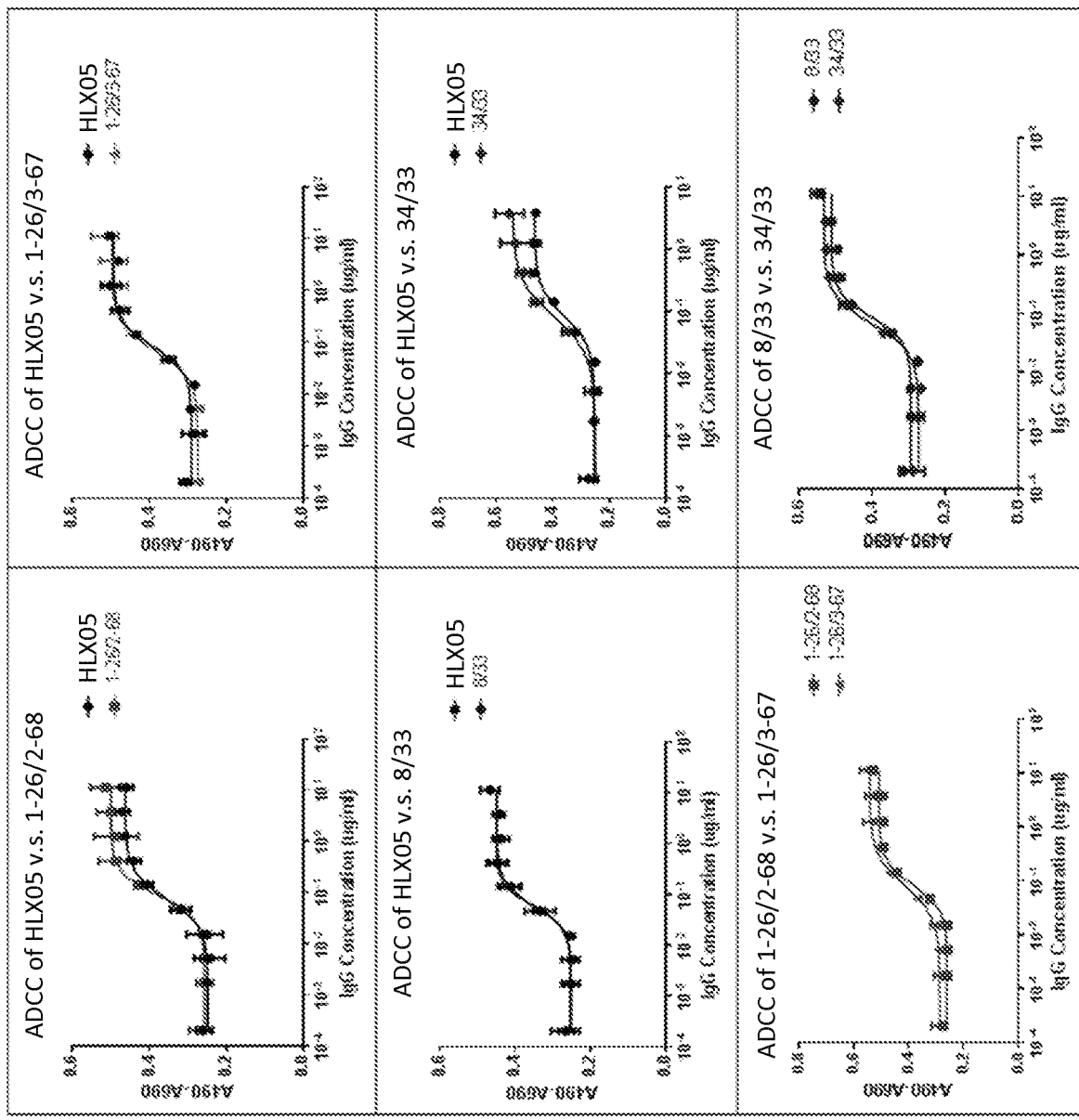

Fig. 8G

| (ng/ml) | ADCC (PBMC 400K/well) | | ADCC (PBMC 600K/well) | |
|---|---|---|---|---|
| | Avg EC50 | % of Activity | Avg EC50 | % of Activity |
| HLX05 | 99.7 | 100 | 80.6 | 100 |
| 1-26/2-68 | 118.7 | 84 | 84.7 | 95 |
| 1-26/3-67 | 110.2 | 90 | 74.2 | 109 |
| 8/33 | 91.4 | 109 | 87.0 | 93 |
| 34/33 | 80.3 | 124 | 72.9 | 111 |

Fig. 9G

| (ng/ml) | MTT | |
|---|---|---|
| | Avg IC50 | % of Activity |
| HLX05 | 285.9 | 100 |
| 1-26/2-68 | 254.5 | 112 |
| 1-26/3-67 | 220.2 | 130 |
| 8/33 | 217.2 | 132 |
| 34/33 | 236.2 | 121 |

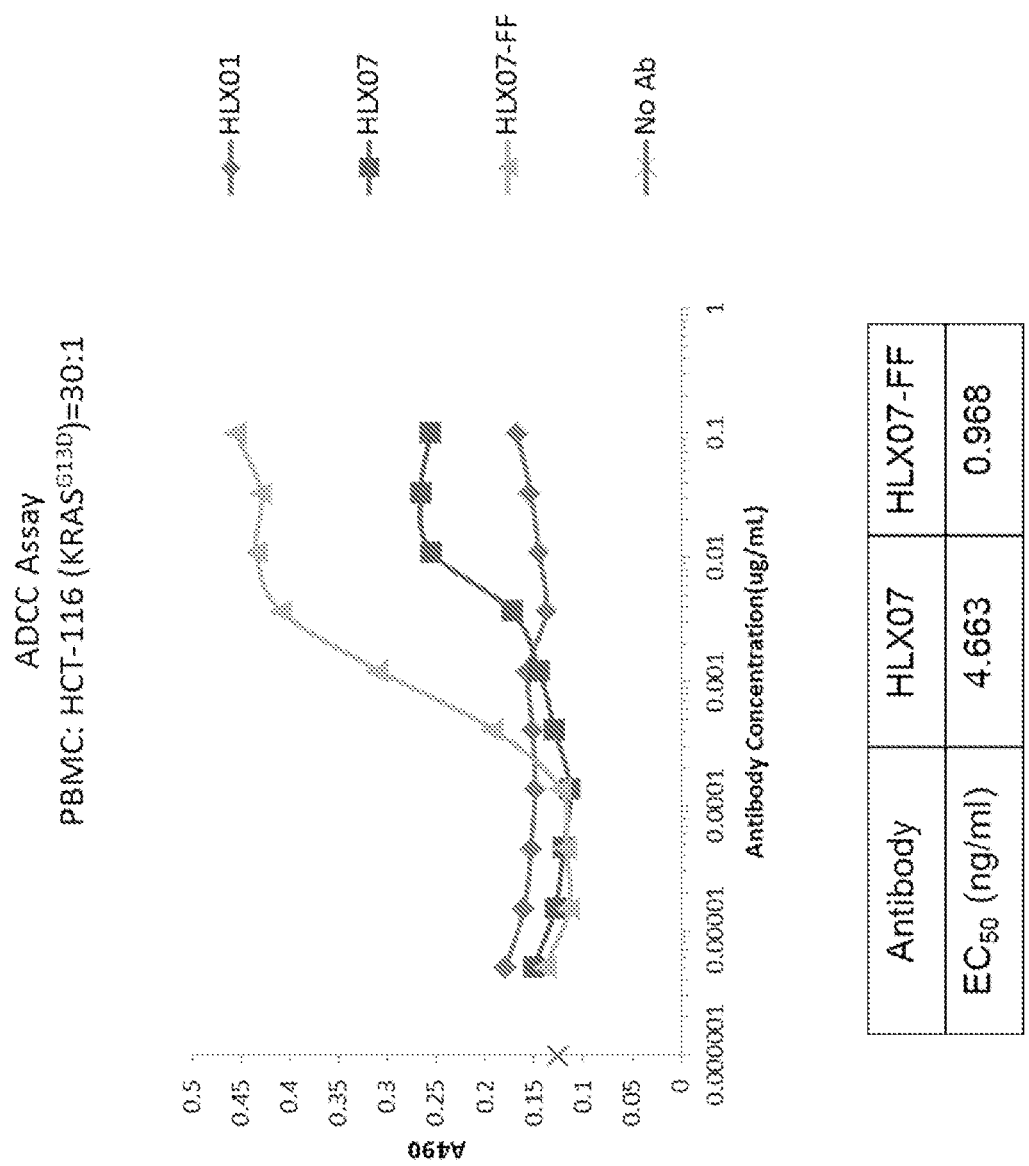

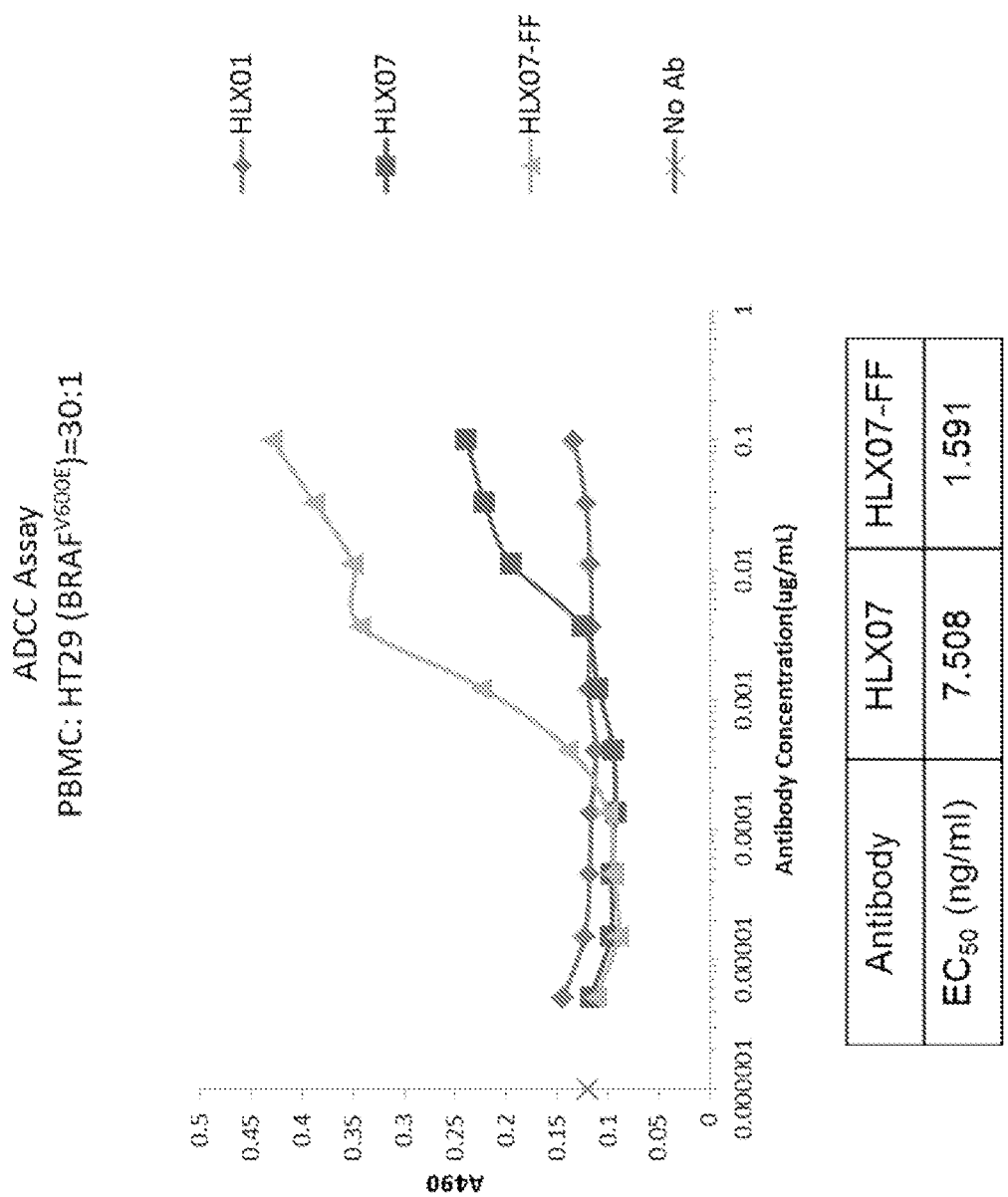

ANTI-EPIDERMAL GROWTH FACTOR RECEPTOR (EGFR) ANTIBODIES

CROSS REFERENCE TO RELATED APPLICATIONS

This application is a continuation of U.S. patent application Ser. No. 15/315,371, which adopts the International Filing Date of May 29, 2015, and is a National Phase application under 35 U.S.C. § 371 of International Application No. PCT/US2015/033402, having an International Filing Date of May 29, 2015, which claims priority benefit of U.S. Provisional Application Ser. No. 62/005,887, filed May 30, 2014, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 719902000101SEQLIST.TXT, date recorded: Jan. 31, 2020, size: 15 KB).

BACKGROUND OF THE INVENTION

Epidermal growth factor receptor (also known as EGFR, ErbB-1 and HER1) is a cell surface receptor of the ErbB family of receptors, a subfamily of four closely related receptor tyrosine kinases, including EGFR (ErbB-1), HER2/c-neu (ErbB-2), Her 3 (ErbB-3) and Her 4 (ErbB-4). Binding of EGFR to a ligand (such as epidermal growth factor (EGF), transforming growth factor a (TGF α), HB-EGF, amphiregulin, betacellulin/BTC, epigen/EPGN, or other) induces receptor dimerization and autophosphorylation of several tyrosine (Y) residues (Y992, Y1045, Y1068, Y1148, and Y1173) in the C-terminal domain of EGFR. This autophosphorylation elicits downstream activation of several signal transduction cascades, including the MAPK, Akt, and JNK pathways, leading to cell migration, adhesion, and cell proliferation.

Mutations, amplifications or misregulations of EGFR or family members are implicated in about 30% of all epithelial cancers. For example, mutations that lead to EGFR overexpression or overactivity have been associated with a number of cancers, including lung cancer, anal cancers, head and neck cancers, and glioblastoma multiforme. The identification of EGFR as an oncogene has led to the need for the development of anticancer therapeutics directed against EGFR. The present invention meets this and other needs.

BRIEF SUMMARY OF THE INVENTION

Provided by the invention is an anti-epidermal growth factor receptor (EGFR) antibody or antigen binding fragment thereof, comprising a heavy chain variable domain sequence comprising (1) a CDR-H1 comprising the amino acid sequence N/T/Q-YGVH (SEQ ID NO: 4); (2) a CDR-H2 comprising the amino acid sequence Y-N/A/G/D-T/D/N-P/K/E-FTSRF (SEQ ID NO: 9); and (3) a CDR-H3 comprising the amino acid sequence T/D-Y/L-YDL-E/N-FAY (SEQ ID NO: 14); and a light chain variable domain sequence comprising (1) a CDR-L1 comprising the amino acid sequence I-G/R/S-T/L/P-NIH (SEQ ID NO: 20); (2) a CDR-L2 comprising the amino acid sequence KY-A/G-SE-S/T-I-S/R (SEQ ID NO: 24); and (3) a CDR-L3 comprising the amino acid sequence NWPT-T/L/S/A/Y (SEQ ID NO: 30).

In some embodiments, the antibody comprises a heavy chain variable domain sequence comprising (1) a CDR-H1 comprising an amino acid sequence selected from consisting of SEQ ID NOs: 1-3; (2) a CDR-H2 comprising an amino acid sequence selected from consisting of SEQ ID NOs: 5-8; and (3) a CDR-H3 comprising an amino acid sequence selected from consisting of SEQ ID NOs: 10-13; and a light chain variable domain sequence comprising (1) a CDR-L1 comprising an amino acid sequence selected from consisting of SEQ ID NOs: 15-19; (2) a CDR-L2 comprising an amino acid sequence selected from consisting of SEQ ID NOs: 21-23; (3) a CDR-L3 comprising an amino acid sequence selected from consisting of SEQ ID NOs: 25-29. In some embodiments according to (or as applied to) any of the embodiments above, the antibody comprises a heavy chain variable domain sequence comprising (1) a CDR-H1 comprising the amino acid sequence NYGVH (SEQ ID NO: 1); (2) a CDR-H2 comprising the amino acid sequence YNTPFTSRF (SEQ ID NO: 5); and (3) a CDR-H3 comprising the amino acid sequence TYYDYEFAY (SEQ ID NO: 10); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTT (SEQ ID NO: 25). In some embodiments according to (or as applied to) any of the embodiments above, the antibody comprises a heavy chain variable domain sequence comprising (1) a CDR-H1 comprising the amino acid sequence NYGVH (SEQ ID NO: 1); (2) a CDR-H2 comprising the amino acid sequence YNTPFTSRF (SEQ ID NO: 5); and (3) a CDR-H3 comprising the amino acid sequence DYYDYEFAY (SEQ ID NO: 11); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTS (SEQ ID NO: 27). In some embodiments according to (or as applied to) any of the embodiments above, the antibody comprises a heavy chain variable domain sequence comprising (1) a CDR-H1 comprising the amino acid sequence NYGVH (SEQ ID NO: 1); (2) a CDR-H2 comprising the amino acid sequence YGNEFTSRF (SEQ ID NO: 8); and (3) a CDR-H3 comprising the amino acid sequence DYYDYEFAY (SEQ ID NO: 11); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTS (SEQ ID NO: 27).

In some embodiments according to (or as applied to) any of the embodiments above, the antibody comprises a heavy chain variable domain sequence comprising (1) a CDR-H1 comprising the amino acid sequence NYGVH (SEQ ID NO: 1); (2) a CDR-H2 comprising the amino acid sequence YATEFTSRF (SEQ ID NO: 7); and (3) a CDR-H3 comprising the amino acid sequence DYYDYEFAY (SEQ ID NO: 11); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTS (SEQ ID NO: 27). In some embodiments according to (or as applied to)

any of the embodiments above, the antibody comprises a heavy chain variable domain sequence comprising (1) a CDR-H1 comprising the amino acid sequence NYGVH (SEQ ID NO: 1); (2) a CDR-H2 comprising the amino acid sequence YDDKFTSRF (SEQ ID NO: 6); and (3) a CDR-H3 comprising the amino acid sequence DYYDYEFAY (SEQ ID NO: 11); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTS (SEQ ID NO: 27). In some embodiments according to (or as applied to) any of the embodiments above, the antibody comprises a heavy chain variable domain sequence comprising (1) a CDR-H1 comprising the amino acid sequence TYGVH (SEQ ID NO: 3); (2) a CDR-H2 comprising the amino acid sequence YGNEFTSRF (SEQ ID NO: 8); and (3) a CDR-H3 comprising the amino acid sequence DYYDYEFAY (SEQ ID NO: 11); and a light chain variable domain sequence comprising (1) a CDR-L1 comprising the amino acid sequence IRTNIH (SEQ ID NO: 16); (2) a CDR-L2 comprising the amino acid sequence KYGSESIS (SEQ ID NO: 22); and (3) a CDR-L3 comprising the amino acid sequence NWPTS (SEQ ID NO: 27). In some embodiments according to (or as applied to) any of the embodiments above, the antibody comprises a heavy chain variable domain sequence comprising (1) a CDR-H1 comprising the amino acid sequence TYGVH (SEQ ID NO: 3); (2) a CDR-H2 comprising the amino acid sequence YGNEFTSRF (SEQ ID NO: 8); and (3) a CDR-H3 comprising the amino acid sequence DYYDYEFAY (SEQ ID NO: 11); and a light chain variable domain sequence comprising (1) a CDR-L1 comprising the amino acid sequence ISTNIH (SEQ ID NO: 19); (2) a CDR-L2 comprising the amino acid sequence KYGSESIS (SEQ ID NO: 22); and (3) a CDR-L3 comprising the amino acid sequence NWPTS (SEQ ID NO: 27).

Also provided by the invention is an aglycosylated CDR-H2 anti-epidermal growth factor receptor (EGFR) antibody or antigen binding fragment thereof comprising a heavy chain variable domain comprising a CDR-H2 selected comprising the amino acid sequence Y-A/G/D-D/N-K/E-FTSRF (SEQ ID NO: 31). In some embodiments, the heavy chain variable domain further comprises a CDR-H1 comprising the amino acid sequence N/T/Q-YGVH (SEQ ID NO: 4) and a CDR-H3 comprising the amino acid sequence T/D-Y/L-YDY-E/N-FAY (SEQ ID NO: 14). In some embodiments according to (or as applied to) any of the embodiments above, the antibody or antigen binding fragment thereof further comprises a light chain variable domain sequence comprising a CDR-L1 comprising the amino acid sequence I-G/R/S-T/L/P-NIH (SEQ ID NO: 20); a CDR-L2 comprising the amino acid sequence KY-A/G-SE-S/T-I-S/R (SEQ ID NO: 24); and a CDR-L3 comprising the amino acid sequence NWPT-T/L/S/A/Y (SEQ ID NO: 30).

In some embodiments according to (or as applied to) any of the embodiments above, the antibody comprises an Fc sequence of a human IgG. In some embodiments according to (or as applied to) any of the embodiments above, the antigen binding fragment is selected from the group consisting of a Fab, Fab', a F(ab)' 2, a single-chain Fv (scFv), an Fv fragment, a diabody, and a linear antibody. In some embodiments according to (or as applied to) any of the embodiments above, the antibody is a multispecific antibody. In some embodiments according to (or as applied to) any of the embodiments above, the anti-EGFR antibody or antigen binding fragment thereof is conjugated to a therapeutic agent. In some embodiments according to (or as applied to) any of the embodiments above, the anti-EGFR antibody or antigen binding fragment thereof is conjugated to a label. In some embodiments according to (or as applied to) any of the embodiments above, the label is selected from the group consisting of a radioisotope, a fluorescent dye, and an enzyme.

In some embodiments according to (or as applied to) any of the embodiments above, the antibody is an afucosylated antibody.

In some embodiments according to (or as applied to) any of the embodiments above, the anti-EGFR antibody or antigen binding fragment thereof is conjugated to a cytotoxic agent. In some embodiments according to (or as applied to) any of the embodiments above, the cytotoxic agent is a maytansine or a derivative thereof. In some embodiments according to (or as applied to) any of the embodiments above, the maytansine or a derivative thereof is DM-1.

The invention provides an isolated nucleic acid molecule that encodes the anti-EGFR antibody or antigen binding fragment thereof according to (or as applied to) any of the embodiments above. Also provided is an expression vector encoding the nucleic acid molecule according to (or as applied to) any of the embodiments above. Cells comprising the expression vector according to (or as applied to) any of the embodiments above are also provided. The invention also provides a method of producing an antibody comprising culturing a cell according to (or as applied to) any of the embodiments above and recovering the antibody or antigen-binding fragment thereof from the cell culture. In some embodiments according to (or as applied to) any of the embodiments above, the cell is a mammalian cell. In some embodiments according to (or as applied to) any of the embodiments above, the mammalian cell is a CHO cell. In some embodiments according to (or as applied to) any of the embodiments above, the cell is a stable mammalian cell line. In some embodiments according to (or as applied to) any of the stable mammalian cell line is a CHO cell line.

The invention provides a composition comprising the anti-EGFR antibody or antigen binding fragment thereof according to (or as applied to) any of the embodiments above and a pharmaceutically acceptable carrier.

The invention provides a method of detecting an EGFR protein in sample from a patient by contacting the anti-EGFR antibody or antigen binding fragment thereof according to (or as applied to) any of the embodiments above to the sample and detecting the anti-EGFR antibody bound to the EGFR protein. In some embodiments according to (or as applied to) any of the embodiments above, the anti-EGFR antibody or antigen binding fragment thereof is used an immunohistochemistry assay (IHC) or in an ELISA assay.

Also provided is a method of treating cancer in a subject, comprising administering an effective amount of the composition according to (or as applied to) to the subject. Also provided is a composition comprising an anti-EGFR antibody or antigen binding fragment thereof according to (or as applied to) any of the embodiments above for use in the treatment of cancer. Provided is the use of an anti-EGFR antibody or antigen binding fragment thereof according to (or as applied to) any of the embodiments above in the manufacture of a medicament for treating cancer. In some embodiments according to (or as applied to) any of the embodiments above, the cancer is selected from colorectal cancer, lung cancer, and head and neck cancer. In some embodiments according to (or as applied to) any of the embodiments above, the subject is further administered a therapeutic agent selected from the group consisting of an anti-neoplastic agent, a chemotherapeutic agent, a growth inhibitory agent and a cytotoxic agent.

In some embodiments according to (or as applied to) any of the embodiments above, the cancer is throat cancer. In some embodiments according to (or as applied to) any of the embodiments above, the subject is further administered radiation therapy.

In some embodiments according to (or as applied to) any of the embodiments above, subject is further administered a therapeutic agent selected from the group consisting of an anti-neoplastic agent, a chemotherapeutic agent, a growth inhibitory agent and a cytotoxic agent.

In certain embodiments according to (or as applied to) any of the embodiments above, the subject to whom a composition comprising an anti-EGFR antibody or antigen binding fragment thereof described herein is administered is wild-type for KRAS. In certain embodiments according to (or as applied to) any of the embodiments above, the subject to whom a composition comprising an anti-EGFR antibody or antigen binding fragment thereof described herein is administered has the KRAS$^{G13D}$ mutation. In certain embodiments according to (or as applied to) any of the embodiments above, the subject to whom a composition comprising an anti-EGFR antibody or antigen binding fragment thereof described herein is administered is wild-type for BRAF. In certain embodiments according to (or as applied to) any of the embodiments above, the subject to whom a composition comprising an anti-EGFR antibody or antigen binding fragment thereof described herein is administered has the BRAF$^{V600E}$ mutation.

In certain embodiments according to (or as applied to) any of the embodiments above, the subject to whom a composition comprising an anti-EGFR antibody or antigen binding fragment thereof described herein is administered is resistant to Erbitux or its biosimilar. In certain embodiments according to (or as applied to) any of the embodiments above, the subject to whom a composition comprising an anti-EGFR antibody or antigen binding fragment thereof described herein is administered has progressed on Erbitux or its biosimilar. In certain embodiments according to (or as applied to) any of the embodiments above, the subject to whom a composition comprising an anti-EGFR antibody or antigen binding fragment thereof described herein is administered is refractory to Erbitux or its biosimilar.

BRIEF DESCRIPTION OF THE DRAWINGS

FIGS. 6A and 6B show the results of glycan analyses performed on HLX05, ERBITUX® and anti-EGFR antibodies 1-26/2-68, 1-26/3-67, #8/#33, #34/#33.

FIG. 8A shows the results of analyses performed to compare ADCC activity of HLX05 and anti-EGFR antibody 1-26/2-68. FIG. 8B shows the results of analyses performed to compare ADCC activity of HLX05 and anti-EGFR antibody #8/#33. FIG. 8C shows the results of analyses performed to compare ADCC activity of anti-EGFR antibodies 1-26/2-68 and 1-26/3-67. FIG. 8D shows the results of analyses performed to compare ADCC activity of HLX05 and anti-EGFR antibody 1-26/3-67. FIG. 8E shows the results of analyses performed to compare ADCC activity of HLX05 and anti-EGFR antibody #34/#33. FIG. 8F shows the results of analyses performed to compare ADCC activity of anti-EGFR antibodies #8/#33 and #34/#33. FIG. 8G shows quantified results of analyses performed to compare ADCC activity of HLX05, 1-26/2-68, 1-26/3-67, #8/#33, and #34/#33.

FIG. 9G shows quantified results of analyses performed to compare the anti-proliferative effects of HLX05, 1-26/2-68, 1-26/3-67, #8/#33, and #34/#33 on A431 cells.

FIG. 15B shows the ADCC activity of 1-26/3-67-FF (i.e., "fuscose free"), 1-26/3-67, and control antibody against HCT-116cells (KRAS$^{G13D}$) with PBMC effector cells. FIG. 15C shows the ADCC activity of 1-26/3-67-FF (i.e., "fuscose free"), 1-26/3-67, and control antibody against HT29 cells (BRAF$^{V600E}$) with PBMC effector cells.

DETAILED DESCRIPTION OF THE INVENTION

Figure 1:
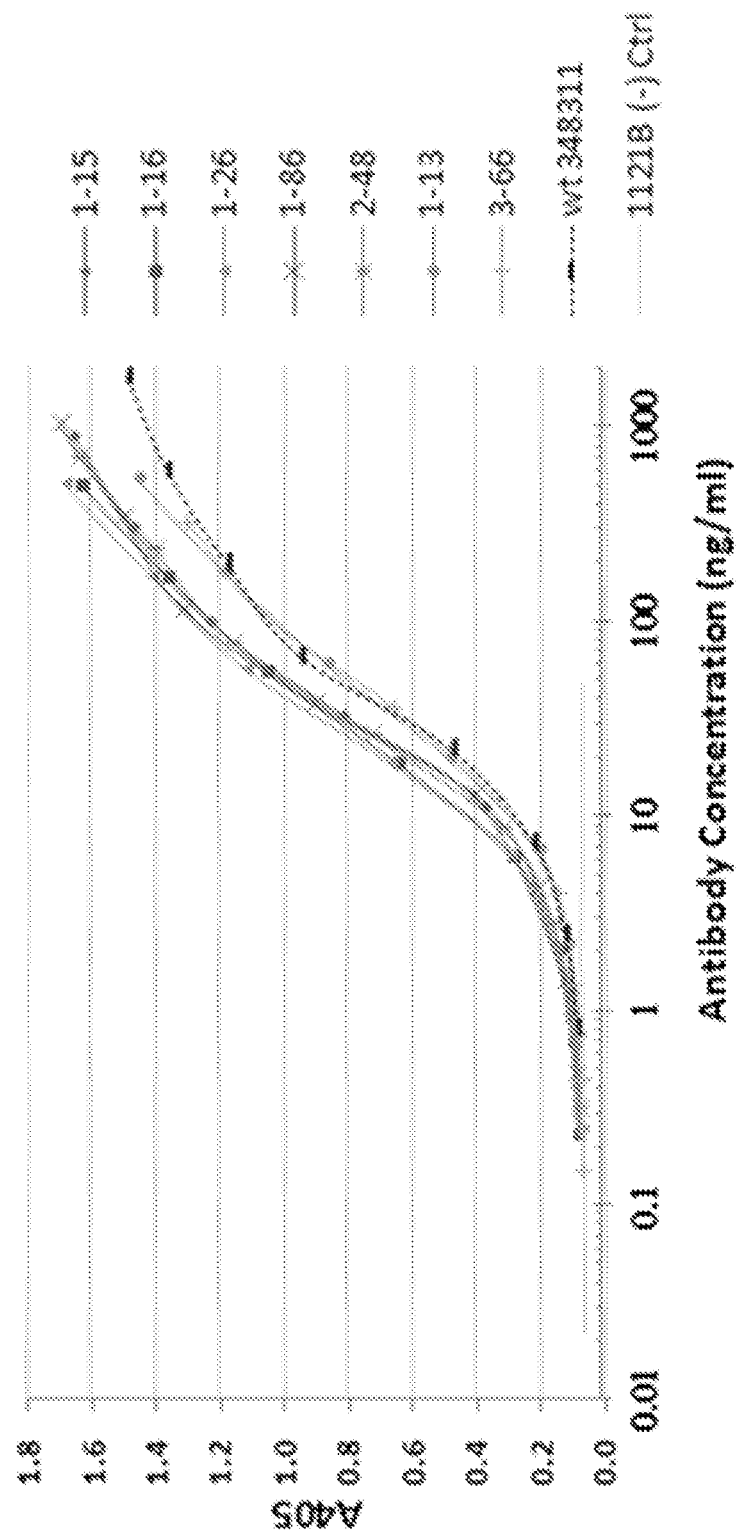
FIG. 1 shows the results of ELISAs performed to compare the binding of anti-EGFR Fab variants obtained from a CDR-L3/CDR-H3 library to EGFR.

The present invention provides novel anti-epidermal growth factor receptor (EGFR) antibodies. Applicants have surprisingly found that the anti-EGFR antibodies described herein exhibit enhanced therapeutic efficacy compared to ERBITUX® (cetuximab), an FDA-approved anti-EGFR antibody used for the treatment of metastatic colorectal cancer and head and neck cancer. Anti-EGFR antibodies described herein also exhibit longer half-lives than ERBITUX®.

In a related aspect, the invention provides novel anti-EGFR antibodies lacking an N-glycosylation motif in CDR-H2. Glycosylation within the light chain variable region and/or the heavy chain variable region of an antibody, such as the N-glycan at Asn 99 of the VH region of ERBITUX®, can reduce an antibody's therapeutic efficacy by interfering with antigen binding. Moreover, such glycosylation can cause heterogeneity within a batch of antibodies that may result in altered function, immunogenicity, or stability. Fewer glycoforms are present in production batches of anti-EGFR antibodies lacking a glycosylation motif in CDR-H2.

Also provided are immunoconjugates, nucleic acids encoding the novel anti-EGFR antibodies described herein, and compositions (such as pharmaceutical compositions). The invention also provides methods of using novel anti-EGFR antibodies to detect EGFR in a sample (such as an in vivo or ex vivo sample), compositions comprising such antibodies for use in treating cancer, and uses of such antibodies in the manufacture of a medicament for the treatment of cancer.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods provided herein contemplate any one or more of these aspects of treatment.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

The term "adjuvant therapy" refers to treatment given after the primary therapy, usually surgery. Adjuvant therapy for cancer or disease may include immune therapy, chemotherapy, radiation therapy, or hormone therapy.

The term "maintenance therapy" refers to scheduled retreatment that is given to help maintain a previous treatment's effects. Maintenance therapy is often given to help keep cancer in remission or prolong a response to a specific therapy regardless of disease progression.

The term "invasive cancer" refers to cancer that has spread beyond the layer of tissue in which it started into the normal surrounding tissues. Invasive cancers may or may not be metastatic.

The term "non-invasive cancer" refers to a very early cancer or a cancer that has not spread beyond the tissue of origin.

The term "progression-free survival" in oncology refers to the length of time during and after treatment that a cancer does not grow. Progression-free survival includes the amount of time patients have experienced a complete response or a partial response, as well as the amount of time patients have experienced stable disease.

The term "progressive disease" in oncology can refer to a tumor growth of more than 20 percent since treatment began—either due to an increase in mass or a spread in the tumor.

A "disorder" is any condition that would benefit from treatment with the antibody. For example, mammals who suffer from or need prophylaxis against abnormal EGFR activity. This includes chronic and acute disorders or diseases including those pathological conditions which predispose the mammal to the disorder in question. Non-limiting examples of disorders to be treated herein include cancer (such as head and neck cancer, throat cancer, colorectal cancer, lung cancer, etc.).

"Tumor", as used herein, refers to all neoplastic cell growth and proliferation, whether malignant or benign, and all pre-cancerous and cancerous cells and tissues.

The term "antibody" is used in the broadest sense and specifically covers, for example, single monoclonal antibodies (including agonist, antagonist, and neutralizing antibodies), antibody compositions with polyepitopic specificity, polyclonal antibodies, single chain anti-antibodies, and fragments of antibodies (see below) as long as they specifically bind a native polypeptide and/or exhibit a biological activity or immunological activity of this invention. According to one embodiment, the antibody binds to an oligomeric form of a target protein, e.g., a trimeric form. According to another embodiment, the antibody specifically binds to a protein, which binding can be inhibited by a monoclonal antibody of this invention (e.g., a deposited antibody of this invention, etc.). The phrase "functional fragment or analog" of an antibody is a compound having a qualitative biological activity in common with an antibody to which it is being referred. For example, a functional fragment or analog of an antibody of this invention can be one which can specifically bind to EGFR. In one embodiment, the antibody can prevent or substantially reduce the ability of an EGFR to induce cell proliferation.

An "isolated antibody" is one which has been identified and separated and/or recovered from a component of its natural environment. Contaminant components of its natural environment are materials which would interfere with diagnostic or therapeutic uses for the antibody, and can include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Ten and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

| CDR DEFINITIONS | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" is not to be construed as requiring production of the antibody by any particular method. For example, the monoclonal antibodies useful in the present invention can be prepared by the hybridoma methodology first described by Kohler et al. Nature. 256:495 (1975), or can be made using recombinant DNA methods in bacterial, eukaryotic animal or plant cells (see, e.g., U.S. Pat. No. 4,816,567). The "monoclonal antibodies" can also be isolated from phage antibody libraries using the techniques described in Clackson et al., Nature, 352:624-628 (1991), Marks et al., J. Mol. Biol., 222:581-597 (1991), and the Examples below, for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

An "intact" antibody is one which comprises an antigen-binding site as well as a $C_L$ and at least heavy chain constant domains, $C_H1$, $C_H2$ and $C_H3$. The constant domains can be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

The expression "linear antibodies" generally refers to the antibodies described in Zapata et al., Protein Eng., 8(10): 1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by di sulfides. The effector functions of antibodies are determined by sequences in the Fc region, which region is also the part recognized by Fc receptors (FcR) found on certain types of cells.

A "variant Fc region" comprises an amino acid sequence which differs from that of a native sequence Fc region by virtue of at least one "amino acid modification" as herein defined. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. In one embodiment, the variant Fc region herein will possess at least about 80% homology, at least about 85% homology, at least about 90% homology, at least about 95% homology or at least about 99% homology with a native sequence Fc region. According to another embodiment, the variant Fc region herein will possess at least about 80% homology, at least about 85% homology, at least about 90% homology, at least about 95% homology or at least about 99% homology with an Fc region of a parent polypeptide.

The term "Fc region-comprising polypeptide" refers to a polypeptide, such as an antibody or immunoadhesin (see definitions elsewhere herein), which comprises an Fc region. The C-terminal lysine (residue 447 according to the EU numbering system) of the Fc region may be removed, for example, during purification of the polypeptide or by recombinantly engineering the nucleic acid encoding the polypeptide. Accordingly, a composition comprising polypeptides, including antibodies, having an Fc region according to this invention can comprise polypeptides populations with all K447 residues removed, polypeptide populations with no K447 residues removed or polypeptide populations having a mixture of polypeptides with and without the K447 residue.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors; and B cell activation. A "native sequence Fc region" comprises an amino acid sequence identical to the amino acid sequence of an Fc region found in nature. Examples of Fc sequences are described in, for example, but not limited to, Kabat et al., *Sequences of Immunological Interest*. 5th Ed. Public Health Service, National Institutes of Health, Bethesda, Md. (1991)).

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, N.Y., pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

The terms "Fc receptor" or "FcR" are used to describe a receptor that binds to the Fc region of an antibody. In one embodiment, an FcR of this invention is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). The term includes allotypes, such as FcγRIIIA allotypes: FcγRIIIA-Phe158, FcγRIIIA-Va1158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region (also referred to as "1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. In previous reports, FcR binding was generally attributed to amino acid residues in the lower hinge region of an IgG Fc region.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG)

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "binding domain" refers to the region of a polypeptide that binds to another molecule. In the case of an FcR, the binding domain can comprise a portion of a polypeptide chain thereof (e.g. the alpha chain thereof) which is responsible for binding an Fc region. One useful binding domain is the extracellular domain of an FcR alpha chain.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent Kd or IC50 value) than the parent polypeptide or a native sequence IgG Fc. According to some embodiments, the improvement in binding compared to a parent polypeptide is about 3 fold, preferably about 5, 10, 25, 50, 60, 100, 150, 200, up to 500 fold, or about 25% to 1000% improvement in binding. The polypeptide variant which "exhibits decreased binding" to an FcR, binds at least one FcR with lower affinity (e.g., higher apparent Kd or higher IC50 value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγR1, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 or in the Examples below may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1998).

The polypeptide comprising a variant Fc region which "exhibits increased ADCC" or mediates antibody-dependent cell-mediated cytotoxicity (ADCC) in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g. in an animal model etc. In one embodiment, the preferred variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

An "effective amount" of an anti-EGFR antibody (or fragment thereof) or composition as disclosed herein is an amount sufficient to carry out a specifically stated purpose. An "effective amount" can be determined empirically and by known methods relating to the stated purpose.

The term "therapeutically effective amount" refers to an amount of an anti-EGFR antibody (or fragment thereof) or composition as disclosed herein, effective to "treat" a disease or disorder in a mammal (aka patient). In the case of cancer, the therapeutically effective amount of the anti-EGFR antibody (or fragment thereof) or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-EGFR antibody (or fragment thereof) or composition as disclosed herein can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

A "growth inhibitory amount" of an anti-EGFR antibody (or fragment thereof) or composition as disclosed herein of this invention is an amount capable of inhibiting the growth of a cell, especially tumor, e.g., cancer cell, either in vitro or in vivo. A "growth inhibitory amount" of a polypeptide, antibody, antagonist or composition of this invention for purposes of inhibiting neoplastic cell growth can be determined empirically and by known methods or by examples provided herein.

A "cytotoxic amount" of an anti-EGFR antibody (or fragment thereof) or composition of this invention is an amount capable of causing the destruction of a cell, especially tumor, e.g., cancer cell, either in vitro or in vivo. A "cytotoxic amount" of an anti-EGFR antibody (or fragment thereof) or composition of this invention for purposes of inhibiting neoplastic cell growth can be determined empirically and by methods known in the art.

A "growth inhibitory amount" of an anti-EGFR antibody (or fragment thereof) or composition of this invention is an amount capable of inhibiting the growth of a cell, especially tumor, e.g., cancer cell, either in vitro or in vivo. A "growth inhibitory amount" of a an anti-EGFR antibody (or fragment thereof) or composition of this invention for purposes of inhibiting neoplastic cell growth can be determined empirically and by known methods or by examples provided herein.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "detecting" is intended to include determining the presence or absence of a substance or quantifying the amount of a substance (such as EGFR). The term thus refers to the use of the materials, compositions, and methods of the present invention for qualitative and quantitative determinations. In general, the particular technique used for detection is not critical for practice of the invention.

For example, "detecting" according to the invention may include: observing the presence or absence of EGFR gene product, mRNA molecules, or an EGFR polypeptide; a change in the levels of an EGFR polypeptide or amount bound to a target; a change in biological function/activity of an EGFR polypeptide. In some embodiments, "detecting" may include detecting wild type EGFR levels (e.g., mRNA or polypeptide levels). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the invention described herein include "comprising," "consisting," and "consisting essentially of" aspects and embodiments.

All references cited herein, including patent applications and publications, are hereby incorporated by reference in their entirety.

Anti-Epidermal Growth Factor Receptor (EGFR) Antibodies

The present invention is based on the identification of novel antibodies that bind epidermal growth factor receptor (EGFR). The anti-EGFR antibodies can be used in a variety of therapeutic and diagnostic methods. For example, the anti-EGFR antibodies can be used alone or in combination with other agents in treating disease characterized by abnormal EGFR expression or abnormal EGFR activity, including, e.g., head and neck cancer, throat cancer, colorectal cancer, lung cancer, etc. The antibodies provided herein can also be used for detecting EGFR protein in patients or patient samples by administering the anti-EGFR antibodies to patients and detecting the anti-EGFR antibody bound to the EGFR protein in a sample from the patient (e.g., in vivo or ex vivo) or by contacting the anti-EGFR antibodies with samples from patients and detecting qualitatively or quantitatively the anti-EGFR antibody bound to the EGFR protein.

Epidermal growth factor receptor or "EGFR" (also known as, e.g., ERBB, ERBB1, HER1, PIG61, mENA, Cell Growth Inhibiting Protein 40, Cell Proliferation-Inducing Protein 61, and EC 2.7.10.1) is a member of the ErbB family of receptors, a subfamily of four closely related receptor tyrosine kinases. EGFR is activated by binding of its specific ligands (such as epidermal growth factor (EGF), TGF α, heparin-binding EGF-like growth factor, amphiregulin, betacellulin (BTC), epigen (EPGN), and others), whereupon EGFR undergoes dimerization and tyrosine autophosphorylation. Autophosphorylation leads to downstream activation of, e.g., phosphatidyl 3-kinase (PI3K), Phospholipase (PL) C-g1, Akt, Ras, Raf and mitogen-activated protein kinase (MAPK), and other signal transduction cascades associated with cell proliferation, motility, adhesion, and migration. Aberrant EGFR expression or EGFR activity is associated with many cancers (such as head and neck cancer, throat cancer, colorectal cancer, lung cancer, etc.)).

An anti-EGFR antibody is an antibody that binds to EGFR with sufficient affinity and specificity. Preferably, an anti-EGFR antibody provided herein (or the antigen-binding fragment thereof) can be used as a therapeutic agent in targeting and interfering with diseases or conditions wherein the EGFR activity is involved. An anti-EGFR antibody will usually not bind to other ERBb family, such as Her2/Neu/ErbB2, Her3/ERBb3 or Her4/ERBb4. Preferably, the anti-EGFR antibody is a recombinant humanized anti-EGFR monoclonal antibody. According to one embodiment, the anti-EGFR antibody comprises the CDRs, the variable heavy chain region, and/or the variable light region of any one of the antibodies disclosed herein.

In certain embodiments, the anti-EGFR antibody (or antigen binding fragment thereof) is a variant of an anti-EGFR antibody comprising a heavy chain variable domain sequence comprising a CDR-H1 comprising the amino acid sequence NYGVH (SEQ ID NO: 1); a CDR-H2 comprising the amino acid sequence YNTPFTSRF (SEQ ID NO: 5); and a CDR-H3 comprising the amino acid sequence TYYDYE- FAY (SEQ ID NO: 10); and a light chain variable domain sequence comprising a CDR-L1 comprising the amino acid sequence IGTNIH (SEQ ID NO: 15); a CDR-L2 comprising the amino acid sequence KYASESIS (SEQ ID NO: 21); and (3) a CDR-L3 comprising the amino acid sequence NWPTT (SEQ ID NO: 25), wherein the variant comprises at least one amino acid substitution in one or more of SEQ ID NOs: 5, 10, 15, 21, and/or 25. In some embodiments the variant comprises at least 1, at least 2, at least 3, at least 4, at least 5, at least 6, at least 7, at least 8, at least 9, or at least 10 amino acid substitutions in one or more of SEQ ID NOs: 5, 10, 15, 21, and/or 25. In certain embodiments, the amino acid substitution(s) are conservative amino acid substitution (s). In certain embodiments, the amino acid substitutions do not substantially reduce the ability of the antibody to bind antigen. For example, conservative alterations (e.g., conservative substitutions as provided herein) that do not substantially reduce EGFR binding affinity may be made. The binding affinity of anti-EGFR antibody variants can be assessed using methods described in the Examples below.

Conservative substitutions are shown in Table 2 under the heading of "conservative substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved EGFR binding, decreased immunogenicity, or improved ADCC or CDC.

TABLE 2

CONSERVATIVE SUBSTITITIONS

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Non-conservative substitutions will entail exchanging a member of one of these classes for another class. An exemplary substitutional variant is an affinity matured antibody, which may be conveniently generated, e.g., using phage display based affinity maturation techniques such as those described herein. Briefly, one or more CDR residues are mutated and the variant antibodies displayed on phage and screened for a particular biological activity (e.g. binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, the anti-EGFR antibody (or antigen binding fragment thereof) comprises a heavy chain variable domain comprising a CDR-H1 comprising the amino acid sequence N/T/Q-YGVH (SEQ ID NO: 4); a CDR-H2 comprising the amino acid sequence Y-N/A/G/D-T/D/N-P/K/E-FTSRF (SEQ ID NO: 9); and a CDR-H3 comprising the amino acid sequence T/D-Y/L-YDY-E/N-FAY (SEQ ID NO: 14); and a light chain variable domain sequence comprising a CDR-L1 comprising the amino acid sequence I-G/R/S-T/L/P-NIH (SEQ ID NO: 20); a CDR-L2 comprising the amino acid sequence KY-AIG-SE-S/T-I-S/R (SEQ ID NO: 24); and a CDR-L3 comprising the amino acid sequence NWPT-T/L/S/A/Y (SEQ ID NO: 30). In certain embodiments, the anti-EGFR antibody or antigen binding fragment thereof comprises a heavy chain variable domain sequence comprising a CDR-H1 comprising an amino acid sequence selected from consisting of SEQ ID NOs: 1-3; a CDR-H2 comprising an amino acid sequence selected from consisting of SEQ ID NOs: 5-8; and a CDR-H3 comprising an amino acid sequence selected from consisting of SEQ ID NOs: 10-13; and a light chain variable domain sequence comprising a CDR-L1 comprising an amino acid sequence selected from consisting of SEQ ID NOs: 15-19; a CDR-L2 comprising an amino acid sequence selected from consisting of SEQ ID NOs: 21-23, and a CDR-L3 comprising an amino acid sequence selected from consisting of SEQ ID NOs: 25-29. The sequences of the CDRs noted herein are provided in Table 3 below.

TABLE 3

| | |
| --- | --- |
| SEQ ID NO: 1 | NYGVH |
| SEQ ID NO: 2 | QYGVH |
| SEQ ID NO: 3 | TYGVH |
| SEQ ID NO: 4 | N-Q-T-YGVH |
| SEQ ID NO: 5 | YNTPFTSRF |
| SEQ ID NO: 6 | YDDKFTSRF |
| SEQ ID NO: 7 | YATEFTSRF |
| SEQ ID NO: 8 | YGNEFTSRF |
| SEQ ID NO: 9 | Y-N/A/G/D-T/D/N-P/K/E-FTSRF |
| SEQ ID NO: 10 | TYYDYEFAY |
| SEQ ID NO: 11 | DYYDYEFAY |

TABLE 3-continued

| SEQ ID NO: 12 | TYYDYNFAY |
| SEQ ID NO: 13 | TLYDYEFAY |
| SEQ ID NO: 14 | T/D-Y/L-YDY-E/N-FAY |
| SEQ ID NO: 15 | IGTNIH |
| SEQ ID NO: 16 | IRTNIH |
| SEQ ID NO: 17 | IGLNIH |
| SEQ ID NO: 18 | IGPNIH |
| SEQ ID NO: 19 | ISTNIH |
| SEQ ID NO: 20 | I-G/R/S-T/L/P-NIH |
| SEQ ID NO: 21 | KYASESIS |
| SEQ ID NO: 22 | KYGSESIS |
| SEQ ID NO: 23 | KYASETIR |
| SEQ ID NO: 24 | KY-A/G-SE-S/T-I-S/R |
| SEQ ID NO: 25 | NWPTT |
| SEQ ID NO: 26 | NWPTL |
| SEQ ID NO: 27 | NWPTS |
| SEQ ID NO: 28 | NWPTA |
| SEQ ID NO: 29 | NWPTY |
| SEQ ID NO: 30 | NWPT-T/L/S/A/Y |

In certain embodiments, the anti-EGFR antibody (or antigen binding fragment thereof) comprises a heavy chain variable domain sequence comprising a CDR-H1 comprising the amino acid sequence NYGVH (SEQ ID NO: 1); a CDR-H2 comprising the amino acid sequence YNTPFTSRF (SEQ ID NO: 5); and a CDR-H3 comprising the amino acid sequence TYYDYEFAY (SEQ ID NO: 10); and a light chain variable domain sequence comprising a CDR-L1 comprising the amino acid sequence IGTNIH (SEQ ID NO: 15); a CDR-L2 comprising the amino acid sequence KYASESIS (SEQ ID NO: 21); and (3) a CDR-L3 comprising the amino acid sequence NWPTT (SEQ ID NO: 25).

In certain embodiments, the anti-EGFR antibody or antigen binding fragment thereof comprises a heavy chain variable domain sequence comprising a CDR-H1 comprising the amino acid sequence NYGVH (SEQ ID NO: 1); a CDR-H2 comprising the amino acid sequence YNTPFTSRF (SEQ ID NO: 5); and a CDR-H3 comprising the amino acid sequence DYYDYEFAY (SEQ ID NO: 11); and a light chain variable domain sequence comprising a CDR-L1 comprising the amino acid sequence IGTNIH (SEQ ID NO: 15); a CDR-L2 comprising the amino acid sequence KYASESIS (SEQ ID NO: 21); and a CDR-L3 comprising the amino acid sequence NWPTS (SEQ ID NO: 27).

In certain embodiments, the anti-EGFR antibody or antigen binding fragment thereof comprises a heavy chain variable domain sequence comprising a CDR-H1 comprising the amino acid sequence NYGVH (SEQ ID NO: 1); a CDR-H2 comprising the amino acid sequence YGNEFTSRF (SEQ ID NO: 8); and a CDR-H3 comprising the amino acid sequence DYYDYEFAY (SEQ ID NO: 11); and a light chain variable domain sequence comprising a CDR-L1 comprising the amino acid sequence IGTNIH (SEQ ID NO: 15); a CDR-L2 comprising the amino acid sequence KYASESIS (SEQ ID NO: 21); and (a CDR-L3 comprising the amino acid sequence NWPTS (SEQ ID NO: 27).

In certain embodiments, the anti-EGFR antibody or antigen binding fragment thereof comprises a heavy chain variable domain sequence comprising a CDR-H1 comprising the amino acid sequence NYGVH (SEQ ID NO: 1); a CDR-H2 comprising the amino acid sequence YATEFTSRF (SEQ ID NO: 7); and a CDR-H3 comprising the amino acid sequence DYYDYEFAY (SEQ ID NO: 11); and a light chain variable domain sequence comprising a CDR-L1 comprising the amino acid sequence IGTNIH (SEQ ID NO: 15); a CDR-L2 comprising the amino acid sequence KYASESIS (SEQ ID NO: 21); and a CDR-L3 comprising the amino acid sequence NWPTS (SEQ ID NO: 27).

In certain embodiments, the anti-EGFR antibody or antigen binding fragment thereof comprises a heavy chain variable domain sequence comprising a CDR-H1 comprising the amino acid sequence NYGVH (SEQ ID NO: 1); a CDR-H2 comprising the amino acid sequence YDDKFTSRF (SEQ ID NO: 6); and a CDR-H3 comprising the amino acid sequence DYYDYEFAY (SEQ ID NO: 11); and a light chain variable domain sequence comprising a CDR-L1 comprising the amino acid sequence IGTNIH (SEQ ID NO: 15); a CDR-L2 comprising the amino acid sequence KYASESIS (SEQ ID NO: 21); and a CDR-L3 comprising the amino acid sequence NWPTS (SEQ ID NO: 27).

In certain embodiments, the anti-EGFR antibody or antigen binding fragment thereof comprises a heavy chain variable domain sequence comprising a CDR-H1 comprising the amino acid sequence TYGVH (SEQ ID NO: 3); a CDR-H2 comprising the amino acid sequence YGNEFTSRF (SEQ ID NO: 8); and a CDR-H3 comprising the amino acid sequence DYYDYEFAY (SEQ ID NO: 11); and a light chain variable domain sequence comprising a CDR-L1 comprising the amino acid sequence IRTNIH (SEQ ID NO: 16); a CDR-L2 comprising the amino acid sequence KYGSESIS (SEQ ID NO: 22); and a CDR-L3 comprising the amino acid sequence NWPTS (SEQ ID NO: 27).

In certain embodiments, the anti-EGFR antibody or antigen binding fragment thereof comprises a heavy chain variable domain sequence comprising a CDR-H1 comprising the amino acid sequence TYGVH (SEQ ID NO: 3); a CDR-H2 comprising the amino acid sequence YGNEFTSRF (SEQ ID NO: 8); and a CDR-H3 comprising the amino acid sequence DYYDYEFAY (SEQ ID NO: 11); and a light chain variable domain sequence comprising a CDR-L1 comprising the amino acid sequence ISTNIH (SEQ ID NO: 19); a CDR-L2 comprising the amino acid sequence KYGSESIS (SEQ ID NO: 22); and a CDR-L3 comprising the amino acid sequence NWPTS (SEQ ID NO: 27).

In certain embodiments, the anti-EGFR antibody comprises a light chain variable domain ($V_L$) comprising an amino acid sequence set forth in any one of SEQ ID NOs: 32-35. In certain embodiments, the anti-EGFR antibody comprises a heavy chain variable domain ($V_H$) comprising an amino acid sequence set forth in SEQ ID NO: 36-39. The amino acid sequences of SEQ ID NOs: 32-39 are provided below.

SEQ ID NO: 32
EIVLTQSPATLSLSPGERATLSCRASQSIGTNIHWYQQKPGQAPRLLIKY
ASESISGIPARFSGSGSGTDFTLTISSLEPEDFAVYYCQQNNNWPTSFGG
GTKVEIKRT

SEQ ID NO: 33
EIVLTQSPATLSLSPGERATLSCRASQSIRTNIHWYQQKPGQAPRLLIKY
GSESISGIPARFSGSGSGTDFTLTISSLEPEDFAVYYCQQNNNWPTSFGG
GTKVEIKRT

SEQ ID NO: 34
EIVLTQSPATLSLSPGERATLSCRASQSISTNIHWYQQKPGQAPRLLIKY
GSESISGIPARFSGSGSGTDFTLTISSLEPEDFAVYYCQQNNNWPTSFGG
GTKVEIKRT

SEQ ID NO: 35
EIVLTQSPATLSLSPGERATLSCRASQSIGTNIHWYQQKPGQAPRLLIKY
ASESISGIPARFSGSGSGTDFTLTISSLEPEDFAVYYCQQNNNWPTTFGG
GTKVEIKRT

SEQ ID NO: 36
EVQLVESGGGLVQPGGSLRLSCAASGFSLTTYGVHWVRQAPGKGLEWLGV
IWSGGNTDYGNEFTSRFTISRDNAKNSLYLQMNSLRAEDTAVYYCARALD
YYDYEFAYWGQGTMVTVSSA

SEQ ID NO: 37
EVQLVESGGGLVQPGGSLRLSCAASGFSLTNYGVHWVRQAPGKGLEWLGV
IWSGGNTDYGNEFTSRFTISRDNAKNSLYLQMNSLRAEDTAVYYCARALD
YYDYEFAYWGQGTMVTVSSA

SEQ ID NO: 38
EVQLVESGGGLVQPGGSLRLSCAASGFSLTNYGVHWVRQAPGKGLEWLGV
IWSGGNTDYATEFTSRFTISRDNAKNSLYLQMNSLRAEDTAVYYCARALD
YYDYEFAYWGQGTMVTVSSA

SEQ ID NO: 39
EVQLVESGGGLVQPGGSLRLSCAASGFSLTNYGVHWVRQAPGKGLEWLGV
IWSGGNTDYNTPFTSRFTISRDNAKNSLYLQMNSLRAEDTAVYYCARALT
YYDYEFAYWGQGTMVTVSSA

In certain embodiments, the anti-EGFR antibody or antigen binding fragment thereof comprises a light chain variable domain comprising the amino acid sequence set forth in SEQ ID NO: 32 and a heavy chain variable domain comprising the amino acid sequence set forth in SEQ ID NO: 38. In certain embodiments, the anti-EGFR antibody or antigen binding fragment thereof comprises a light chain variable domain comprising the amino acid sequence set forth in SEQ ID NO: 32 and a heavy chain variable domain comprising the amino acid sequence set forth in SEQ ID NO: 37. In certain embodiments, the anti-EGFR antibody or antigen binding fragment thereof comprises a light chain variable domain comprising the amino acid sequence set forth in SEQ ID NO: 33 and a heavy chain variable domain comprising the amino acid sequence set forth in SEQ ID NO: 36. In certain embodiments, the anti-EGFR antibody or antigen binding fragment thereof comprises a light chain variable domain comprising the amino acid sequence set forth in SEQ ID NO: 34 and a heavy chain variable domain comprising the amino acid sequence set forth in SEQ ID NO: 36. In certain embodiments, the anti-EGFR antibody or antigen binding fragment thereof comprises a light chain variable domain comprising the amino acid sequence set forth in SEQ ID NO: 35 and a heavy chain variable domain comprising the amino acid sequence set forth in SEQ ID NO: 39.

The heavy and light chain variable domains are combined in all possible pair-wise combinations to generate a number of anti-EGFR antibodies.

In certain embodiments, the anti-EGFR antibody lacks an N-glycosylation motif in CDR-H2 (an "aglycosylated CDR-H2 anti-EGFR antibody"). Glycosylation in the heavy chain or light chain variable region of a therapeutic antibody, such as the N-glycan at Asn 99 of the $V_H$ region or ERBITUX®, can cause differences within a batch of antibodies that may result in altered function, immunogenicity, or stability.

In certain embodiments, the aglycosylated CDR-H2 anti-EGFR antibody comprises a heavy chain variable domain comprising a CDR-H2 comprising the amino acid sequence Y-A/G/D-D/N-K/E-FTSRF (SEQ ID NO: 31). In certain embodiments, the aglycosylated CDR-H2 anti-EGFR antibody or antigen binding fragment thereof further comprises a heavy chain comprising a CDR-H1 comprising the amino acid sequence N/T/Q-YGVH (SEQ ID NO: 4) and a CDR-H3 comprising the amino acid sequence T/D-Y/L-YDY-E/N-FAY (SEQ ID NO: 14). In certain embodiments, the aglycosylated CDR-H2 anti-EGFR antibody or antigen binding fragment thereof further comprises a light chain variable domain sequence comprising a CDR-L1 comprising the amino acid sequence I-G/R/S-T/L/P-NIH (SEQ ID NO: 20); a CDR-L2 comprising the amino acid sequence KY-A/G-SE-S/T-I-S/R (SEQ ID NO: 24); and a CDR-L3 comprising the amino acid sequence NWPT-T/L/S/A/Y (SEQ ID NO: 30). The sequences of the CDRs described above are provided in Table 4 below.

TABLE 4

| SEQ ID NO: 4 | N/T/Q-YGVH |
|---|---|
| SEQ ID NO: 14 | T/D-Y/L-YDY-E/N-FAY |
| SEQ ID NO: 20 | I-G/R/S-T/L/P-NIH |
| SEQ ID NO: 24 | KY-A/G-SE-S/T-I-S/R |
| SEQ ID NO: 30 | NWPT-T/L/S/A/Y |
| SEQ ID NO: 31 | Y-A/G/D-D/N-K/E-FTSRF |

Methods of analyzing antibody glycosylation include, but are not limited to, e.g., chromatography (such as cation exchange chromatography (CEX) or liquid chromatography), mass spectrometry (such as electrospray ionization mass spectrometry), and capillary electrophoresis-sodium dodecyl sulfate. Such methods are described in, e.g., Jung et al. (2011) *Curr Op Biotechnol.* 22(6):858-67; Cummings R D, Etzler M E. Antibodies and Lectins in Glycan Analysis. In: Varki A, Cummings R D, Esko J D, et al., editors. Essentials of Glycobiology. 2nd edition. Cold Spring Harbor (NY): Cold Spring Harbor Laboratory Press; 2009. Chapter 45; Mulloy B, Hart G W, Stanley P. Structural Analysis of Glycans. In: Varki A, Cummings R D, Esko J D, et al., editors. Essentials of Glycobiology. 2nd edition. Cold Spring Harbor (N.Y.): Cold Spring Harbor Laboratory Press; 2009. Chapter 47; Leymarie, et al. (2012) *Anal Chem.* 84(7): 3040-3048; Fernandez (2005) *European Biopharmaceutical Review.* pp 106-110; and Raju, T. (2013) Methods Mol Biol. 988: 169-180.

In certain embodiments, the anti-EGFR antibody has a stronger binding affinity for an EGFR than it has for a homologue of that EGFR, such as Her2/ERBb2, Her3/ERBb3, or Her4/ERBb4. Normally, the anti-EGFR antibody "binds specifically" to EGFR (i.e., has a binding affinity (Kd) value of no more than about $1\times10^{-7}$ M, preferably no more than about $1\times10^{-8}$ and most preferably no more than about $1\times10^{-9}$ M) but has a binding affinity for a member of the ERBb family which is at least about 50 fold, or at least about 500 fold, or at least about 1000 fold weaker than its binding affinity for EGFR. The anti-EGFR antibody that binds specifically to EGFR can be of any of the various types of antibodies as defined above, but preferably is a humanized or human antibody.

In some embodiments, the extent of binding of the anti-EGFR antibody to a non-target protein (such as Her2/ERBb2, Her3/ERBb3, or Her4/ERBb4) is less than about 10% of the binding of the antibody to EGFR as determined by methods known in the art, such as ELISA, fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., such as an anti-EGFR antibody described herein). In some embodiments, the anti-EGFR antibody exhibits similar antibody-dependent cell-mediated cytotoxicity (ADCC) effector function as ERBITUX®, as demonstrated by, e.g., assays described in the Example. For example, in certain embodiments, ADCC effector function activity of an anti-EGFR antibody described herein is at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, or more than 100% (e.g., about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, or about 130%) of the ADCC effector function activity of ERBITUX®, including any range between these values. In certain embodiments, the anti-EGFR antibody exhibits similar binding affinity for FcγRIIIa as ERBITUX®. In certain embodiments, binding to FcγRIIIa is demonstrated by ELISA, as described in the Examples. For example, the binding affinity of the anti-EGFR for FcγRIIIa is about 1%, about 5%, about 10%, about 15%, about 20%, about 30%, about 40%, about 50%, about 60%, about 70%, about 80%, about 90%, about 95% about 96%, about 97%, about 98%, about 99%, about 100%, or more than 100% higher (e.g., about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, or more than about 125%) than the binding affinity of ERBITUX® (cetuximab) for FcγRIIIa.

In certain embodiments, the anti-EGFR antibody binds a human EGFR with a Kd between about 0.1 pM to 200 pM (0.2 nM), e.g., about 0.1 pM, about 0.25 pM, about 0.5 pM, about 0.75 pM, about 1 pM, about 5 pM, about 10p M, about 20 pM, about 30 pM, about 40 pM, about 50 pM, about 60 pM, about 70 pM, about 80 pM, about 90 pM, about 100 pM, about 110 pM, about 120 pM, about 130 pM, about 140 pM, about 150 pM, about 160 pM, about 170 pM, about 180 pM, about 190 pM, or more than about 190 pM, including any range between these values. In certain embodiments the binding affinity of the anti-EGFR antibody to EGFR is about 1%, about 5%, about 10%, about 15%, about 20%, about 30%, about 40%, about 50%, about 60%, about 70%, about 80%, about 90%, about 95% about 96%, about 97%, about 98%, about 99%, about 100%, or more than about 100% higher (e.g., about 105%, about 110%, about 120%, or about 130%) higher than the binding affinity of ERBITUX® (cetuximab) to EGFR. In certain embodiments, the binding affinity of the anti-EGFR to EGFR is about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.25-fold, about 2.5-fold, about 2.75 fold, about 3-fold, about 3.25-fold, about 3.5 fold, about 3.75-fold, about 4-fold, about 4.25-fold, about 4.5-fold, about 4.75-fold, or more than about 4.75 fold higher than the binding affinity of ERBITUX® (cetuximab) to EGFR, including any range in between these values.

In certain embodiments, the anti-EGFR antibodies provided herein have prolonged in vivo half-lives as compared to ERBITUX®. In certain embodiments, the in vivo half-life of an anti-EGFR antibody described herein is no shorter than the in vivo half-life of ERBITUX®.

In certain embodiments, the anti-EGFR antibodies provided herein exhibit pharmacokinetic properties that are similar to those of ERBITUX® (cetuximab) or its biosimilar. In certain embodiments, the anti-EGFR antibodies provided herein exhibit an AUC (area under curve) that is about 50%, about 55%, about 60%, about 65%, about 70%, about 75%, about 80%, about 85%, about 90%, about 95%, or greater than 95% (such as about 96%, about 97%, about 98%, about 99%, or more than about 99%) of the serum concentration-time profiles of ERBITUX® (cetuximab) or its biosimilar, including any range between these values.

In certain embodiments, the antibody comprises an Fc sequence of a human IgG, e.g., human IgG1 or human IgG4. In certain embodiments, the Fc sequence has been altered or otherwise changed so that it that lacks antibody dependent cellular cytotoxicity (ADCC) effector function, often related to their binding to Fc receptors (FcRs). There are many examples of changes or mutations to Fc sequences that can alter effector function. For example, WO 00/42072 and Shields et al. *J Biol. Chem.* 9(2): 6591-6604 (2001) describes antibody variants with improved or diminished binding to FcRs. The contents of those publications are specifically incorporated herein by reference. The antibody can be in the form of a Fab, Fab', a F(ab)'2, single-chain Fv (scFv), an Fv fragment; a diabody and a linear antibody. Also, the antibody can be a multispecific antibody that binds to EGFR, but also binds one or more other targets and inhibits their function. The antibody can be conjugated to a therapeutic agent (e.g., cytotoxic agent, a radioisotope and a chemotherapeutic agent) or a label for detecting EGFR in patient samples or in vivo by imaging (e.g., radioisotope, fluorescent dye and enzyme). Other modifications include the conjugation of toxins to anti-EGFR antibodies provided herein.

Nucleic acid molecules encoding the anti-EGFR antibodies, expression vectors comprising nucleic acid molecules encoding the CDRs and/or a heavy chain variable domain and/or a light chain variable domain described herein, and cells comprising the nucleic acid molecules are also contemplated. These antibodies can be used in the therapies described herein and to detect EGFR protein in patient samples (e.g., via FACS, immunohistochemistry (IHC), ELISA assays) or in patients.

Monoclonal Antibodies

Monoclonal antibodies can be prepared, e.g., using hybridoma methods, such as those described by Kohler and Milstein, *Nature*, 256:495 (1975) or can be made by recombinant DNA methods (U.S. Pat. No. 4,816,567) or can be produced by the methods described herein in the Examples below. In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro.

The immunizing agent will typically include a polypeptide or a fusion protein of the protein of interest or a composition comprising the protein. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, MONOCLONAL ANTIBODIES: PRINCIPLES AND PRACTICE (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.*, 133:3001 (1984); Brodeur et al. MONOCLONAL ANTIBODY PRODUCTION TECHNIQUES AND APPLICATIONS (Marcel Dekker, Inc.: New York, 1987) pp. 51-63.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies provided herein can be readily isolated and sequenced using conventional procedures (e.g., by using oligonucleotide probes that are capable of binding specifically to genes encoding the heavy and light chains of murine antibodies). The hybridoma cells provided herein serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains in place of the homologous murine sequences (U.S. Pat. No. 4,816,567; Morrison et al., supra) or by covalently joining to the immunoglobulin coding sequence all or part of the coding sequence for a nonimmunoglobulin polypeptide. Such a non-immunoglobulin polypeptide can be substituted for the constant domains of an antibody provided herein, or can be substituted for the variable domains of one antigen-combining site of an antibody provided herein to create a chimeric bivalent antibody.

In certain embodiments, an anti-EGFR antibody provided by the invention is expressed by a stable mammalian cell line. In certain embodiments, an anti-EGFR antibody provided by the invention is expressed from a stable mammalian cell line at a titer of about 2.0 grams/liter, about 2.5 grams/liter, about 3.0 grams/liter, about 3.5 grams/liter, about 4.0 grams/liter, about 4.5 grams/liter, about 5.0 grams/liter, about 5.5 grams/liter, about 6 grams/liter, about 6.5 grams/liter, about 7.0 grams/liter, or more than about 7.0 grams/liter, including any range in between these values. In certain embodiments, the stable mammalian cell line from which an anti-EGFR antibody provided by the invention is expressed is a CHO cell line.

In certain embodiments, the antibodies are monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using, but not limited to, techniques known in the art.

Human and Humanized Antibodies

The antibodies can be humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) that typically contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin. Jones et al. *Nature*, 321: 522-525 (1986); Riechmann et al., *Nature*, 332: 323-329 (1988); Presta, *Curr. Op. Struct. Biol.*, 2:593-596 (1992).

Generally, a humanized antibody has one or more amino acid residues introduced into it from a source that is non-human. These non-human amino acid residues are often referred to as "import" residues, which are typically taken from an "import" variable domain. According to one embodiment, humanization can be essentially performed following the method of Winter and co-workers (Jones et al. *Nature*, 321: 522-525 (1986); Riechmann et al. *Nature*, 332: 323-327 (1988); Verhoeyen et al. *Science*, 239: 1534-1536 (1988)), by substituting rodent CDRs or CDR sequences for the corresponding sequences of a human antibody. Accordingly, such "humanized" antibodies are antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al. *PNAS USA*, 90:2551 (1993); Jakobovits et al., *Nature*, 362:255-258 (1993); Bruggemann et al. *Year in Immunol.*, 7:33 (1993); U.S. Pat. Nos. 5,545, 806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661,016, and Marks et al., *Bio/Technology*, 10: 779-783 (1992); Lonberg et al., *Nature*, 368: 856-859 (1994); Morrison, *Nature*, 368: 812-813 (1994); Fishwild et al. *Nature Biotechnology*, 14: 845-851 (1996); Neuberger, *Nature Biotechnology*, 14: 826 (1996); Lonberg and Huszar, *Intern. Rev. Immunol.*, 13: 65-93 (1995).

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to one embodiment of this technique, antibody V domain sequences are cloned in frame into either a major or minor coat protein gene of a filamentous bacteriophage, such as M13 or fd, and displayed as functional antibody fragments on the surface of the phage particle. Phage display can be performed in a variety of formats, e.g., as described below in the Examples section or as reviewed in, e.g., Johnson, Kevin S. and Chiswell, David J., *Current Opinion in Structural Biology* 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks eta!., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human antibodies can also be produced using various techniques known in the art, including phage display libraries. Hoogenboom and Winter, *J. Mol. Biol.*, 227: 381 (1991); Marks et al., *J. Mol. Biol.*, 222: 581 (1991). The techniques of Cole et al. and Boerner et al. are also available for the preparation of human monoclonal antibodies. Cole et al., *Monoclonal Antibodies and Cancer Therapy*, Alan R. Liss, p. 77 (1985) and Boerner et al., *J. Immunol.*, 147(1): 86-95 (1991).

Multispecific Antibodies

Multispecific antibodies are monoclonal, preferably human or humanized, antibodies that have binding specificities for two or more different antigens (e.g., bispecific antibodies have binding specificities for at least two antigens). For example, one of the binding specificities can be for the a5~1 protein, the other one can be for any other antigen. According to one preferred embodiment, the other antigen is a cell-surface protein or receptor or receptor subunit. For example, the cell-surface protein can be a natural killer (NK) cell receptor. Thus, according to one embodiment, a bispecific antibody of this invention can bind both EGFR and, e.g., a second cell surface receptor.

Suitable methods for making bispecific antibodies are well known in the art. For example, the recombinant production of bispecific antibodies is based on the co-expression of two immunoglobulin heavy-chain/light-chain pairs, where the two heavy chains have different specificities. Milstein and Cuello, *Nature*, 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., *EMBO*, 10: 3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH 1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology*, 121: 210 (1986).

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *PNAS USA*, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Heteroconjugate Antibodies

Heteroconjugate antibodies are composed of two covalently joined antibodies. Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody provided herein with respect to effector function, so as to enhance, e.g., the effectiveness of the antibody in treating cancer. For example, cysteine residue(s) can be introduced into the Fc region, thereby allowing inter-chain disulfide bond formation in this region. The homodimeric antibody thus generated can have improved internalization capability and/or increased complement-mediated cell killing and antibody-dependent cellular cytotoxicity (ADCC). See, Caron et al., *J. Exp. Med.*, 176: 1191-1195 (1992) and Shapes, *J. Immunol.*, 148: 2918-2922 (1992). Homodimeric antibodies with enhanced anti-tumor activity can also be prepared using heterobifunctional cross-linkers as described in Wolff etal., *Cancer Research*, 53: 2560-2565 (1993). Alternatively, an antibody can be engineered that has dual Fc regions and can thereby have enhanced complement lysis and ADCC capabilities. See, Stevenson et al., *Anti-Cancer Drug Design* 3: 219-230 (1989).

Mutations or alterations in the Fc region sequences can be made to improve FcR binding (e.g., FcγR, FcRn). According to one embodiment, an antibody of this invention has at least one altered effector function selected from the group consisting of ADCC, CDC, and improved FcRn binding compared to a native IgG or a parent antibody. Examples of several useful specific mutations are described in, e.g., Shields, R L et al. (2001) *JBC* 276(6)6591-6604; Presta, L. G., (2002) *Biochemical Society Transactions* 30(4):487-490; and WO 00/42072.

According to one embodiment, the Fc receptor mutation is a substitution at least one position selected from the group consisting of: 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438 or 439 of the Fc region, wherein the numbering of the residues in the Fc region is according to the EU numbering system. In some embodiments, the Fc receptor mutation is a D265A substitution. In some embodiments, the Fc receptor mutation is a N297 A substitution. Additional suitable mutations are set forth in U.S. Pat. No. 7,332,581.

In certain embodiments, an anti-EGFR antibody provided herein is afucosylated (i.e., an "afucosylated anti-EGFR antibody" or a "non-fucosylated anti-EGFR antibody"). "Afucosylated antibody" or "nonfucosylated antibody" refers to an antibody of IgG1 or IgG3 isotype with an altered pattern of glycosylation in the Fc region at Asn297 having a reduced level of fucose residues. Glycosylation of human IgG1 or IgG3 occurs at Asn297 as core fucosylated bianntennaiy complex oligosaccharide glycosylation terminated with up to 2 Gal residues. These structures are designated as GO, G1 (a1,6 or a1,3) or G2 glycan residues, depending from the amount of terminal Gal residues (Raju, T. S. BioProcess Int. 1 (2003) 44-53), CHO type glycosylation of antibody Fe parts is e.g. described by Routier, *Glycoconjugate J.* 14 (1997) 201-207. Antibodies which are recombinantly expressed in non glycomodified CHO host cells usually are fucosylated at Asn297 in an amount of at least 85%. In certain embodiments, an afucosylated anti-EGFR antibody provided herein has a reduced level of fucose residues. In certain embodiments, an afucosylated anti-EGFR antibody provided herein has no fucose in its glycosylation pattern. It is commonly known that typical glycosylated residue position in an antibody is the asparagine at position 297 according to the EU numbering system ("Asn297").

Thus, in certain embodiments an afucosylated anti-EGFR antibody provided herein comprises an Fc sequence has been altered or otherwise changed so that it a reduced level of fucose residues or no fucose in its glycosylation pattern. In certain embodiments, an anti-EGFR antibody provided herein comprises an Fc sequence having an alteration at position 297 according to the EU numbering system.

In certain embodiments, an afucosylated anti-EGFR antibody provided herein is produced by a host cell capable of producing hypo- or afucosylated glycans. Stable mammalian host cell lines that can produce afucosylated antibodies have been established and are described in, e.g., Yamane-Ohnuki et al. (2004) *Biotechnol Bioeng.* 87, 614-622; Mori et al. (2004) *Biotechnol Bioeng.* 88, 901-908; Kanda et al (2006) *Biotechnol Bioeng.* 94, 680-688; Kanda (2007) *J Biotechnol.* 130, 300-310; Imai-Nishiya (2007) BMC Biotechnol 7, 84; Yamane-Ohnuki and Satoh (2009) *mAbs* 1, 230-236. In certain embodiments, an afucosylated anti-EGFR antibody provided herein is expressed in a glycomodified host cell engineered to express b(1,4)-N-acetylglucosaminyltransferase III activity. In certain embodiments, an afucosylated anti-EGFR antibody provided herein is expressed in a glycomodified host cell in which 1,6-fucosyltransferase activity has been decreased or eliminated. See, e.g., U.S. Pat. No. 6,946,292 for details regarding the production of glycomodified host cells. The amount of antibody fucosylation can be predetermined e.g. either by fermentation conditions (e.g. fermentation time) or by combination of at least two antibodies with different fucosylation amount. Such afucosylated antibodies and respective glycoengineering methods are described in WO 2005/044859, WO 2004/065540, WO 2007/031875. Umana et al., Nature Biotechnol. 17 (1999) 176-180, WO 99/154342, WO 2005/018572. WO 2006/116260, WO 2006/114700, WO 2005/011735, WO 2005/027966, WO 97/028267, US 2006/0134709, US 2005/0054048, US 2005/0152894, WO 2003/035835, WO 2000/061739. These glycoengineered antibodies have an increased ADCC. Other glycoengineering methods yielding afucosylated antibodies according to the invention are described e.g. in Niwa, R. et al., J. Immunol. Methods 306 (2005) 151-160; Shinkawa, T., et al., J. Biol. Chem, 278 (2003) 3466-3473; WO 03/055993 or US 2005/0249722.

In certain embodiments, an afucosylated anti-EGFR antibody provided herein is produced using in vitro techniques. In certain embodiments, an afucosylated anti-EGFR antibody provided herein is chemically synthesized. (See, e.g., Yamamoto et al. (2008) *JACS* 130, 501-510, which describes the chemical synthesis of a non-fucosylated form of monocyte chemotactic protein 3 (MCP-3). In certain embodiments, an afucosylated anti-EGFR antibody provided herein is produced by using a fucosidase to remove fucose residues on IgGs. (See, e.g., Yazawa et al. (1986) Biochem Biophys Res Commun. 136, 563-569.

In certain embodiments, an afucosylated anti-EGFR antibody provided herein has improved antibody-dependent cell-mediated cytotoxicity (ADCC) effector function compared to ERBITUX®, as demonstrated by, e.g., assays described in the Example. For example, in certain embodiments, ADCC effector function activity of an anti-EGFR antibody described herein is at least about 140%, at least about 150%, at least about 160%, at least about 170%, at least about 180%, at least about 190%, at least about 190%, at least about 200%, at least about 210%, at least about 220%, at least about 230%, at least about 240%, at least about 250%, at least about 260%, at least about 270%, at least about 280%, at least about 290%, or at least about 300% of the ADCC effector function activity of ERBITUX®, including any range between these values. In certain embodiments, ADCC effector function activity of an anti-EGFR antibody described herein is more about 300% of the ADCC effector function activity of ERBITUX®, including at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, at least about 510%, at least about 520%, at least about 530%, at least about 540%, at least about 550%, at least about 560%, at least about 570%, at least about 580%, at least about 590%, or at least about 6000% of the ADCC effector function activity of ERBITUX®, including any range between these values.

In certain embodiments, an afucosylated anti-EGFR antibody provided herein exhibits improved antibody-dependent cell-mediated cytotoxicity (ADCC) effector function than ERBITUX® in a subject having wild-type KRAS. In certain embodiments, an afucosylated anti-EGFR antibody provided herein exhibits improved antibody-dependent cell-mediated cytotoxicity (ADCC) effector function than ERBITUX® in a subject having a KRAS mutation. In certain embodiments, the KRAS mutation is a mutation in codon 12 of the KRAS gene. In certain embodiments, the KRAS mutation is a mutation in codon 13 in the exon 2 of the KRAS gene. In certain embodiments, an afucosylated anti-EGFR antibody provided herein exhibits improved antibody-dependent cell-mediated cytotoxicity (ADCC) effector function than ERBITUX® in a subject having the $KRAS^{G13D}$ mutation. In certain embodiments, the KRAS mutation is a mutation in codon 61 the KRAS gene. In certain embodiments, the KRAS mutation is a mutation in codon 117 of the KRAS gene. In certain embodiments, the KRAS mutation is a mutation in codon 146 of the KRAS gene.

In certain embodiments, an afucosylated anti-EGFR antibody provided herein exhibits improved antibody-dependent cell-mediated cytotoxicity (ADCC) effector function than ERBITUX® in a subject having wild-type BRAF. In certain embodiments, an afucosylated anti-EGFR antibody provided herein exhibits improved antibody-dependent cell-mediated cytotoxicity (ADCC) effector function than ERBITUX® in a subject having a BRAF mutation. In certain embodiments, the BRAF mutation is a mutation in codon 600 of the BRAF gene. In certain embodiments, an afucosylated anti-EGFR antibody provided herein exhibits improved antibody-dependent cell-mediated cytotoxicity (ADCC) effector function than ERBITUX® in a subject having the $BRAF^{V600E}$ mutation. In certain embodiments, the BRAF mutation is a mutation in codon G466 of the BRAF gene. In certain embodiments, the BRAF mutation is a mutation in codon G469 of the BRAF gene. In certain embodiments, the BRAF mutation is a mutation in codon L597 of the BRAF gene.

In certain embodiments, an afucosylated anti-EGFR antibody provided herein exhibits improved antibody-dependent cell-mediated cytotoxicity (ADCC) effector function than ERBITUX® in a subject having wild-type PTEN. In certain embodiments, an afucosylated anti-EGFR antibody provided herein exhibits improved antibody-dependent cell-mediated cytotoxicity (ADCC) effector function than ERBITUX® in a subject having a PTEN mutation. In certain embodiments, the PTEN mutation is a mutation in exon 3 of the PTEN gene. In certain embodiments, the PTEN mutation is a mutation in exon 4 of the PTEN gene. In certain embodiments, the PTEN mutation is a mutation in exon 5 of the PTEN gene. In certain embodiments, the PTEN mutation is a mutation in exon 6 of the PTEN gene. In certain embodiments, the PTEN mutation is a mutation in exon 7 of the PTEN gene. In certain embodiments, the PTEN mutation is a mutation in exon 8 of the PTEN gene. In certain embodiments, the PTEN mutation is a mutation is codon 233 of the PTEN gene.

In certain embodiments, an afucosylated anti-EGFR antibody provided herein exhibits improved antibody-dependent cell-mediated cytotoxicity (ADCC) effector function than ERBITUX® in a subject having wild-type NRAS. In certain embodiments, an afucosylated anti-EGFR antibody provided herein exhibits improved antibody-dependent cell-mediated cytotoxicity (ADCC) effector function than ERBITUX® in a subject having an NRAS mutation. In certain embodiments, the NRAS mutation is a mutation is codon 12 of the NRAS gene. In certain embodiments, the NRAS mutation is a mutation is codon 13 of the NRAS gene. In certain embodiments, the NRAS mutation is a mutation is codon 61 of the NRAS gene.

In certain embodiments, an afucosylated anti-EGFR antibody provided herein exhibits improved antibody-dependent cell-mediated cytotoxicity (ADCC) effector function than ERBITUX® in a subject having wild-type PIK3CA. In certain embodiments, an afucosylated anti-EGFR antibody provided herein exhibits improved antibody-dependent cell-mediated cytotoxicity (ADCC) effector function than ERBITUX® in a subject having a PIK3CA mutation. In certain embodiments, the PIK3CA mutation is a mutation is exon 20 of the PIK3CA gene.

In certain embodiments, the subject to whom an afucosylated anti-EGFR antibody described herein is administered is resistant to Erbitux or its biosimilar. In certain embodiments, the subject to whom an afucosylated anti-EGFR antibody described herein is administered has progressed on Erbitux or its biosimilar. In certain embodiments, the subject to whom an afucosylated anti-EGFR antibody described herein is administered is refractory to Erbitux or its biosimilar.

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Exemplary chemotherapeutic agents useful in the generation of such immunoconjugates include those described elsewhere herein.

In certain embodiments, an anti-EGFR antibody provided herein (such as an aglycosylated CDR-H2 anti-EGFR antibody, an afucosylated anti-EGFR antibody, or an aglycosylated CDR-H2 anti-EGFR antibody that is also afucosylated) is conjugated to maytansine, a maytansinoid, or calicheamicin. In certain embodiments, an anti-EGFR antibody provided herein (such as an aglycosylated CDR-H2 anti-EGFR antibody and/or an afucosylated anti-EGFR antibody) is conjugated to the maytansinoid DM1.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HC1), active esters (such as disuccinimidyl suberate), aldehydes (such as glutaraldehyde), bis-azido compounds (such as bis (p-azidobenzoyl) hexanediamine), bisdiazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In another embodiment, the antibody can be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Covalent Modifications

Covalent modifications of the anti-EGFR antibodies and fragments thereof are included within the scope of this invention. One type of covalent modification includes reacting targeted amino acid residues of a polypeptide with an organic derivatizing agent that is capable of reacting with selected side chains or the N- or C-terminal residues of the polypeptide. Derivatization with bifunctional agents is useful, for instance, for crosslinking the polypeptide to a water-insoluble support matrix or surface for use in the method for purifying antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: *Structure and Molecular Properties*, W. H. Freeman & Co., San Francisco, pp. 79-86 (1983)], acetylation of the N-terminal amine, and amidation of any C-terminal carboxyl group.

Another type of covalent modification of the polypeptide comprises linking the polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

Chimeric Molecules

An anti-EGFR antibody (or fragment thereof) of the present invention can also be modified if advantageous in a way to form a chimeric molecule comprising the polypeptide fused to another, heterologous polypeptide or amino acid sequence (e.g., immunoadhesins or peptibodies).

In one embodiment, such a chimeric molecule comprises a fusion of the polypeptide with a protein transduction domain which targets the polypeptide for delivery to various tissues and more particularly across the brain blood barrier, using, for example, the protein transduction domain of human immunodeficiency virus TAT protein (Schwarze et al., 1999, Science 285: 1569-72).

In another embodiment, such a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag. Various tag polypeptides and their respective antibodies are known in the art. Examples include poly-histidine (poly-His) or poly-histidine-glycine (poly-His-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule can comprise a fusion of the polypeptide with an immunoglobulin or a particular region of an immunoglobulin. For a bivalent form of the chimeric molecule (e.g., an "immunoadhesin"), such a fusion could be to the Fc region of an IgG molecule. Ig fusions of this invention include polypeptides that comprise approximately or only residues 94-243, residues 33-53 or residues 33-52 of human in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also, U.S. Pat. No. 5,428,130 issued Jun. 27, 1995.

Immunoliposomes

The antibodies disclosed herein can also be formulated as immunoliposomes. Liposomes containing the antibody are prepared by methods known in the art, such as described in Epstein et al., *PNAS USA*, 82: 3688 (1985); Hwang et al., *PNAS USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction. An anti-neoplastic agent, a growth inhibitory agent, or a chemotherapeutic agent (such as doxorubicin) is optionally also contained within the liposome. See, Gabizon et al., J. National Cancer Inst., 81(19): 1484 (1989).

Treatment Using Anti-Epidermal Growth Factor Receptor (EGFR) Antibodies

The anti-EGFR antibodies (or fragments thereof) and/or compositions provided herein can be administered to subjects (e.g., mammals such as humans) to treat diseases and disorders involving abnormal EGFR activity, including, for example, cancer (such as head and neck cancer, throat cancer, colorectal cancer, lung cancer, etc.). In certain embodiments, the invention provides anti-EGFR antibodies described herein (or fragments thereof) for use in the manufacture of a medicament for the treatment of cancer (such as head and neck cancer, lung cancer, or colorectal cancer) in a subject. In certain embodiments, the invention provides anti-EGFR antibodies described herein (or fragments thereof) for use in treating cancer (such as head and neck cancer, throat cancer, colorectal cancer, lung cancer, etc.) in a subject. In certain embodiments, the invention provides pharmaceutical compositions comprising an anti-EGFR antibody provided herein (or fragments thereof) for use in treating cancer (such as head and neck cancer, throat cancer, colorectal cancer, lung cancer, etc.) in a subject. In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is a clinical patient, a clinical trial volunteer, an experimental animal, etc. In certain embodiments, the subject is suspected of having or at risk for having a cancer (such as head and neck cancer, throat cancer, colorectal cancer, lung cancer, etc.) or be diagnosed with a cancer or any other disease having abnormal EGFR expression or activity. In some embodiments, the subject to whom an anti-EGFR antibody described herein is administered is wild-type for KRAS. In certain embodiments, the subject to whom an anti-EGFR antibody described herein is administered has the $KRAS^{G13D}$ mutation. In some embodiments, the subject to whom an anti-EGFR antibody described herein is administered is wild-type for BRAF. In certain embodiments, the subject to whom an anti-EGFR antibody described herein is administered has the $BRAF^{V600E}$ mutation. In certain embodiments, the subject to whom an anti-EGFR antibody described herein is administered is resistant to Erbitux or its biosimilar. In certain embodiments, the subject to whom an anti-EGFR antibody described herein is administered has progressed on Erbitux or its biosimilar. In certain embodiments, the subject to whom an anti-EGFR antibody described herein is administered is refractory to Erbitux or its biosimilar.

In certain embodiments, a DM1-conjugated anti-EGFR antibody described herein is administered to a subject having wild-type KRAS. In certain embodiments, a DM1-conjugated anti-EGFR antibody described herein is administered to a cancer patient having the $KRAS^{G13D}$ mutation. In certain embodiments, a DM1-conjugated anti-EGFR antibody described herein is administered to a cancer patient having wild-type BRAF. In certain embodiments, a DM1-conjugated anti-EGFR antibody described herein is administered to a subject having the BRAFV$^{600E}$ mutation. In certain embodiments, a DM1-conjugated anti-EGFR antibody described herein is administered to a subject that is resistant to Erbitux or its biosimilar. In certain embodiments, a DM1-conjugated anti-EGFR antibody described herein is administered to a subject that has progressed on Erbitux or its biosimilar. In certain embodiments, a DM1-conjugated anti-EGFR antibody described herein is administered to a subject that is refractory to Erbitux or its biosimilar.

Many diagnostic methods for cancer (such as head and neck cancer, throat cancer, colorectal cancer, lung cancer, etc.) or any other disease exhibiting abnormal EGFR activity and the clinical delineation of those diseases are known in the art. Such methods include, but are not limited to, e.g., immunohistochemistry, PCR, fluorescent in situ hybridization (FISH). Additional details regarding diagnostic methods for abnormal EGFR activity or expression are described in, e.g., Gupta et al. (2009) *Mod Pathol.* 22(1): 128-133; Lopez-Rios et al. (2013) *J. Clin Pathol.* 66(5): 381-385; Ellison et al. (2013) J Clin Pathol 66(2): 79-89; and Guha et al. (2013) *PLoS ONE* 8(6): e67782.

Administration can be by any suitable route including, e.g., intravenous, intramuscular, or subcutaneous. In some embodiments, the anti-EGFR antibodies (or fragments thereof) and/or compositions provided herein are administered in combination with a second, third, or fourth agent (including, e.g., an antineoplastic agent, a growth inhibitory agent, a cytotoxic agent, or a chemotherapeutic agent) to treat the diseases or disorders involving abnormal EGFR activity. Such agents include, e.g., docetaxel, gefitinib, FOLFIRI (irinotecan, 5-fluorouracil, and leucovorin), irinotecan, cisplatin, carboplatin, paclitaxel, bevacizumab (anti-VEGF antibody), FOLFOX-4 (infusional fluorouracil, leucovorin, and oxaliplatin, afatinib, gemcitabine, capecitabine, pemetrexed, tivantinib, everolimus, CpG-ODN, rapamycin, lenalidomide, vemurafenib, endostatin, lapatinib, PX-866, Imprime PGG, and irlotinibm. In some embodiments, the anti-EGFR antibodies (or fragments thereof) are conjugated to the additional agent.

In certain embodiments, the anti-EGFR antibodies (or fragments thereof) and/or compositions provided herein are administered in combination with one or more additional therapies, such as radiation therapy, surgery, chemotherapy, and/or targeted therapy. In certain embodiments, the anti-EGFR antibodies (or fragments thereof) and/or compositions provided herein are administered in combination with radiation therapy. In certain embodiments, the combination of an anti-EGFR antibody (or fragment thereof) and/or composition provided herein and radiation therapy is used for treating head and neck cancer.

In certain embodiments, the combination of an anti-EGFR antibody (or fragment thereof) and/or composition provided herein and radiation therapy is used for treating throat cancer. In certain embodiments, the combination of an anti-EGFR antibody (or fragment thereof) and/or composition provided herein and radiation therapy is used for treating colorectal cancer. In certain embodiments, the combination of an anti-EGFR antibody (or fragment thereof) and/or composition provided herein and radiation therapy is used for treating lung cancer.

Depending on the indication to be treated and factors relevant to the dosing that a physician of skill in the field would be familiar with, the antibodies provided herein will be administered at a dosage that is efficacious for the treatment of that indication while minimizing toxicity and side effects. For the treatment of a cancer (such as head and neck cancer, throat cancer, colorectal cancer, lung cancer, etc.), a typical dose can be, for example, in the rage of 0.001 to 1000 μg; however, doses below or above this exemplary range are within the scope of the invention. The daily dose can be about 0.1 μg/kg to about 100 mg/kg of total body weight (e.g., about 5 μg/kg, about 10 μg/kg, about 100 μg/kg, about 500 μg/kg, about 1 mg/kg, about 50 mg/kg, or a range defined by any two of the foregoing values), preferably from about 0.3 μg/kg to about 10 mg/kg of total body weight (e.g., about 0.5 μg/kg, about 1 μg/kg, about 50 μg/kg, about 150 μg/kg, about 300 μg/kg, about 750 μg/kg, about 1.5 mg/kg, about 5 mg/kg, or a range defined by any two of the foregoing values), more preferably from about 1 μg/kg to 1 mg/kg of total body weight (e.g., about 3 μg/kg, about 15 μg/kg, about 75 μg/kg, about 300 μg/kg, about 900 μg/kg, or a range defined by any two of the foregoing values), and even more preferably from about 0.5 to 10 mg/kg body weight per day (e.g., about 2 mg/kg, about 4 mg/kg, about 7 mg/kg, about 9 mg/kg, or a range defined by any two of the foregoing values, including any range between the foregoing values). As noted above, therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

A pharmaceutical composition comprising the anti-EGFR antibody can be administered one, two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection The antibody (or antigen-binding fragment thereof) may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgically implanted in various locations.

Cancer treatments can be evaluated by, e.g., but not limited to, tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation $100-(T/C \times 100)$, where T is the mean relative tumor volume of the treated tumor, and C is the mean relative tumor volume of a non-treated tumor. In certain embodiments, the % TGI is about 10%, about 20%, about 30%, about 40%, about 50%, about 60%, about 70%, about 80%, about 90%, about 91%, about 92%, about 93%, about 94%, about 95%, or more than 95%. In certain embodiments the % TGI of an anti-EGFR is the same as or greater than the % TGI of ERBITUX®, such as about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, including any range in between these values, or more than about 2.7-fold greater than the % TGI of ERBITUX®.

Pharmaceutical Formulations

The anti-EGFR antibodies (or fragments thereof) can be formulated with suitable carriers or excipients so that they are suitable for administration. Suitable formulations of the antibodies are obtained by mixing an antibody (or fragment thereof) having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary antibody formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent. Such molecules are suitably present in combination in amounts that are effective for the purpose intended. The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages. The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980). Sustained-release preparations may be prepared. Suitable examples of sustained release preparations include semi-permeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Lipofectins or liposomes can be used to deliver the polypeptides and antibodies (or fragments thereof) or compositions of this invention into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *PNAS USA*, 90: 7889-7893 (1993).

The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's PHARMACEUTICAL SCIENCES, supra.

Sustained-release preparations can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydro gels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In certain embodiments, the formulation comprises an anti-EGFR antibody described herein at a concentration of greater than about 0.5 mg/ml, greater than about 1 mg/ml, greater than about 2 mg/ml, greater than about 3 mg/ml, greater than about 4 mg/ml, greater than about 5 mg/ml, greater than about 6 mg/ml, greater than about 7 mg/ml, greater than about 8 mg/ml, greater than about 9 mg/ml, greater than about 10 mg/ml, greater than about 11 mg/ml, greater than about 12 mg/ml, greater than about 13 mg/ml, greater than about 14 mg/ml, greater than about 15 mg/ml, greater than about 16 mg/ml, greater than about 17 mg/ml, greater than about 18 mg/ml, greater than about 19 mg/ml, greater than about 20 mg/ml, greater than about 21 mg/ml, greater than about 22 mg/ml, greater than about 23 mg/ml, greater than about 24 mg/ml, greater than about 25 mg/ml, greater than about 26 mg/ml, greater than about 27 mg/ml, greater than about 28 mg/ml, greater than about 29 mg/ml, or greater than about 30 mg/ml, including any range in between these values.

In certain embodiments, the anti-EGFR antibody is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising a citrate, NaCl, acetate, succinate, glycine, polysorbate 80 (Tween 80), or any combination of the foregoing. In certain embodiments, the anti-EGFR antibody is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising about 100 mM to about 150 mM glycine. In certain embodiments, the anti-EGFR antibody is formulated in a buffer comprising about 50 mM to about 100 mM NaCl. In certain embodiments, the anti-EGFR antibody is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising about 10 mM to about 50 mM acetate. In certain embodiments, the anti-EGFR antibody is formulated in a buffer comprising about 10 mM to about 50 mM succinate. In certain embodiments, the anti-EGFR antibody is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising about 0.005% to about 0.02% polysorbate 80. In certain embodiments, the anti-EGFR antibody is formulated in a buffer having a pH between about 5.1 and 5.6. In certain embodiments, the anti-EGFR antibody is formulated in a buffer comprising 10 mM citrate, 100 mM NaCl, 100 mM glycine, and 0.01% polysorbate 80, wherein the formulation is at pH=5.5.

In certain embodiments, a formulation (such as a formulation comprising buffer comprising 10 mM citrate, 100 mM NaCl, 100 mM glycine, and 0.01% polysorbate 80, wherein the formulation is at pH=5.5) comprising an EFGR antibody described herein (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) is stable at room temperature (such as at about 20-25° C. for about 0.5 weeks, 1.0 weeks, 1.5 weeks, 2.0 weeks, 2.5 weeks, 3.5 weeks, 4.0 weeks, 4.5 weeks, or 5.0 weeks, including any range in between these values. In certain embodiments, a formulation (such as a formulation comprising buffer comprising 10 mM citrate, 100 mM NaCl, 100 mM glycine, and 0.01% polysorbate 80, wherein the formulation is at pH=5.5) comprising an EFGR antibody described herein (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) is stable under accelerated conditions (such as storage at about 37° C.) for about 0.5 weeks, 1.0 weeks, 1.5 weeks, 2.0 weeks, 2.5 weeks, 3.5 weeks, 4.0 weeks, 4.5 weeks, or 5.0 weeks, including any range in between these values.

Size exclusion chromatography (SEC) is a well-known and widely used method used in protein stability studies to detect potential fragmentation and aggregation, corresponding to physical and chemical instabilities. In certain embodiments, a formulation comprising 5 mg/ml, 10 mg/ml, 15 mg/ml, 20 mg/ml, or 25 mg/ml of an anti-EFGR antibody described herein shows less than about a 1.6%, 1.4%, 1.2%, 1.0%, 0.8%, 0.6%, 0.4%, 0.2%, or 0.1% increase in high molecular weight species (HMWS) after 1 week at 37° C., relative to the initial % high molecular weight species, as measured using SEC, including any range in between these values. In certain embodiments, a formulation comprising 5 mg/ml, 10 mg/ml, 15 mg/ml, 20 mg/ml, or 25 mg/ml of an anti-EFGR antibody described herein shows less than about a 2.0%, 1.8% 1.6%, 1.4%, 1.2%, 1.0%, 0.8%, 0.6%, 0.4%, 0.2%, or 0.1% increase in high molecular weight species after 2 weeks at 37° C., relative to the initial % high molecular weight species, as measured using SEC, including any range in between these values. In certain embodiments, a formulation comprising 5 mg/ml, 10 mg/ml, 15 mg/ml, 20 mg/ml, or 25 mg/ml of an anti-EFGR antibody described herein shows less than about a 3.3%, 3.2%, 3.1%, 3.0%, 2.9%, 2.8%, 2.7%, 2.6%, 2.5%, 2.4%, 2.2%, 2.0%, 1.8% 1.6%, 1.4%, 1.2%, 1.0%, 0.8%, 0.6%, 0.4%, 0.2%, or 0.1% increase in high molecular weight species after 4 weeks at 37° C., relative to the initial % high molecular weight species, as measured using SEC, including any range in between these values.

In certain embodiments, a formulation comprising 5 mg/ml, 10 mg/ml, 15 mg/ml, 20 mg/ml, or 25 mg/ml of an anti-EFGR antibody described herein shows less than about a 1.6%, 1.4%, 1.2%, 1.0%, 0.8%, 0.6%, 0.4%, 0.2%, or 0.1% increase in low molecular weight species (LMWS) after 1 week at 37° C., relative to the initial % low molecular weight species, as measured using SEC, including any range in between these values. In certain embodiments, a formulation comprising 5 mg/ml, 10 mg/ml, 15 mg/ml, 20 mg/ml, or 25 mg/ml of an anti-EFGR antibody described herein shows less than about a 2.0%, 1.8% 1.6%, 1.4%, 1.2%, 1.0%, 0.8%, 0.6%, 0.4%, 0.2%, or 0.1% increase in low molecular weight species after 2 weeks at 37° C., relative to the initial % low molecular weight species, as measured using SEC, including any range in between these values. In certain embodiments, a formulation comprising 5 mg/ml, 10 mg/ml, 15 mg/ml, 20 mg/ml, or 25 mg/ml of an anti-EFGR antibody described herein shows less than about a 2.4%, 2.2%, 2.0%, 1.8% 1.6%, 1.4%, 1.2%, 1.0%, 0.8%, 0.6%, 0.4%, 0.2%, or 0.1% increase in low molecular weight species after 4 weeks at 37° C., relative to the initial % low molecular weight species, as measured using SEC, including any range in between these values.

In certain embodiments, a formulation comprising 5 mg/ml, 10 mg/ml, 15 mg/ml, 20 mg/ml, or 25 mg/ml of an anti-EFGR antibody described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 1 week at 37° C., relative to the initial % monomer, as measured using SEC, including any range in between these values. In certain embodiments, a formulation comprising 5 mg/ml, 10 mg/ml, 15 mg/ml, 20 mg/ml, or 25 mg/ml of an anti-EFGR antibody described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 2 weeks at 37° C., relative to the initial % monomer, as measured using SEC, including any range in between these values. In certain embodiments, a formulation comprising 5 mg/ml, 10 mg/ml, 15 mg/ml, 20 mg/ml, or 25 mg/ml of an anti-EFGR antibody described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 4 weeks at 37° C., relative to the initial % monomer, as measured using SEC, including any range in between these values.

Cation exchange chromatography (CEX) is a well-known and widely used tool to detect protein degradation events such as deamidation or oxidation (Moorhouse et al. (1997) J. Pharm. Biomed. Anal. 16, 593-603). Acidic species are the variants that elute earlier than the main peak from CEX, while basic species are the variants that elute later than the main peak from CEX. In certain embodiments, the acidic peak fraction of a formulation comprising 5 mg/ml, 10 mg/ml, 15 mg/ml, 20 mg/ml, or 25 mg/ml of an anti-EFGR antibody described herein is no more than about 7%, 8%, 9%, 10%, 11%, 12%, 13%, 14%, or 15% of total protein after 1 week at 37° C., as measured using CEX, including any range in between these values. In certain embodiments, the acidic peak fraction of a formulation comprising 5 mg/ml, 10 mg/ml, 15 mg/ml, 20 mg/ml, or 25 mg/ml of an anti-EFGR antibody described herein is no more than about 8%, 9%, 10%, 11%, 12%, 13%, 14%, 15%, 16%, 17%, or 18% of total protein after 2 weeks at 37° C., as measured using CEX, including any range in between these values. In certain embodiments, the acidic peak fraction of a formulation comprising 5 mg/ml, 10 mg/ml, 15 mg/ml, 20 mg/ml, or 25 mg/ml of an anti-EFGR antibody described herein is no more than about 8%, 9%, 10%, 11%, 12%, 13%, 14%, 15%, 16%, 17%, 18%, 19%, 20%, 21%, 22%, 23%, 24%, 25%, 26%, or 27% of total protein after 4 weeks at 37° C., as measured using CEX, including any range in between these values.

In certain embodiments, the basic peak fraction of a formulation comprising 5 mg/ml, 10 mg/ml, 15 mg/ml, 20 mg/ml, or 25 mg/ml of an anti-EFGR antibody described herein is no more than about 39%, 40%, 41%, 42%, 43%, 44%, 45%, or 46% of total protein after 1 week at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-EFGR antibody described herein is no more than about 39%, 40%, 41%, 42%, 43%, 44%, 45%, or 46% of total protein after 2 weeks at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-EFGR antibody described herein is no more than about 39%, 40%, 41%, 42%, 43%, 44%, 45%, or 46% of total protein after 4 weeks at 37° C., as measured using CEX, including any range in between these values.

In certain embodiments, the main peak fraction of a formulation comprising 5 mg/ml, 10 mg/ml, 15 mg/ml, 20 mg/ml, or 25 mg/ml of an anti-EFGR antibody described herein is no less than about 32%, 33%, 34%, 35%, 36%, 37%, 38%, 39%, 40%, 41%, 42%, 43%, 44%, 45%, or 46% of total protein after 1 week at 37° C., as measured using CEX, including any range in between these values. In certain embodiments, the main peak fraction of a formulation comprising 5 mg/ml, 10 mg/ml, 15 mg/ml, 20 mg/ml, or 25 mg/ml of an anti-EFGR antibody described herein is no less than about 32%, 33%, 34%, 35%, 36%, 37%, 38%, 39%, 40%, 41%, 42%, 43%, 44%, 45%, or 46% of total protein after 2 weeks at 37° C., as measured using CEX, including any range in between these values. In certain embodiments, the main peak fraction of a formulation comprising 5 mg/ml, 10 mg/ml, 15 mg/ml, 20 mg/ml, or 25 mg/ml of an anti-EFGR antibody described herein is no less than about 32%, 33%, 34%, 35%, 36%, 37%, 38%, 39%, 40%, 41%, 42%, 43%, 44%, 45%, or 46% of total protein after 4 weeks at 37° C., as measured using CEX, including any range in between these values.

The formulations to be used for in vivo administration must be sterile. This is readily accomplished by, e.g., filtration through sterile filtration membranes.

Methods of Diagnosis and Imaging Using Anti-Epidermal Growth Factor Receptor Antibodies Labeled anti-EGFR antibodies, fragments thereof, and derivatives and analogs thereof, which specifically bind to an EGFR polypeptide can be used for diagnostic purposes to detect, diagnose, or monitor diseases and/or disorders associated with the expression, aberrant expression and/or activity of EGFR. For example, the anti-EGFR antibodies (or fragments thereof) provided herein can be used in in situ, in vivo, ex vivo, and in vitro diagnostic assays or imaging assays. Methods for detecting expression of an EGFR polypeptide, comprising (a) assaying the expression of the polypeptide in cells (e.g., tissue) or body fluid of an individual using one or more antibodies of this invention and (b) comparing the level of gene expression with a standard gene expression level, whereby an increase or decrease in the assayed gene expression level compared to the standard expression level is indicative of aberrant expression.

Additional embodiments provided herein include methods of diagnosing a disease or disorder associated with expression or aberrant expression of EGFR in an animal (e.g., a mammal such as a human). The methods comprise detecting EGFR molecules in the mammal. In certain embodiments, diagnosis comprises: (a) administering an effective amount of a labeled anti-EGFR antibody (or fragment thereof) to a mammal (b) waiting for a time interval following the administering for permitting the labeled anti-EGFR antibody (or fragment thereof) to preferentially concentrate at sites in the subject where the EGFR molecule is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of EGFR. Background level can be determined by various methods including, comparing the amount of labeled molecule detected to a standard value previously determined for a particular system.

Anti-EGFR antibodies (or fragments thereof) provided herein can be used to assay protein levels in a biological sample using classical immunohistological methods known to those of skill in the art (e.g., see Jalkanen, et al., *J. Cell. Biol.* 101:976-985 (1985); Jalkanen, et al., *J. Cell. Biol.* 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I)carbon ($^{14}$C), sulfur $^{35}$S), tritium ($^{3}$H), indium ($^{115m}$In, $^{113m}$In, $^{112}$In, $^{111}$In), and technetium ($^{99}$Tc, $^{99m}$Tc), thallium $^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminol; and fluorescent labels, such as fluorescein and rhodamine, and biotin.

Techniques known in the art may be applied to labeled antibodies (or fragments thereof) provided herein. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003). Alternatively, or additionally, one can measure levels of an EGFR polypeptide-encoding nucleic acid or mRNA in the cell, e.g., via fluorescent in situ hybridization using a nucleic acid based probe corresponding to an EGFR-encoding nucleic acid or the complement thereof; (FISH; see WO98/454 79 published October, 1998), Southern blotting, Northern blotting, or polymerase chain reaction (PCR) techniques, such as real time quantitative PCR (RT-PCR). One can also study EGFR overexpression by measuring shed antigen in a biological fluid such as serum, e.g., using antibody-based assays (see also, e.g., U.S. Pat. No. 4,933,294 issued Jun. 12, 1990; W091/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo and ex vivo assays are available to the skilled practitioner. For example, one can expose cells within the body of the mammal to an antibody which is optionally labeled with a detectable label, e.g., a radioactive isotope, and binding of the antibody to the can be evaluated, e.g., by external scanning for radioactivity or by analyzing a sample (e.g., a biopsy or other biological sample) taken from a mammal previously exposed to the antibody.

Articles of Manufacture and Kits

Another embodiment provided herein is an article of manufacture containing materials useful for the treatment of cancer, such as head and neck cancer, lung cancer, or colorectal cancer (e.g. tumors), or. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating the condition and may have a sterile access port (for example the container may be an intravenous solution bag or a vial having a stopper pierceable by a hypodermic injection needle). At least one active agent in the composition is an anti-EGFR antibody (or fragment thereof) provided herein. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In one embodiment, the package insert indicates that the composition is used for treating cancer (such as head and neck cancer, lung cancer, or colorectal cancer).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for isolation or detection of EGFR in patients, optionally in combination with the articles of manufacture. For isolation and purification of EGFR, the kit can contain an anti-EGFR antibody (or fragment thereof) provided herein coupled to beads (e.g., sepharose beads). Kits can be provided which contain the antibodies (or fragments thereof) for detection and quantitation of EGFR in vitro, e.g. in an ELISA or a Western blot. As with the article of manufacture, the kit comprises a container and a label or package insert on or associated with the container. For example, the container holds a composition comprising at least one anti-EGFR antibody provided herein. Additional containers may be included that contain, e.g., diluents and buffers, control antibodies. The label or package insert may provide a description of the composition as well as instructions for the intended in vitro or diagnostic use.

EXAMPLES

Figure 2:
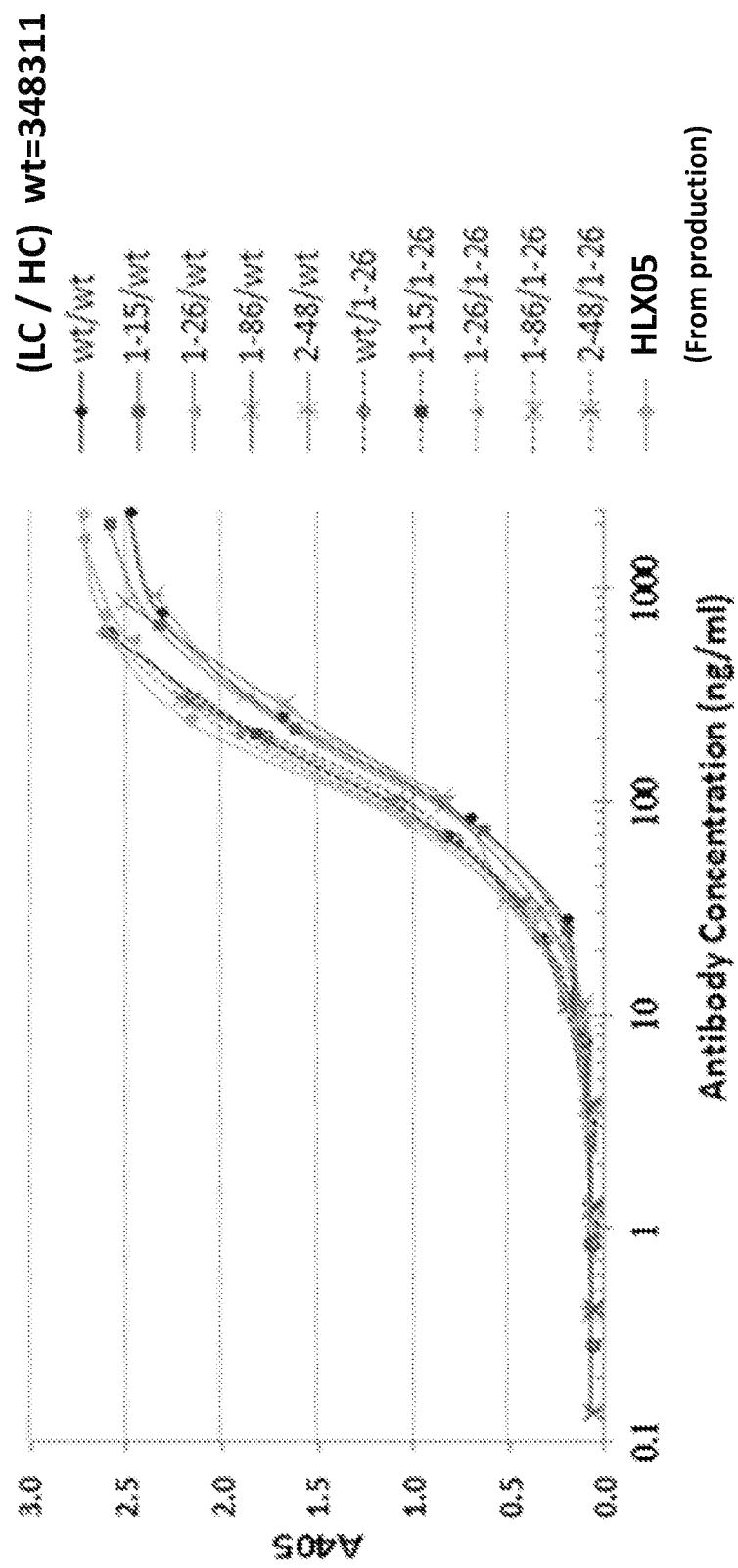
FIG. 2 shows the results of ELISAs performed to compare the binding of full length anti-EGFR IgG antibody variants obtained from a CDR-L3/CDR-H3 library to EGFR.

Example 1. Generation and Affinity Maturation of Glycosylated and Aglycosylated CDR-H2 Anti-Epidermal Growth Factor Antibodies The humanized anti-EGFR antibody 348311 was generated using the germline heavy chain variable region VH3.48 and the germline light chain variable region VK3.11. 348311 was then used in in vitro phage display-based affinity maturation experiments to generate clones with improved binding performance. First, CDR-L3/CDR-H3 nucleic acid libraries were generated via PCR, cloned into a phage display vector, and transformed into E. coli to produce a library of phages. After two rounds of panning, 284 Fab clones were screened via ELISA, and seven clones (i.e., 1-15, 1-16, 1-26, 1-86, 2-48, 1-13, and 3-66) were found to have binding performance that was equivalent to or better than 348311 (FIG. 1). Further ELISAs were performed using full-length IgG clones comprising the following light chain/heavy chain combinations: 348311/348311 (LC/HC), 1-15/348311 (LC/HC), 1-26/348311 (LC/HC), 1-86/348311 (LC/HC), 2-48/348311 (LC/HC), 348311/1-26 (LC/HC), 1-15/1-26 (LC/HC), 1-26/1-26 (LC/HC), 1-86/1-26 (LC/HC), and 2-48/1-26 (LC/HC). HLX05 (i.e., an ERBITUX® biosimilar antibody produced in-house) was also tested. Clones comprising the heavy chain of 1-26 exhibited better binding performance to EGFR than clones comprising the heavy chain of 348311. (See FIG. 2.)

Figure 3:
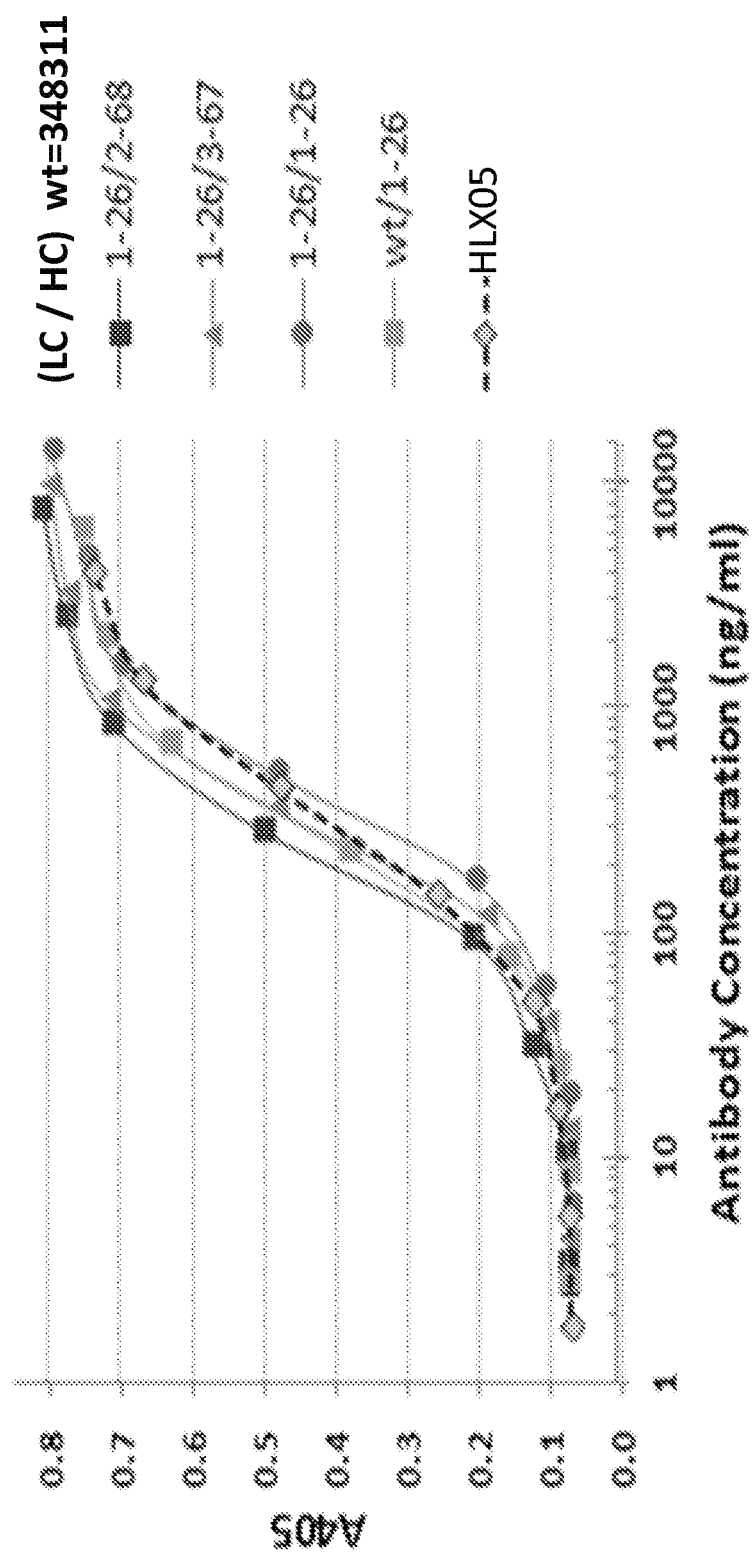
FIG. 3 shows the results of off-rate ELISAs performed to compare the off rates of HLX05 antibody (i.e., an ERBITUX biosimilar antibody produced in-house) and anti-EGFR antibody variants obtained from a CDR-H2 library to EGFR.

The 1-26 heavy chain was selected and used as the basis for generating CDR-H2 libraries for deletion of a glycosylation site. CDR-H2 nucleic acid libraries were generated via PCR, cloned into a phage display vector, and transformed into E. coli to produce a library of phages. After two rounds of panning, two clones, i.e., 2-68 and 3-67, were screened via ELISA and found to have improved binding properties. Off-rate ELISAs were performed in wells coated with EGFR antigen produced in-house, and anti-EGFR antibody clones comprising the following light chain/heavy chain combinations: 1-26/2-68 (LC/HC), 1-26/3-67 (LC/HC), 1-26/1-26 (LC/HC) and 348311/1-26 (LC/HC). Clones comprising 1-26/2-68 (LC/HC), 1-26/3-67 (LC/HC), and 348311/1-26 (LC/HC) were found to have higher affinity of EGFR-binding than the HLX05 in the off-rate ELISA (FIG. 3).

Clone 3-67 was used as the basis to generate CDR-L1/CDR-L2/CDR-H1 libraries. CDR-L1/CDR-L2/CDR-H1 nucleic acid libraries were generated via PCR, cloned into a phage display vector, and transformed into E. coli to produce a library of phages. After 2 rounds of panning, Clones #8, #31, #33, and #34 were screened via ELISA and shown to bind EGFR with an affinity similar to that of ERBITUX®.

Figure 4:
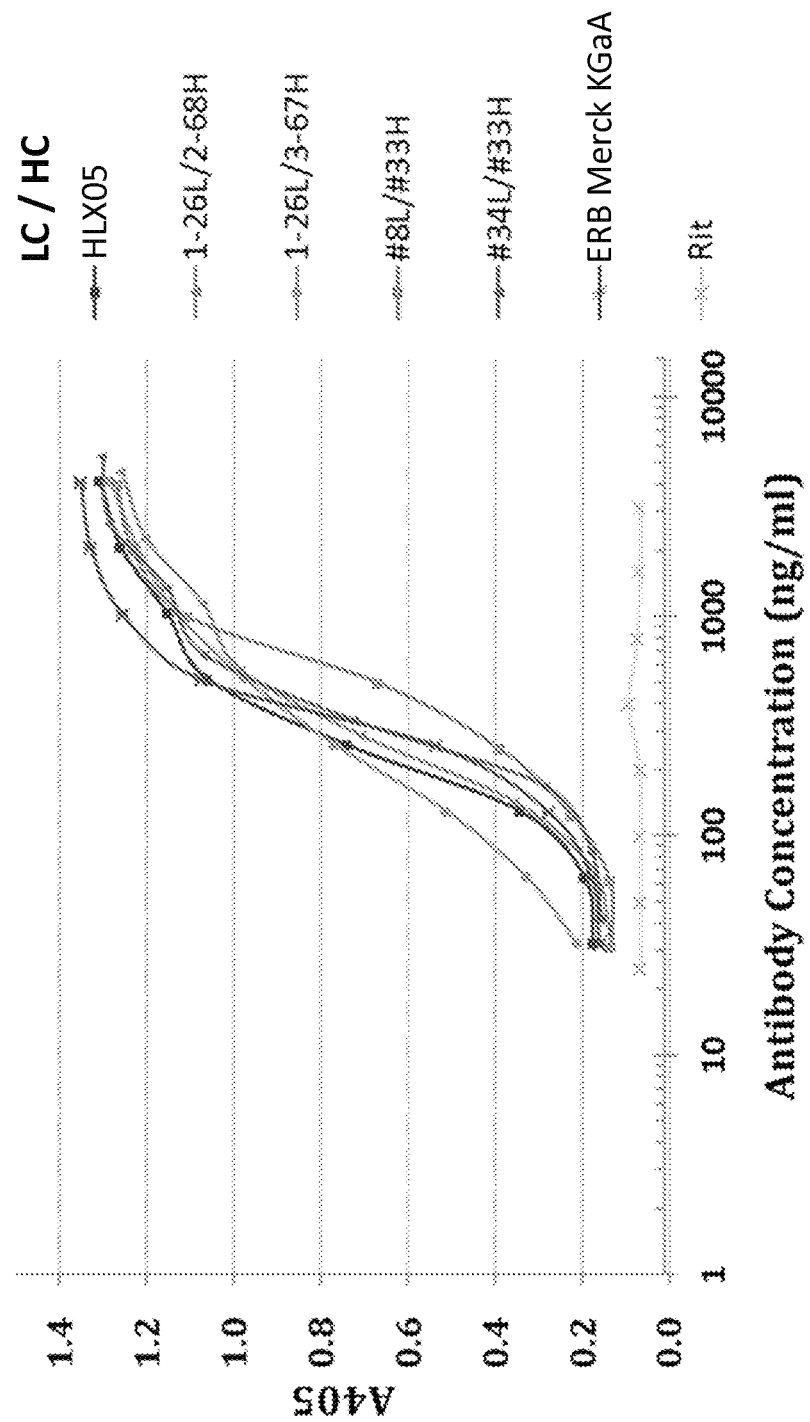
FIG. 4 shows the results of ELISAs performed to compare direct EGFR binding of HLX05 antibody (i.e., an ERBITUX biosimilar antibody produced in-house), ERBITUX® purchased from Merck KGaA, anti-EGFR antibodies 1-26/2-68, 1-26/3-67, #8/#33, #34/#33, and rituximab.

Heavy chains and light chains of clones 1-26, 2-68, 3-67, #8, #31, #33, and #34 were shuffled to generate additional anti-EGFR antibody variants, which were also tested in ELISAs. The following lead antibodies were selected for further analysis in a direct binding ELISA: 1-26/2-68 (LC/HC), 1-26/3-67 (LC/HC), #8/#33 (LC/HC), and #34/#33 (LC/HC). Briefly, serial dilutions of each clone, HLX05, ERBITUX® purchased from Merck KGaA, and rituximab (i.e., an anti-CD20 antibody) were captured with goat anti-fd antibody in wells of a microtiter dish. The amount of captured antibody in each well was quantified using an anti-Human Kappa-HRP-conjugated secondary antibody. The HRP-conjugated secondary antibody was added to the wells, and, following an incubation, excess secondary antibody was washed away. TMB was added to the wells, and following incubation, the reaction was stopped, and HRP activity was measured by monitoring the increase in absorbance at 450 nm. EGFR binding was measured by adding EGFR-AP fusion protein to wells. Following an incubation and wash, pNPP was added to the wells and incubated for 30 minutes. AP activity was measured by monitoring the increase in absorbance at 405 nm. Antibody concentration was plotted as a function of AP activity (FIG. 4). As shown in FIG. 4, clones 1-26/2-68 (LC/HC), 1-26/3-67 (LC/HC) were shown to have binding affinities for EGFR that were similar to HLX05 and ERBITUX® purchased from Merck KGaA.

Figure 5:
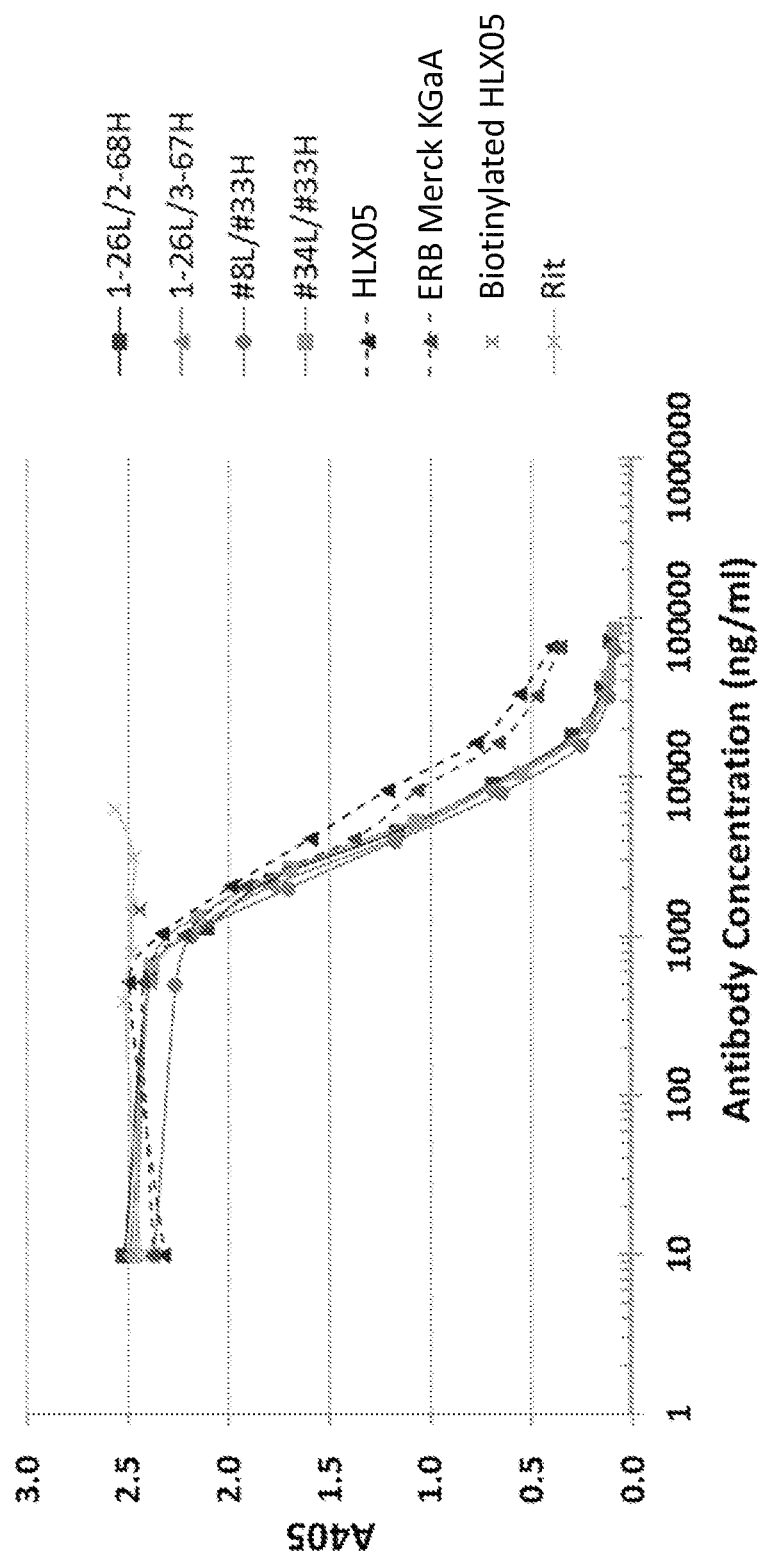
FIG. 5 shows the results of competitive ELISAs performed to compare the EGFR binging of HLX05, ERBITUX®, Rituximab, and anti-EGFR antibodies 1-26/2-68, 1-26/3-67, #8/#33, and #34/#33.

Clones 1-26/2-68 (LC/HC), 1-26/3-67 (LC/HC); #8/#33 (LC/HC), #34/#33 (LC/HC), HLX05, ERBITUX® purchased from Merck KGaA, and rituximab were tested in a competitive ELISA for EGFR binding with biotinylated HLX05. Briefly, a sample of each antibody was pre-mixed with biotinylated HLX05. Alkaline phosphatase-conjugated EGFR was then added to the pre-mixed solution and pre-incubated for 1 hour at room temperature. The preincubation mix was then added to mictotiter wells coated with avidin. Following a one-hour incubation, all wells were washed with PBST, and pNPP was added to each well. Following a second incubation at 37° C., the reaction was stopped. Alkaline phosphatase activity was measured by monitoring the increase in absorbance at 405 nm. All clones tested showed higher competing capability than either HLX05 or ERBITUX® purchased from Merck KGaA (FIG. 5). Such results also verify that all clones tested bind the same epitope of EGFR as the ERBITUX®.

Figure 6B:
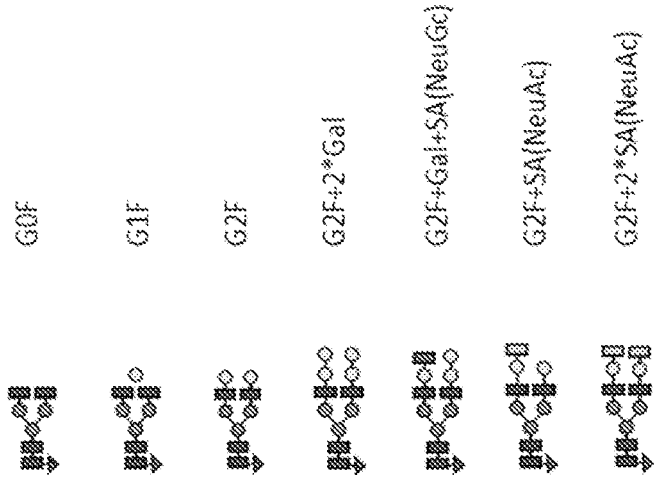

Clones 1-26/2-68 (LC/HC), 1-26/3-67 (LC/HC); #8/#33 (LC/HC), and #34/#33 (LC/HC) each comprise a CDR-H2 that was engineered to remove the glycosylation site. The glycosylation profiles of whole IgG clones 1-26/2-68 (LC/HC), 1-26/3-67 (LC/HC); #8/#33 (LC/HC), and #34/#33 (LC/HC), ERBITUX® purchased from Merck KGaA, and HLX05 were analyzed via HPLC. G0F and G1F account for most types of glycans among the clones tested, whereas G0 was detected on both ERBITUX® from Merck KGaA and HLX05 (FIG. 6). Additional glycan analysis was performed on Fab fragments and Fc fragments of 1-26/3-67 (LC/HC), ERBITUX® purchased from Merck KGaA, and HLX05. G0F and G1F were detected on the Fc of 1-26/3-67, but no glycans were detected on the Fab of 1-26/3-67. By contrast, trace G2F as well as G0F and G1F was detected on Fc fragments from both ERBITUX® purchased from Merck KGaA and HLX05. G2F +2*Gal and G2F+Gal+SA(NeuAc) was detected on the Fab fragment of ERBITUX® purchased from Merck KGaA, and G2F +2*SA(NeuAC) and G2F+Gal+SA(NeuAc) was detected on the Fab fragment of HLX05 (FIG. 6).

SPR was performed on HLX05 produced in house, 348311/2-68 (LC/HC), 1-26/2-68 (LC/HC), 348311/3-67 (LC/HC), and 1-26/3-67 (LC/HC). The results are shown in Table 5 below.

TABLE 5

| LC/HC | ka (1/(M*s)) | kd (1/s) | $K_D$ (M) | Fold difference in $K_D$ |
|---|---|---|---|---|
| HLX05 | 5.02E6 (±1.28E3) | 6.38E−4 (±8.89E−6) | 1.27E−10 (±1.81E−12) | 1 |
| 348311/2-68 | 5.80E6 (±2.49E3) | 7.29E−4 (±8.83E−6) | 1.26E−10 (±1.58E−12) | 1 |

TABLE 5-continued

| LC/HC | ka (1/(M*s)) | kd (1/s) | $K_D$ (M) | Fold difference in $K_D$ |
|---|---|---|---|---|
| 1-26/2-68 | 6.48E6 (±8.14E2) | 4.21E−4 (±9.60E−6) | 6.49E−11 (±1.49E−12) | 2.0 |
| 348311/3-67 | 6.10E6 (±3.31E3) | 1.51E−3 (±6.58E−6) | 2.47E−10 (±1.21E−12) | 0.5 |
| 1-26 /3-67 | 5.09E6 (±1.52E3) | 5.53E−4 (±1.13E−5) | 1.09E−10 (±2.24E−12) | 1.2 |

Clone 1-26/2-68 was measured as having a Kd of 6.49× $10^{−11}$, i.e. an affinity for EGFR that is 2-fold that of HLX05. 1-26/3-67 was measured as having a Kd of 1.09×$10^{−10}$, i.e. an affinity for EGFR that is 1.2-fold that of HLX05.

IgG clones comprising the 1-26 light chain and either the 2-68 or 3-67 heavy chain demonstrated a 2- to 3-fold higher affinity for EGFR than HLX05. (See Table 6 below.)

TABLE 6

| LC/HC | ka (1/(M*s)) | kd (1/s) | $K_D$ (M) | Fold difference in $K_D$ |
|---|---|---|---|---|
| HLX05 | 8.31E6 (±8.82E4) | 2.07E−3 (±1.88E−4) | 2.49E−10 (±2.52E−11) | 1 |
| 1-26/2-68 | 8.82E6 (±2.73E3) | 7.18E−4 (±7.36E−4) | 8.14E−11 (±8.34E−11) | 3.1 |
| 1-26/3-67 | 8.93E6 (±1.69E3) | 9.95E−4 (±2.58E−4) | 1.11E−10 (±2.89E−11) | 2.2 |
| #8/#33 | 6.09E6 (±1.33E5) | 1.02E−4 (±1.13E−5) | 1.67E−11 (±2.22E−12) | 13.9 |
| #31/#33 | 7.24E6 (±2.75E5) | 5.47E−4 (±2.69E−5) | 7.56E−11 (±6.59E−12) | 3.3 |
| #34/#33 | 8.25E6 (±8.15E4) | 6.17E−4 (±1.34E−5) | 7.48E−11 (±2.37E−12) | 3.3 |
| #8/3-67 | 6.68E6 (±6.42E3) | 6.15E−4 (±1.06E−3) | 9.21E−11 (±1.58E−10) | 2.7 |
| #8/#31 | 7.52E5 (±5.26E3) | 1.00E−3 (±5.81E−4) | 1.33E−10 (±7.74E−11) | 1.9 |
| #31/3-67 | 6.45E6 (±1.68E3) | 1.16E−3 (±4.10E−4) | 1.80E−10 (±6.36E−11) | 1.4 |

Figure 7:
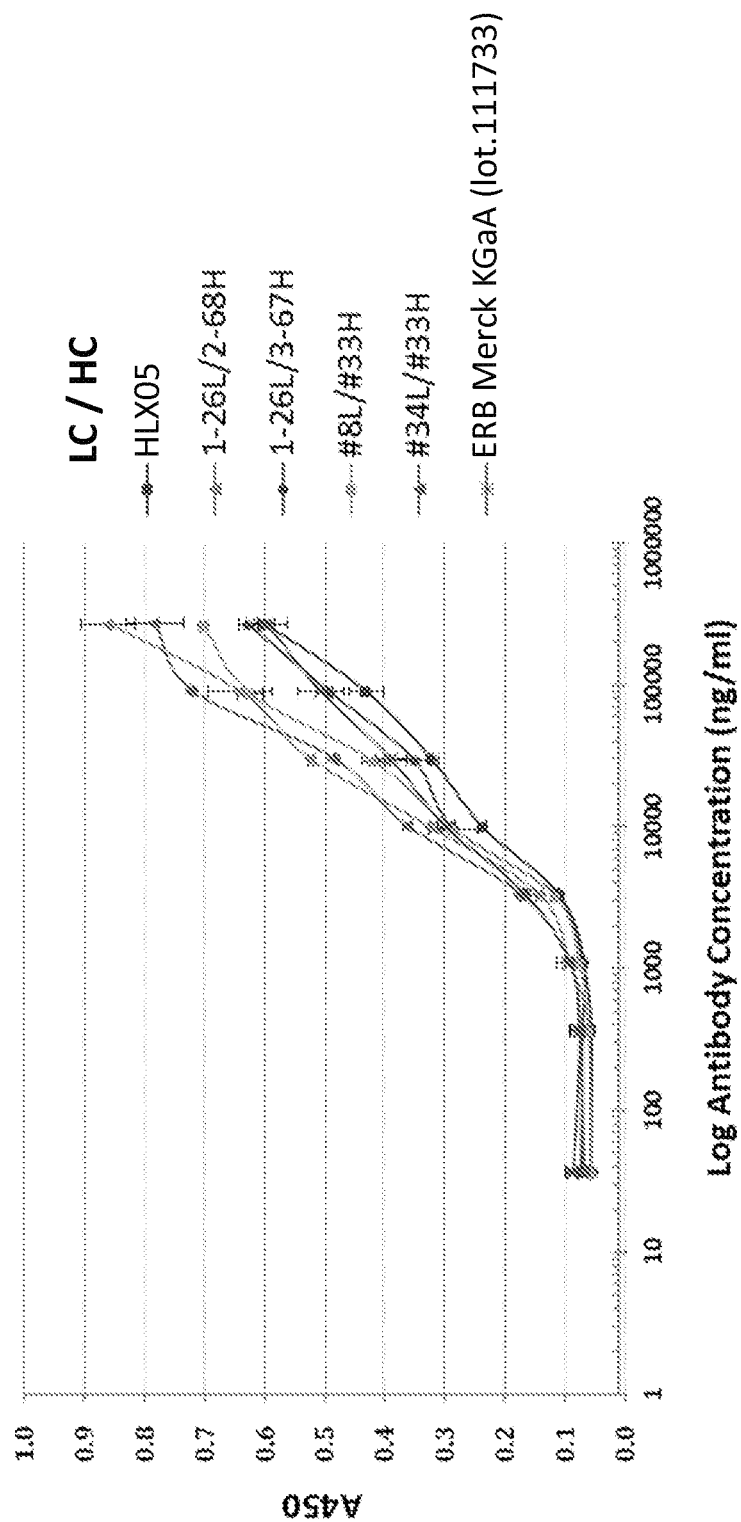
FIG. 7 shows the results of ELISAs performed to compare FcγIII binding of HLX05, ERBITUX®, and anti-EGFR antibodies 1-26/2-68, 1-26/3-67, #8/#33, #34/#33.
Figure 9A:
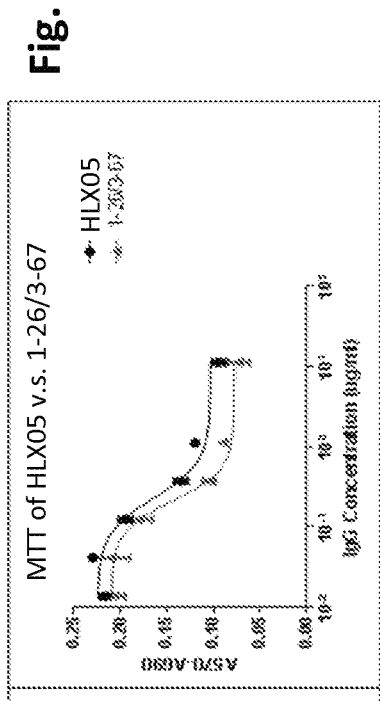
FIG. 9A shows the results of analyses performed to compare the anti-proliferative effects of HLX05 and anti-EGFR antibody 1-26/2-68 on A431 cells.
Figure 9B:
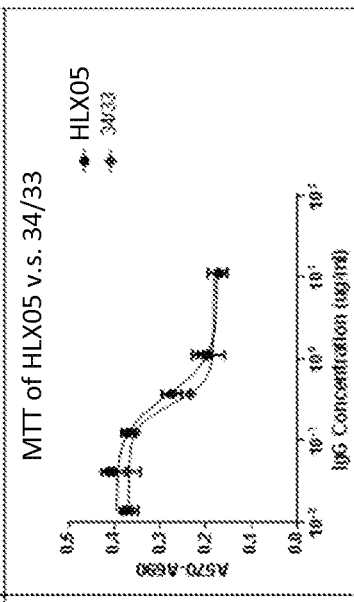
FIG. 9B shows the results of analyses performed to compare the anti-proliferative effects of HLX05 and anti-EGFR antibody #8/#33 on A431 cells.
Figure 9C:
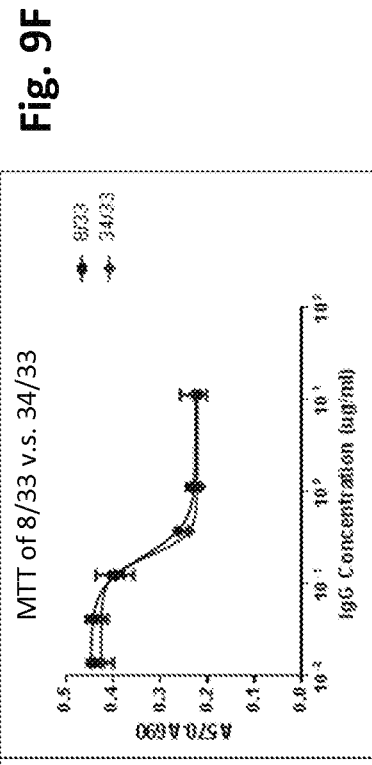
FIG. 9C shows the results of analyses performed to compare to compare the anti-proliferative effects of anti-EGFR antibodies 1-26/2-68 and 1-26/3-67 on A431 cells.
Figure 9D:
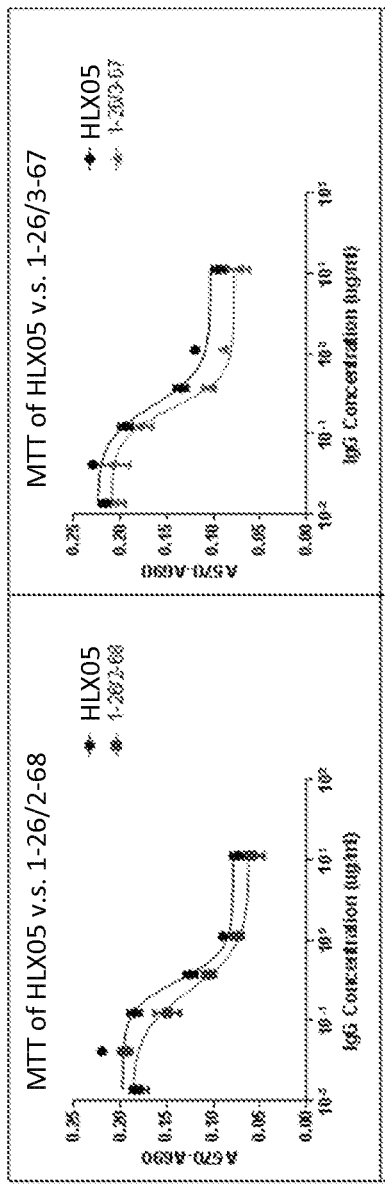
FIG. 9D shows the results of analyses performed to compare the anti-proliferative effects of HLX05 and anti-EGFR antibody 1-26/3-67 on A431 cells.
Figure 9E:
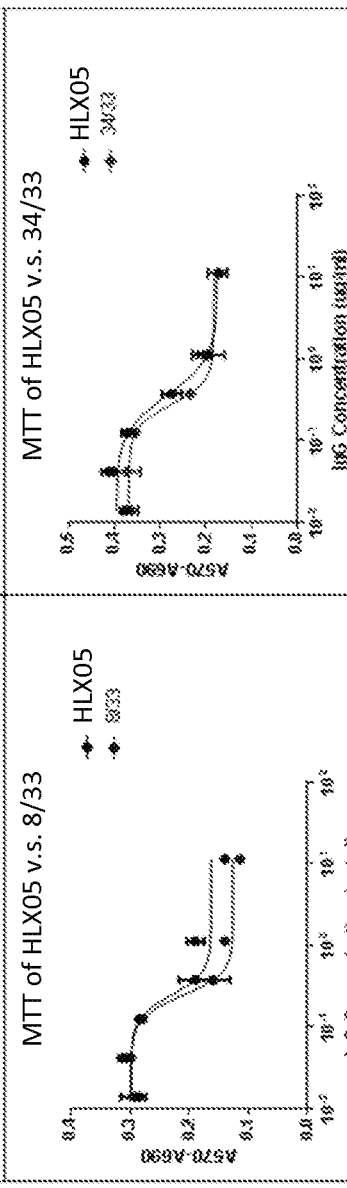
FIG. 9E shows the results of analyses performed to compare the anti-proliferative effects of HLX05 and anti-EGFR antibody #34/#33 on A431 cells.
Figure 9F:
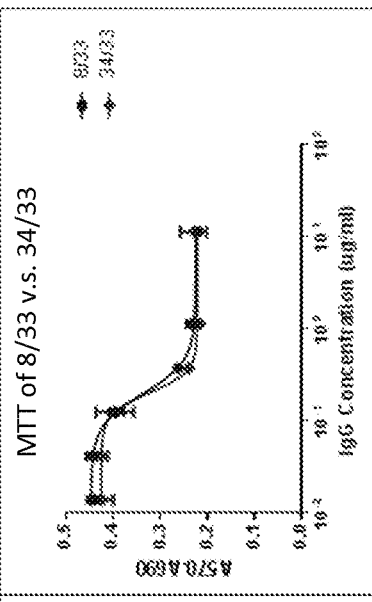
FIG. 9F shows the results of analyses performed to compare the anti-proliferative effects of anti-EGFR antibodies #8/#33 and #34/#33 on A431 cells.
Figure 10:
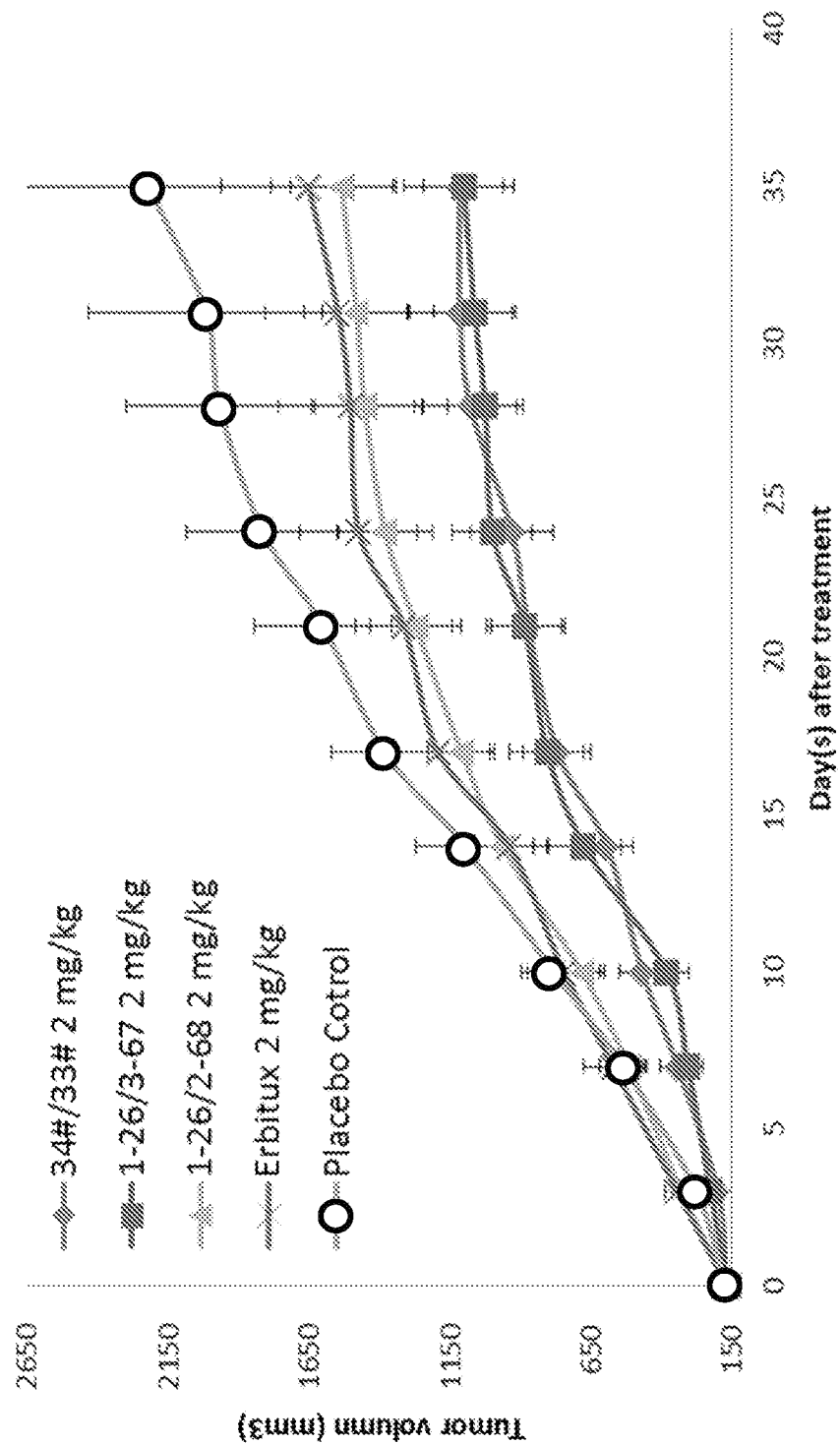
FIG. 10 depicts the results of an A431 tumor xenograft assay measuring the ability of ERBITUX®, #34/#33, 1-26/3-67, and 1-26/2-68 to inhibit tumor growth.

FcγRIIIA binding of the anti-EGFR antibody clones generated via affinity maturation was assayed via ELISA. Briefly, microtiter wells were coated with FcγRIIIA and blocked with BSA. The following antibodies were added at a concentration of 1 μg/ml: HLX05 produced in-house, 1-26/2-68 (LC/HC), 1-26/3-67 (LC/HC), #8/#33 (LC/HC), #34/#33 (LC/HC), and ERBITUX® purchased from Merck KGaA. Following a 1-hour incubation, anti-human kappa light chain-HRP conjugated antibody was added to each well. TMB substrate was added to the wells and incubated for 7 minutes. After the reaction was stopped, HRP activity was measured by monitoring the increase in absorbance at 450 nm. As shown in FIG. 7, each of 1-26/2-68 (LC/HC), 1-26/3-67 (LC/HC), #8/#33 (LC/HC), #34/#33 (LC/HC) binds FcγRIIIa at with affinity similar to that of ERBITUX® purchased from Merck KGaA and that of HLX05.

The ADCC activity of the antibody clones generated via affinity maturation was compared to that of HLX05 produced in-house. The assay was performed as described in Suzuki et al. (2007) "A Nonfucosylated Anti-HER2 Antibody Augments Antibody-Dependent Cellular Cytotoxicity in Breast Cancer Patients." *Clin Cancer Res* 13, 1875-1882. All clones tested were shown to exhibit ADCC activity similar to that of HLX05 produced in house. #34/#33 (LC/HC) was found to have slightly improved ADCC activity (FIGS. 8A-G).

The anti-proliferative effects of 1-26/2-68 (LC/HC), 1-26/3-67 (LC/HC), #8/#33 (LC/HC), #34/#33 (LC/HC), and HLX05 were on human A431 epidermoid carcinoma cells were compared in an MTT assay. The MTT colorimetric assay is an established method of determining viable cell number in proliferation and cytotoxicity studies. This assay is based on the cleavage of the yellow tetrazolium salt, MTT, to form a soluble blue formazan product by mitochondrial enzymes, and the amount of formazan produced is directly proportional to the number of living, not dead cells, present during MTT exposure (see Mosmann (1983) *J Immunol Methods* 1983, 65:55-63). 1-26/2-68 (LC/HC), 1-26/3-67 (LC/HC), #8/#33 (LC/HC), #34/#33 (LC/HC) or HLX05 was added to the cells at increasing concentrations. Following incubation, MTT reagent was added to the cells. The resulting MTT-products were determined by measuring the absorbance at 570 nm. The cell viability was determined using the formula:

Viability %=(optical density of sample/optical density of control)×100

$IC_{50}$ values were calculated as the concentrations that show 50% inhibition of proliferation on any tested cell line. As shown in FIG. 9, 1-26/2-68 (LC/HC), 1-26/3-67 (LC/HC), #8/#33 (LC/HC), and #34/#33 (LC/HC) were shown to have an improved anti-proliferative effect as compared to HLX05.

Mice bearing human A431 epidermoid carcinoma tumor xenografts were used to assay the therapeutic efficacy of the anti-EGFR antibodies described herein. Briefly, human A431 epithelial carcinoma cells (inoculum=2×$10^6$ cells) were implanted into male BALB/c nude mice. The mice were randomized into 5 groups. Each group was treated with one of the dosing regimens described in Table 7 below:

TABLE 7

| Group | Animals | Tumor | Treatment Agent (Ab) | Dose | Treatment Schedule |
|---|---|---|---|---|---|
| 1 | BALB/c NU Male 6 weeks old 7 mice/group | A431 Inoculum = 2 × $10^6$ cells | #34/#33 | 2 mg/kg | Day 7 after inoculation; twice a week for 5 weeks |
| 2 | | | 1-26/3-67 | | |
| 3 | BALB/c NU Male 6 weeks old 6 mice/group | | 1-26/2-68 | | |
| 4 | | | ERBITUX ® (Merck KGaA) Batch: 161734 | | |
| 5 | | | Placebo | 10 ml/kg | |

35 days following the beginning of treatment, tumors in mice treated with ERBITUX® were about 26% smaller than tumors in mice receiving placebo. Tumors in mice treated with 1-26/2-68 were about 31% smaller than tumors in mice receiving placebo (p<0.05). Tumors in mice treated with #8/#33 or #34/#33 were about 50% smaller than tumors in mice receiving placebo (p<0.01) and approximately 50% smaller than mice receiving ERBITUX® (p<0.05). See FIG. 10 and Table 8 below.

TABLE 8

| | $TV^1$ (35 Days) | $RTV^2$ (35 Days) | TV/CV $\%^3$ (35 Days) | TGI $\%^4$ (35 Days) | p Value of $TV^5$ (35 Days) | |
|---|---|---|---|---|---|---|
| #34/#33 (2 mg/kg) | 1116 | 657% | 50% | 54% | 0.003 | p < 0.01 |
| 1-26/3-67 (2 mg/kg) | 1102 | 670% | 50% | 54% | 0.002 | p < 0.01 |
| 1-26/2-68 (2 mg/kg) | 1535 | 911% | 69% | 33% | 0.045 | p < 0.05 |
| ERBITUX® (Merck KGaA) Batch: 161734 (2 mg/kg) | 1652 | 991% | 74% | 27% | 0.104 | p > 0.05 |
| Placebo | 2219 | 1261% | | | | |

[1]TV: Tumor volume (mm$^3$)
[2]RTV: Tumor volume relative to initial
[3]TV/CV %: Treatment group volume/Control group volume
[4]TGI %: Tumor growth inhibition rate = 1 − (T35 − T0)/(C35 − C0)%
[5]p value: <0.05 = * <0.01 =  <0.001 = *

Figure 11:
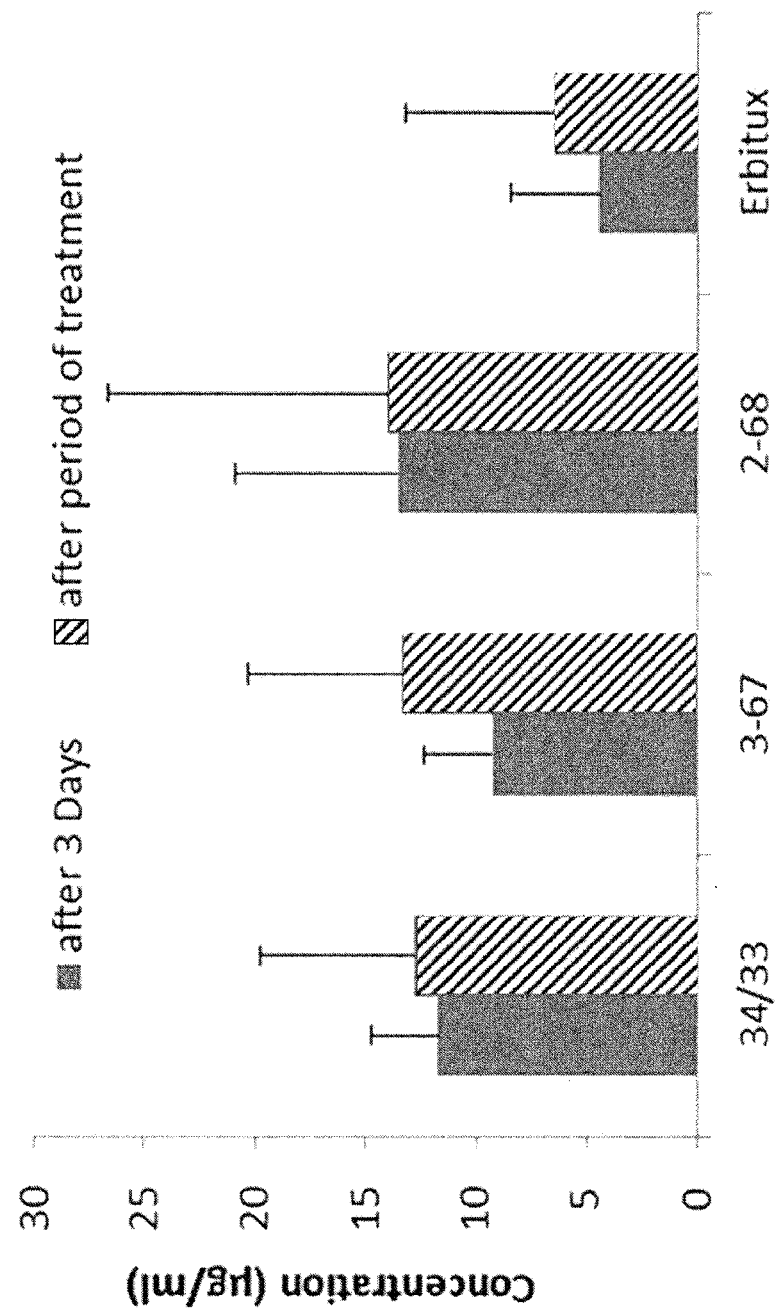
FIG. 11 shows the serum levels of #34/#33, 1-26/3-67, 1-26/2-68, and ERBITUX® on both Day 3 and Day 35.
Figure 12:
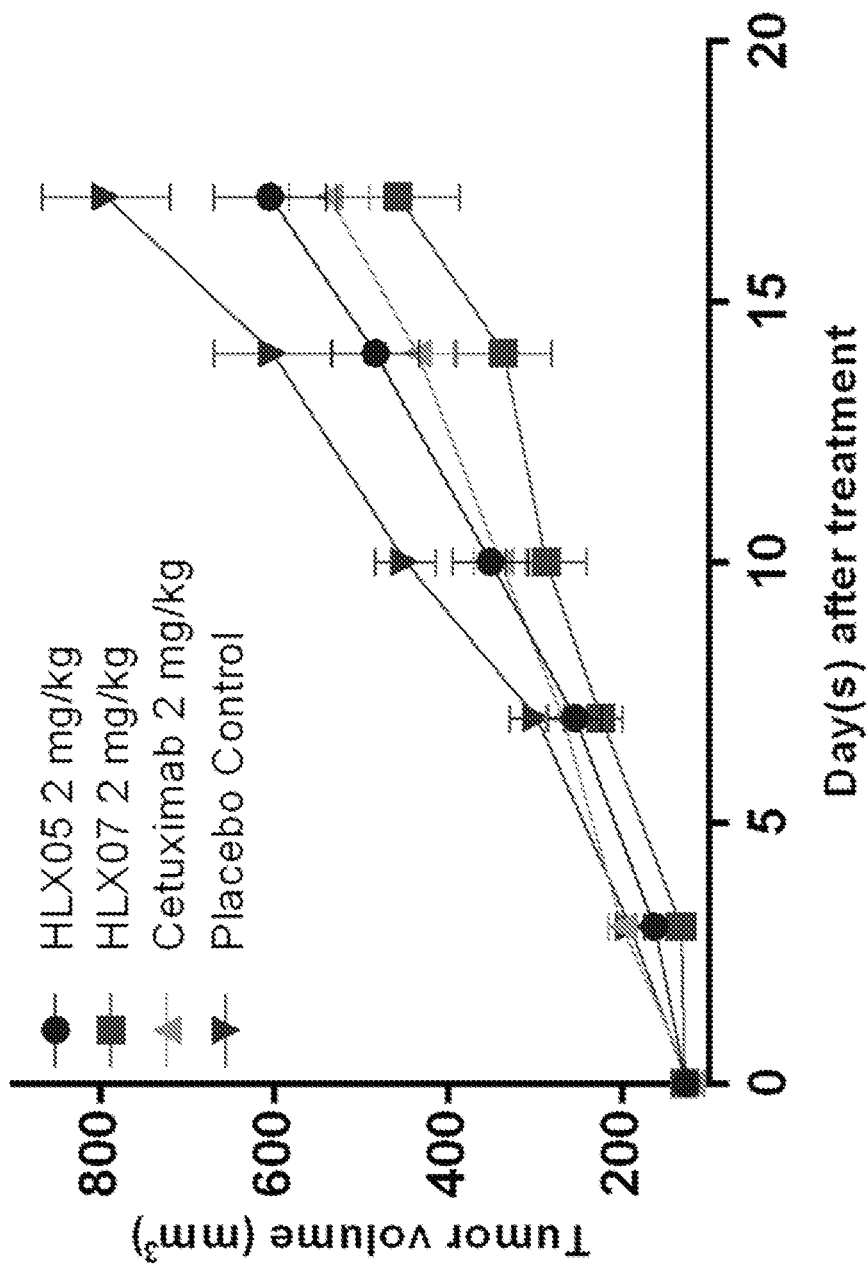
FIG. 12 depicts the results of a FaDu tumor xenograft assay measuring the ability of HLX05, 1-26/3-67, ERBITUX®, and placebo to inhibit tumor growth.
Figure 13:
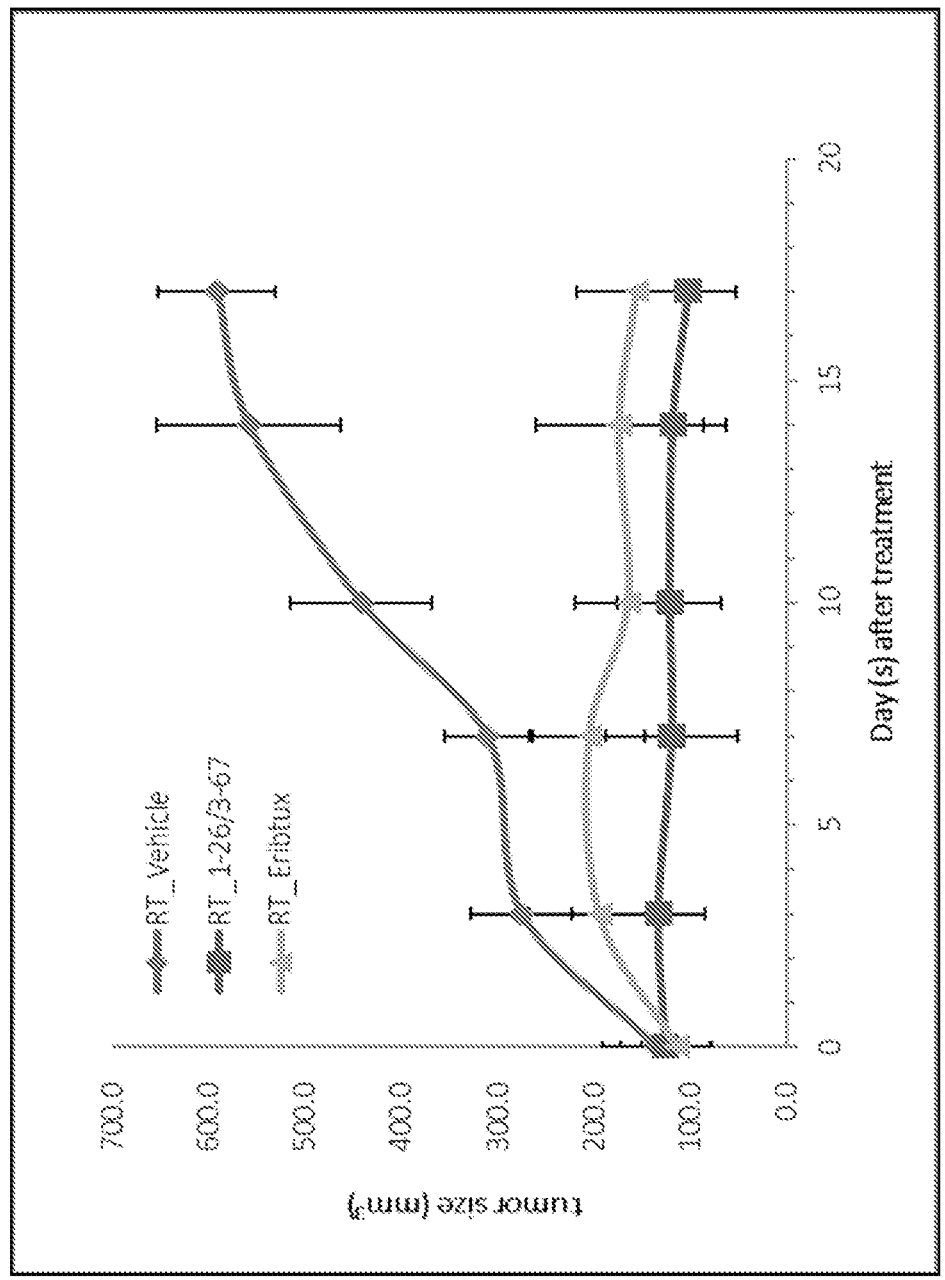
FIG. 13 depicts the results of a FaDu tumor xenograft assay measuring the ability of 1-26/3-67+radiation therapy, ERBITUX®, +radiation therapy and placebo+radiation therapy to inhibit tumor growth.

Serum samples were taken from each mouse on Day 3 and Day 35 to determine serum concentrations of #34/#33, 1-26/3-67, 1-26/2-68, or ERBITUX® at these two time points. Briefly, wells of a microtiter dish were coated with EGFR-AP that was diluted 8-fold. The serum samples were diluted 5000-fold and added to the wells. The amount of captured antibody in each well was quantified using a goat-anti-human IgG-Fc-HRP-conjugated secondary antibody. This experiment was performed in duplicate, and the results are shown in FIG. 11. The serum levels of #34/#33, 1-26/3-67, 1-26/2-68 were higher than the serum level of ERBITUX® on both Day 3 and Day 35.

Example 2. FaDu Hypopharynx Squamous Cell Carcinoma Tumor Xenograft Assays

Mice bearing human FaDu hypopharynx squamous cell carcinoma tumor xenografts were used to assay the therapeutic efficacy of the anti-EGFR antibodies described herein. Briefly, human FaDu hypopharynx squamous cell carcinoma cells (inoculum=2×10$^6$ cells) were implanted subcutaneously in female BALB/c nude mice. The mice were randomized into 4 groups containing 7 mice each. Each group was treated with one of the dosing regimens described in Table 9 below:

TABLE 9

| Group | Animals | Tumor | Treatment Agent (Ab) | Dose | Treatment Schedule |
|---|---|---|---|---|---|
| 1 | BALB/c NU | FaDu | HLX05 | 2 mg/kg | Day 7 after |
| 2 | Female | Inoculum = | 1-26/3-67 | | inoculation; |
| 3 | 6 weeks old 7 mice/group | 2 × 10$^6$ cells | ERBITUX® (Merck KGaA) Batch: 164362 | | twice a week via IP injection for 2-3 weeks |
| 4 | | | Placebo | 10 ml/kg | |

17 days following the beginning of treatment, tumors in mice treated with ERBITUX® were about 38% smaller than tumors in mice receiving placebo. Tumors in mice treated with HLX05 were about 29% smaller than tumors in mice receiving placebo (p<0.05). Tumors in mice treated with 1-26/3-67 were about 51% smaller than tumors in mice receiving placebo (p<0.01). See FIG. 12 and Table 10 below.

TABLE 10

|  | TV (17 days) | RTV (17 days) | TV/CV % (17 days) | TGI % (17 days) | p value of TV (17 days) | |
|---|---|---|---|---|---|---|
| HLX05 2 mg/kg | 605 | 493% | 76% | 29% | 0.03 | p < 0.05 |
| HLX07 1-26/3-67 2 mg/kg | 458 | 350% | 58% | 51% | 0.0014 | p < 0.01 |
| ERBITUX (Merck KGaA) Batch: 164362 2 mg/kg | 538 | 470% | 68% | 38% | 0.003 | p < 0.01 |
| Placebo 10 ml/kg | 794 | 705% |  |  |  |  |

In another set of experiments, NOD-SCID mice were given antibody treatment plus radiotherapy (XRT). Briefly, human FaDu hypopharynx squamous cell carcinoma cells (inoculum=1×10$^6$ cells) were implanted subcutaneously in male NOD-SCID mice. The mice were randomized into 3 groups. Each group was treated with one of the dosing regimens described in Table 11 below:

TABLE 11

| Group | Animals | Tumor | Antibody/ Dose | Radiation Therapy Treatment Schedule | Antibody Treatment Schedule |
|---|---|---|---|---|---|
| 1 | NOD/SCID Male 8 weeks old 5 mice/group | FaDu Inoculum = 1 × 10$^6$ cells | None | 10 Gy x 1, QOD on Day 14 after inoculation | Beginning on Day 13 after inoculation; Ab administered via IP injection for 5 days |
| 2 |  |  | ERBITUX ® (Merck KGaA) 250 µg/mice |  |  |
| 3 |  |  | 1-26/3-67 250 µg/mice |  |  |

After 5 days of treatment, tumors in mice given ERBITUX and XRT combination treatment were 91% smaller than tumors in mice given XRT alone. Tumors in mice given HLX07 and XRT combination treatment were 105% smaller than tumors in mice given XRT alone. See FIG. 13 and Table 12 below. (RT=radiation therapy)

TABLE 12

|  | TV (17 days) | RTV (17 days) | TV/CV (17 days) | TGI % (17 days) | p value of TV (17 days) | |
|---|---|---|---|---|---|---|
| RT_vehicle | 591 | 480% | — | — | — | — |
| RT_ERBITUX ® (Merck KGaA) 250 µg/mice | 156 | 137% | 26% | 91% | 1.76E−6 | p < 0.001 |
| RT_1-26/3-67 250 µg/mice | 102 | 77% | 17% | 105% | 3.69E−7 | p < 0.001 |

Example 3. Anti-Epidermal Growth Factor Antibody-Drug Conjugate

DM1 (N2'-deacetyl-N2'-(3-mercapto-1-oxopropyl)maytansine) is a potent inhibitor of microtubule assembly that has been shown to induce mitotic arrest (see, e.g., Chan (2008) *Acc Chem Res* 41, 98-107; Oroudjev et al. (2010) *Mol Cancer Ther* 9, 2700-2713; and Remillard et al. (1975) *Science* 189, 1002-1005). An HLX07-DM1 conjugate was prepared and its efficacy as an anticancer agent was assessed as described below.

HLX07 was formulated into PBS, pH6.5 using PD10 desalting columns. The final concentration of HLX07 was adjusted to 7.5 mg/mL using the same buffer. In separate tubes, DM1 and SMCC were prepared as 10 mM DMF solutions. Equal volume of DM1 and SMCC solutions were mixed and allowed to complete the reaction at room temperature for 30 minutes. The DM1-SMCC was then added to HLX07 solution in 4.5 to 1 molar ratio. The mixed solution was incubated at room temperature for 2 hours. The excess amount of small reactant was removed using PD10 columns. Concentration of antibody-drug conjugate was determined using A280, with proper correction from A252. The drug-to-antibody ratio was determined using the A280/A252 ratios.

Figure 14A:
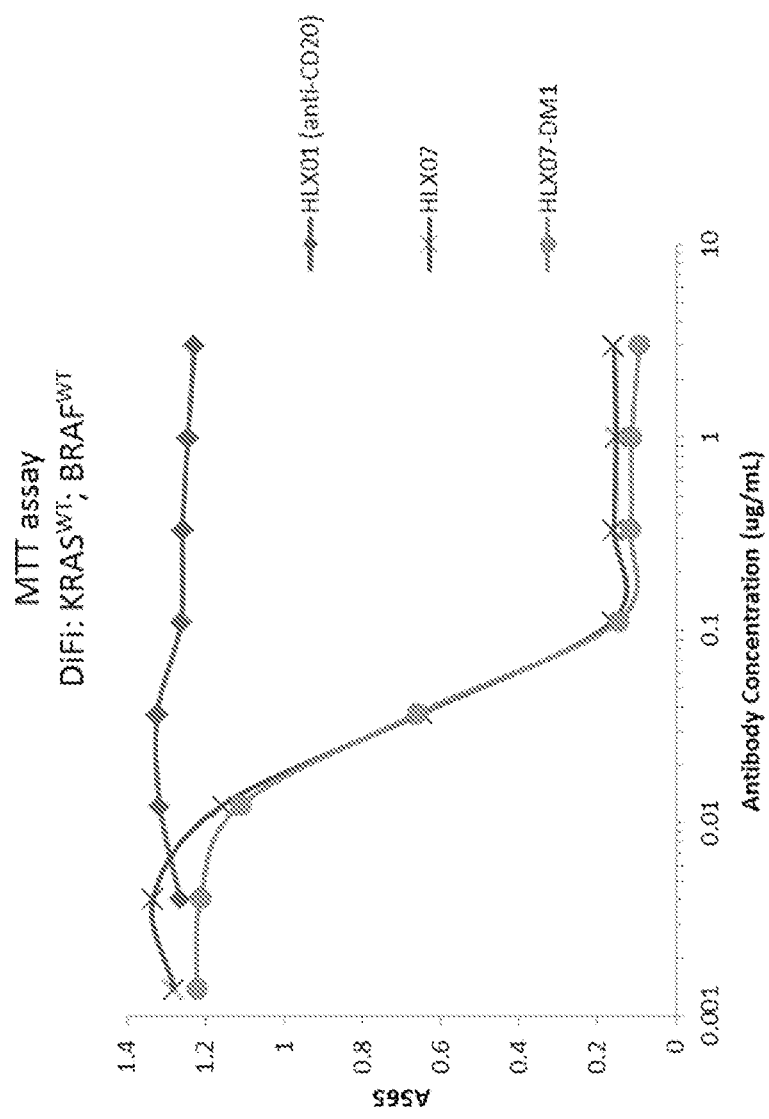
FIG. 14A shows the results of in vitro experiments performed to assess the ability of HLX07-DM1, HLX07, and control antibody to inhibit growth in DiFi cells (KRAS$^{WT}$, BRAF$^{WT}$).
Figure 14B:
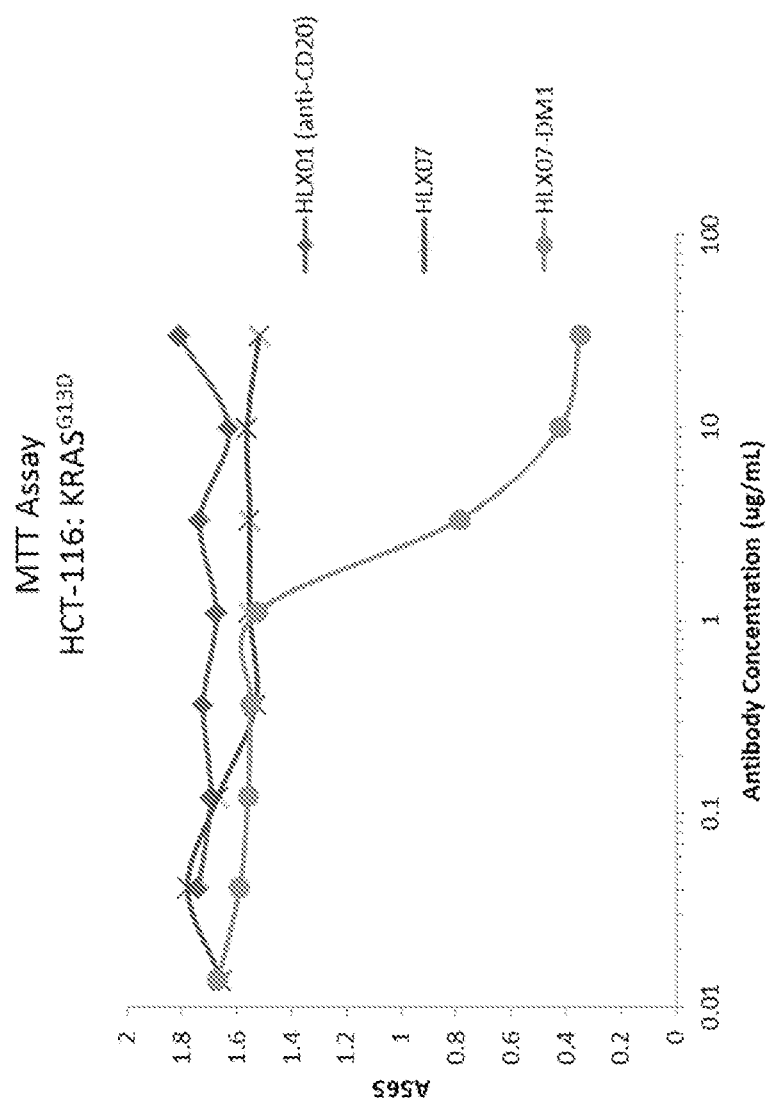
FIG. 14B shows the results of in vitro experiments performed to assess the ability of HLX07-DM1, HLX07, and control antibody to inhibit growth in HCT-116 cells (KRAS$^{G13D}$).
Figure 14C:
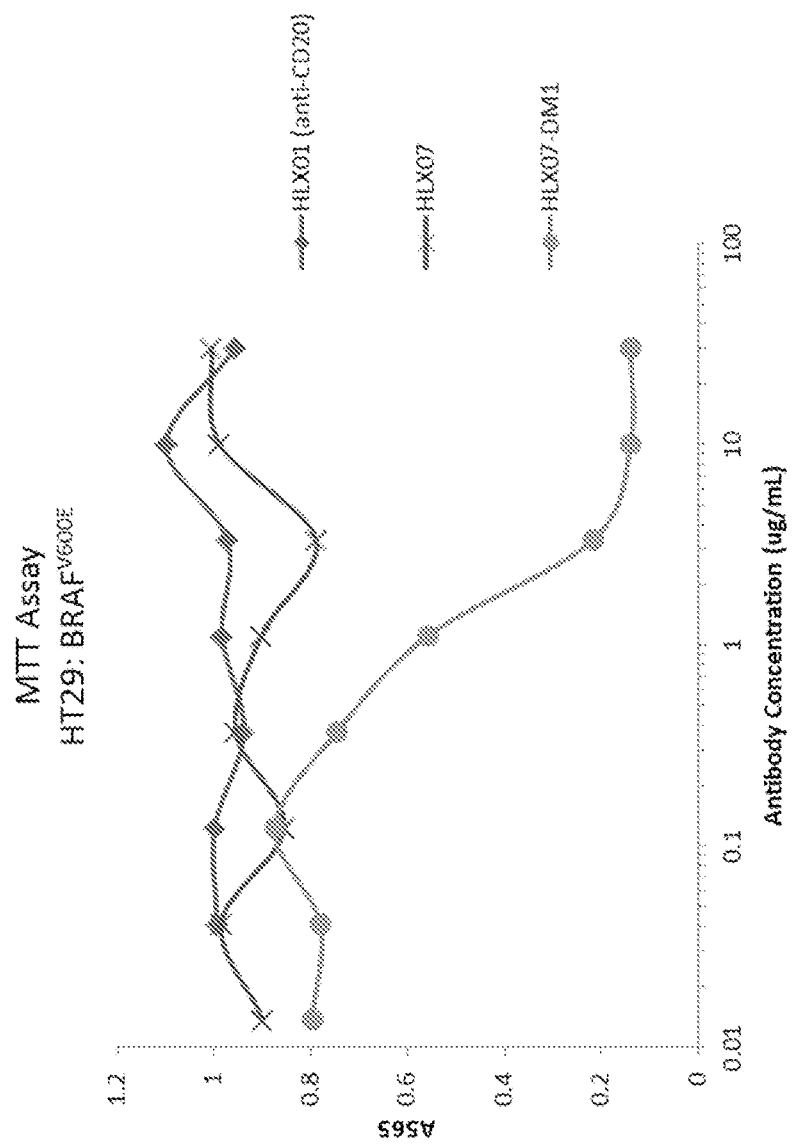
FIG. 14C shows the results of in vitro experiments performed to assess the ability of HLX07-DM1, HLX07, and control antibody to inhibit growth in HT29 cells (BRAF$^{V600E}$).

The ability of HLX07-DM1 to mediate inhibition of EGFR-positive human colon cancer cells was measured in a series of in vitro experiments using DiFi (KRAS$^{WT}$ and BRAF$^{WT}$), HCT-116 (KRAS$^{G13D}$) and HT-29 (BRAF$^{V600E}$) cell lines. In all studies, cells from each cell line were incubated with increasing concentrations of HLX07-DM, HLX07, or control antibody (anti-CD20) (3-fold in series) at 37° C. for 3 days. Growth inhibition was measured using the MTT assay. Viable cells with active metabolism convert MTT (i.e., 3-(4,5-dimethylthiazol-2-yl)-2,5-diphenyltetrazolium bromide, a yellow dye) into a purple colored formazan product with an absorbance at 565 nm. As shown in FIG. 14A, the growth inhibitory effect of HLX07-DM1 and HLX07 was similar in EGFR wild-type DiFi human rectal carcinoma cells. However, only HLX07-DM1 showed antiproliferative effect on KRAS mutated HCT-116 (FIG. 14B) and BRAF mutated HT-29 cells (FIG. 14C).

Example 4. Afucosylated Anti-Epidermal Growth Factor Antibody

Figure 15A:
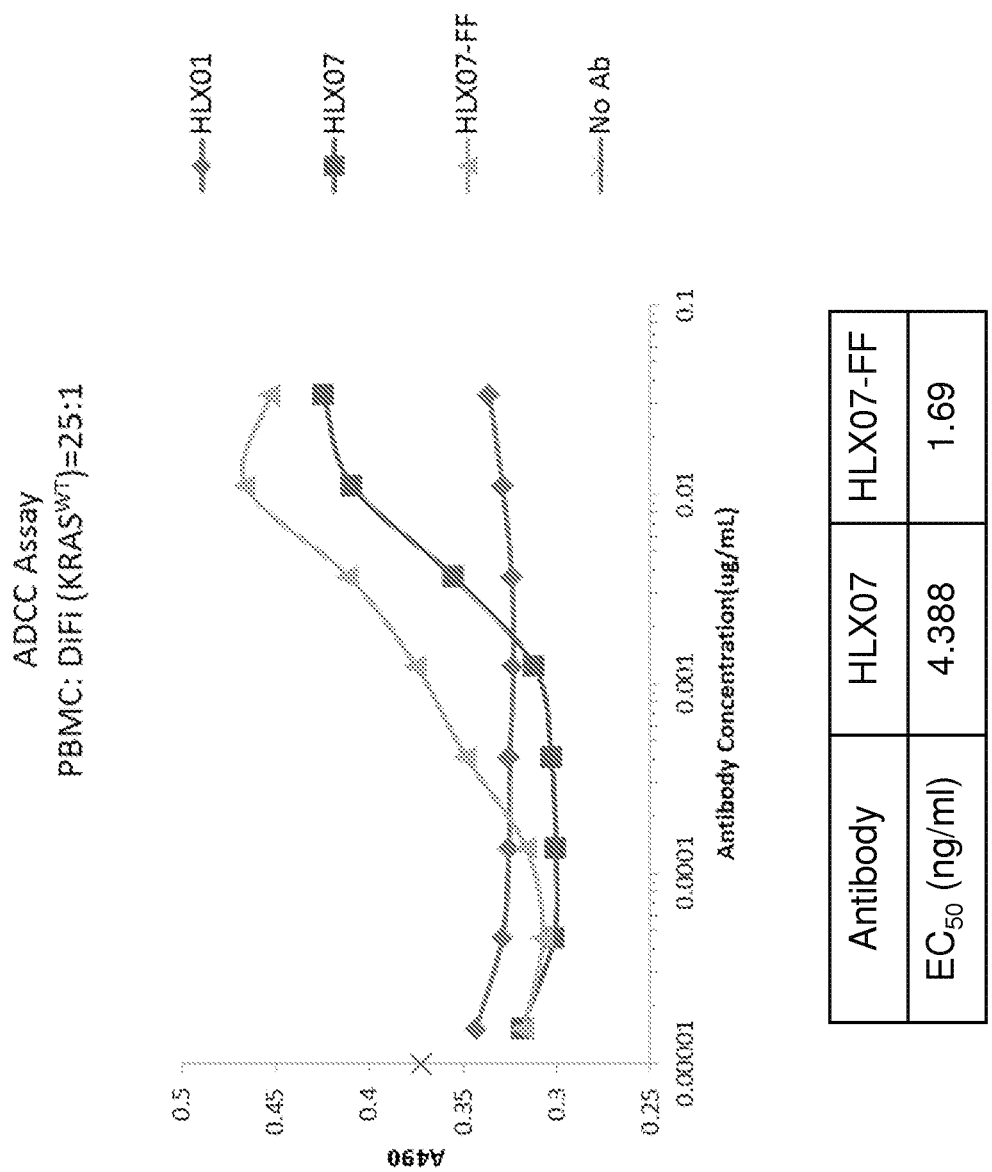
FIG. 15A shows the ADCC activity of 1-26/3-67-FF (i.e., "fuscose free"), 1-26/3-67, and control antibody against DiFi cells (KRAS$^{WT}$) with PBMC effector cells.

To assess antibody-dependent cell-mediated cytotoxicity activity of fucose-free HLX07 (i.e., HLX07-FF), ADCC assays were performed using PBMC from healthy human donors as effector cells and DiFi, a human rectal carcinoma cell line that is wild-type for KRAS, as target cells. Human PBMC were freshly prepared from the whole blood of healthy donors using Histopaque-1077 (Sigma-Aldrich), and suspended in RPMI medium (RPMI-1640 containing L-glutamine, 25 mM HEPES, penicillin, streptomycin, and 10% FBS) at the density of 5×10$^6$ cells/mL. The DiFi target cells were suspended in RPMI medium and plated in a 96-well U-bottom microtiter plate at 1×10$^4$ cells/well. Serial dilutions of HLX07-FF, HLX07, and control antibody (anti-CD20) were added in the individual wells at various concentrations from 1.5 pg/ml to 3.3 ng/mL. Next, PBMC were added to the wells to achieve an effector cell: target cell ratio of 25:1, and the plates were incubated at 37° C. for 5 hours. The plates were then centrifuged and the supernatants were assayed for lactate dehydrogenase activity. The absorbance of the supernatants at 490 nm was recorded to determine the release of lactate dehydrogenase using Cytoscan™-LDH Cytotoxicity Assay kit (G-Bioscience). EC$_{50}$ values were calculated as the concentrations that show 50% induction of ADCC on tested cell lines. As shown in FIG. 15A, HLX07-FF showed 50% induction at 1.69 ng/ml, a concentration 60% lower than the concentration of HLX07 (i.e., 4.388 ng/ml) required to show 50% induction.

KRAS mutation is a predictive biomarker for resistance to ERBITUX in metastatic colon cancer. See "Class Labeling Changes to anti-EGFR monoclonal antibodies, cetuximab (Erbitux) and panitumumab (Vecitibix): KRAS Mutations." U.S. Food and Drug Administration 2010-01-11. To compare the ADDC activity of HLX07-FF and HLX07 in KRAS-mutated cells, the assay described above was repeated using HCT-116, i.e., a human colon carcinoma cell line having the KRAS$^{G13D}$ mutation, as target cells. The assay was performed using a 30:1 effector cell: target cell ratio. Serial dilutions of HLX07-FF, HLX07, and control antibody (anti-CD20) were added in the individual wells at various concentrations from 0.1 µg/ml to 5.1 pg/ml following 3-fold dilutions in series. As shown in FIG. 15B, HLX07-FF demonstrated 4.8-fold higher ADCC activity in HCT-116 cells than fucosylated HLX07.

BRAF mutation is a predictive biomarker for resistance to ERBITUX in metastatic colon cancer. See Di Nicolitano et al. (2008) J. Clin Oncol. 26, 5705-5712. To compare the ADDC activity of HLX07-FF and HLX07 in BRAF-mutated cells, the assay described above was repeated as described above using HT29, a human colorectal adenocarcinoma cell line having the BRAF$^{V600E}$ mutation, as target cells. The assay was performed using a 30:1 effector cell: target cell ratio. Serial dilutions of HLX07-FF, HLX07, and control antibody (anti-CD20) were added in the individual wells at various concentrations from 0.1 µg/ml to 5.1 pg/ml following 3-fold dilutions in series. As shown in FIG. 15C, HLX07-FF demonstrated 4.7-fold higher ADCC activity in HT29 cells than fucosylated HLX07.

Example 5. Pharmacokinetic Profiles of Anti-Epidermal Growth Factor Antibodies

Figure 16A:
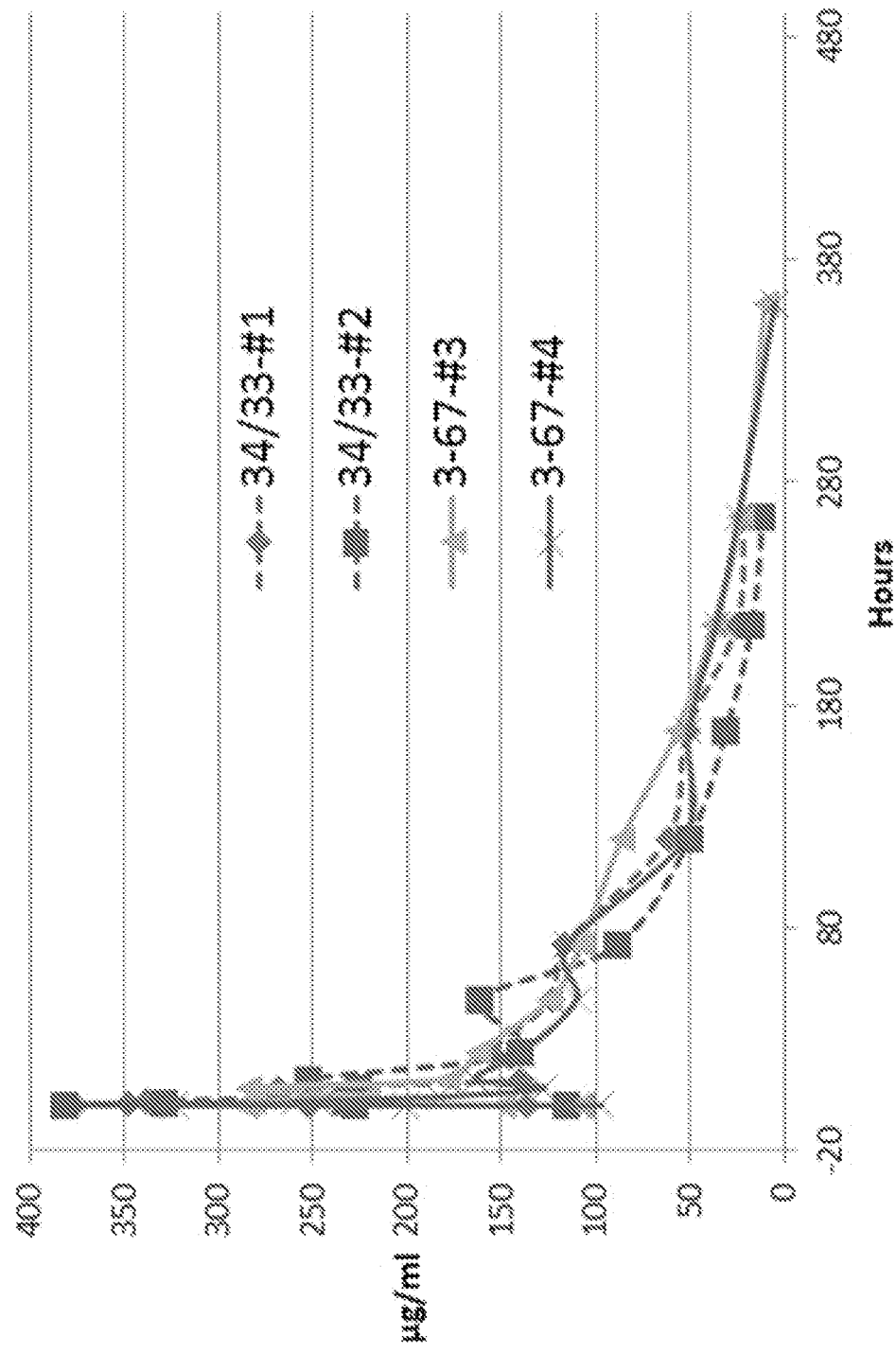
FIG. 16A shows the results of an ELISA performed to compare the serum concentrations of 34/33 and 3/67 over time in cynomolgus monkeys.
Figure 16B:
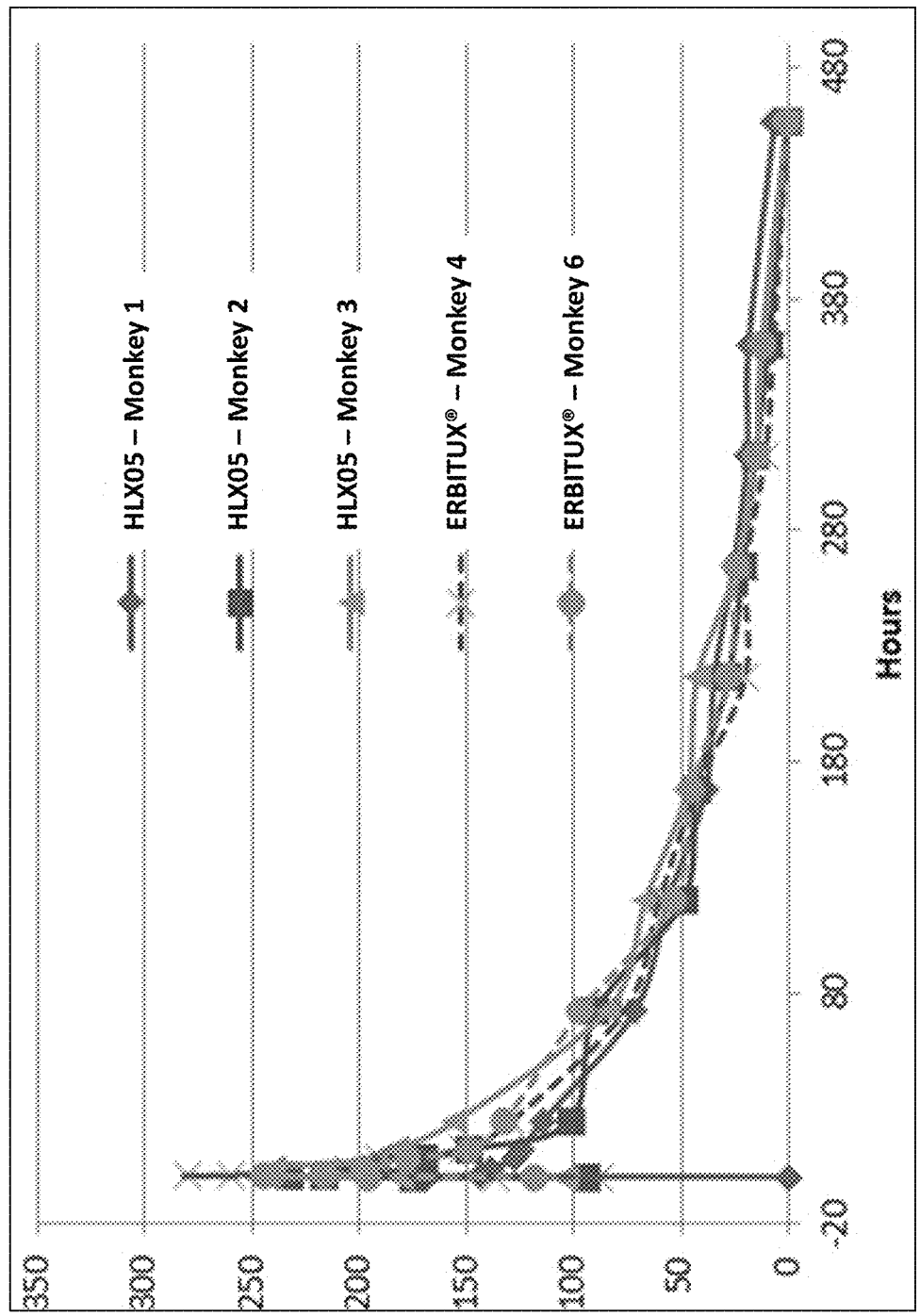
FIG. 16B shows the results of an ELISA performed to compare the serum concentrations of HLX05 (i.e., 1-3), and ERBITUX® (i.e., 4-6) over time in cynomolgus monkeys.
Figure 17:
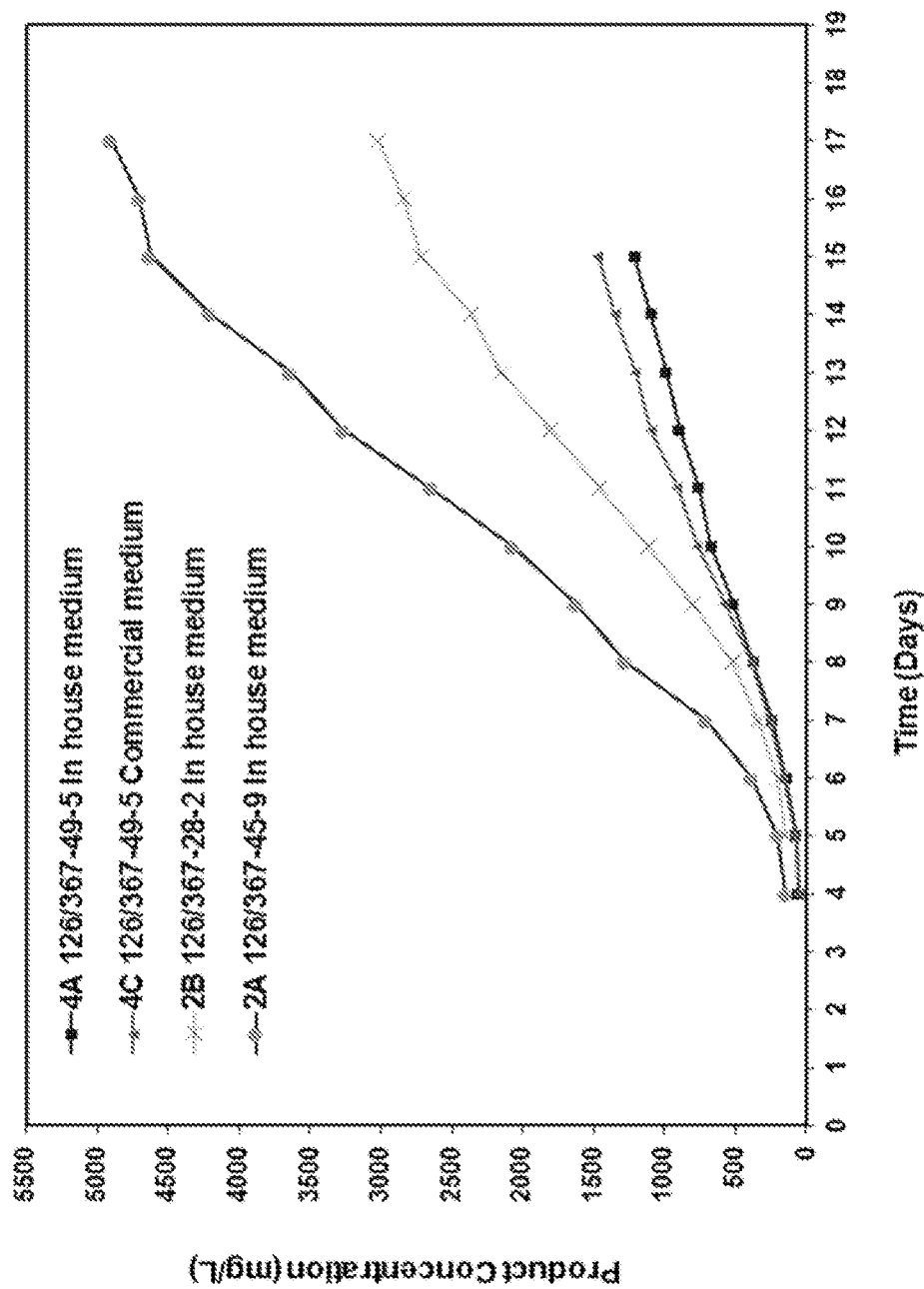
FIG. 17 shows the concentration (mg/ml) of 1-26/3-67 antibody vs. time produced by stable cell lines.

Two cynomolgus monkeys (one male and one female) were injected with antibodies (i.e., 33/34-#1, 33/34-#2, 3/67-#3, and 3/67-#4) at 24 mg/kg via i.v. Serum concentrations of the anti-EGFR antibodies were measured by ELISA method at various time point post-infusion. This experiment was repeated in a second set of cynomolgus monkeys the antibodies. As shown in the serum concentration-time profile in FIG. 16A, antibody 3/67 can be detected in the sera of cynomolgus monkeys for approximately 100 longer than antibody 34/33. FIG. 16B shows the serum concentration-time profile of HLX05 (1-3) and ERBITUX® (i.e., 4-6) in cynomolgus monkeys.

Example 6. Production of Anti-Epidermal Growth Factor Antibodies from Stable Cell Lines HLX07 1-26/3-67 top subclones were screened by plugging into an established DASGIP bioreactor platform. With a fed-batch feeding schedule, adding butyrate and a lower temperature incubation condition with pH control at 7, subclonel-26/3-67-45-9 reached 4.9 g/L by day 17. See FIG. 17.

Example 7. Stability of Anti-Epidermal Growth Factor Antibodies

Stability studies were performed in which HLX07 antibody formulations containing 5 mg/ml, 10 mg/ml, 15 mg/ml, 20 mg/ml and 25 mg/ml were subject to accelerated storage conditions (i.e., 37° C.) for up to 4 weeks. Samples were taken from each formulation at 0 weeks, 1 week, 2 week, and 4 week time points and analyzed via size exclusion chromatography (SEC) and cation exchange chromatography (CEX). SEC is widely used to detect antibody aggregates (i.e., high molecular weight species, or HMWS), monomer, and fragments (i.e., low molecular weight species, or LMWS). Cation exchange chromatography (CEX) is a well-known and widely used tool to detect protein degradation events such as deamidation or oxidation (Moorhouse et al. (1997) J. Pharm. Biomed. Anal. 16, 593-603). Degradation products are typically referred to as acidic or basic species as compared with the main species. Acidic species are variants with lower apparent pI and basic species are variants with higher apparent pI. Acidic species are the variants that elute earlier than the main peak from CEX, while basic species are the variants that elute later than the main peak from CEX. The results of SEC and CEX analyses of the samples taken from formulations stored under accelerated conditions are provided in Table 13 below:

TABLE 13

| Sample | | Stability Test at 37° C. | | | | | |
|---|---|---|---|---|---|---|---|
| | | SEC | | | CEX (%) | | |
| Concentration (mg/ml) | TimePoint | % HMWS | % Monomer | % LMWS | Acid peaks | Main peaks | Basic peaks |
| 25 | 0 weeks | 0.9 | 99.1 | 0 | 13 | 42.6 | 44.4 |
| | 1 week | 1.2 | 97.9 | 0.8 | 14.6 | 41 | 44.4 |
| | 2 weeks | 1.4 | 97.7 | 1 | 16.9 | 39.7 | 43.4 |
| | 4 weeks | 1.6 | 97.1 | 1.3 | 25 | 33.8 | 41.3 |
| 20 | 0 weeks | 0.8 | 99.2 | 0 | 13 | 42.6 | 44.4 |
| | 1 week | 1.2 | 98 | 0.8 | 14.9 | 40.6 | 44.5 |
| | 2 weeks | 1.3 | 97.7 | 1 | 17.1 | 39.8 | 43.2 |
| | 4 weeks | 1.4 | 97.2 | 1.3 | 24.9 | 34 | 41.1 |
| 15 | 0 weeks | 0.9 | 99.1 | 0 | 13 | 42.6 | 44.4 |
| | 1 week | 1.1 | 98 | 0.9 | 14.9 | 40.5 | 44.6 |
| | 2 weeks | 1.2 | 97.7 | 1.1 | 17.5 | 38.7 | 43.8 |
| | 4 weeks | 1.3 | 97.3 | 1.4 | 25.1 | 33.1 | 41.9 |
| 10 | 0 weeks | 0.9 | 99.1 | 0 | 13 | 42.6 | 44.4 |
| | 1 week | 1.1 | 98 | 1 | 16 | 39.9 | 44 |
| | 2 weeks | 1.3 | 97.6 | 1.1 | 21.6 | 38.1 | 40.4 |
| | 4 weeks | 1.6 | 96.9 | 1.5 | 27.6 | 33.2 | 39.2 |
| 5 | 0 weeks | 0.9 | 99.1 | 0 | 13 | 42.6 | 44.4 |
| | 1 week | 1 | 98 | 1 | 15.1 | 41.2 | 43.7 |
| | 2 weeks | 1.2 | 97.6 | 1.2 | 17.3 | 39.9 | 42.8 |
| | 4 weeks | 1.2 | 97.4 | 1.5 | 25.3 | 34 | 40.7 |

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

LIST OF EMBODIMENTS

Embodiments provided by the invention include, but are not limited to:
1. An anti-epidermal growth factor receptor (EGFR) antibody or antigen binding fragment thereof, comprising a heavy chain variable domain sequence comprising (1) a CDR-H1 comprising the amino acid sequence N/T/Q-YGVH (SEQ ID NO: 4); (2) a CDR-H2 comprising the amino acid sequence Y-N/A/G/D-T/D/N-P/K/E-FTSRF (SEQ ID NO: 9); and (3) a CDR-H3 comprising the amino acid sequence T/D-Y/L-YDY-E/N-FAY (SEQ ID NO: 14); and a light chain variable domain sequence comprising (1) a CDR-L1 comprising the amino acid sequence I-G/R/S-T/L/P-NIH (SEQ ID NO: 20); (2) a CDR-L2 comprising the amino acid sequence KY-A/G-SE-S/T-I-S/R (SEQ ID NO: 24); and (3) a CDR-L3 comprising the amino acid sequence NWPT-T/L/S/A/Y (SEQ ID NO: 30).
2. The anti-EGFR antibody or antigen binding fragment thereof of embodiment 1, wherein the antibody comprises a heavy chain variable domain sequence comprising (1) a CDR-H1 comprising an amino acid sequence selected from consisting of SEQ ID NOs: 1-3; (2) a CDR-H2 comprising an amino acid sequence selected from consisting of SEQ ID NOs: 5-8; and (3) a CDR-H3 comprising an amino acid sequence selected from consisting of SEQ ID NOs: 10-13; and a light chain variable domain sequence comprising (1) a CDR-L1 comprising an amino acid sequence selected from consisting of SEQ ID NOs: 15-19; (2) a CDR-L2 comprising an amino acid sequence selected from consisting of SEQ ID NOs: 21-23; (3) a CDR-L3 comprising an amino acid sequence selected from consisting of SEQ ID NOs: 25-29.
3. The anti-EGFR antibody or antigen binding fragment thereof of embodiment 2, wherein the antibody comprises a heavy chain variable domain sequence comprising (1) a CDR-H1 comprising the amino acid sequence NYGVH (SEQ ID NO: 1); (2) a CDR-H2 comprising the amino acid sequence YNTPFTSRF (SEQ ID NO: 5); and (3) a CDR-H3 comprising the amino acid sequence TYYDYEFAY (SEQ ID NO: 10); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTT (SEQ ID NO: 25).
4. The anti-EGFR antibody or antigen binding fragment thereof of embodiment 2, wherein the antibody comprises a heavy chain variable domain sequence comprising (1) a CDR-H1 comprising the amino acid sequence NYGVH (SEQ ID NO: 1); (2) a CDR-H2 comprising the amino acid sequence YNTPFTSRF (SEQ ID NO: 5); and (3) a CDR-H3 comprising the amino acid sequence DYYDYEFAY (SEQ ID NO: 11); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTS (SEQ ID NO: 27).
5. The anti-EGFR antibody or antigen binding fragment thereof of embodiment 2, wherein the antibody comprises a heavy chain variable domain sequence comprising (1) a CDR-H1 comprising the amino acid sequence NYGVH (SEQ ID NO: 1); (2) a CDR-H2 comprising the amino acid sequence YGNEFTSRF (SEQ ID NO: 8); and (3) a CDR-H3 comprising the amino acid sequence DYYDYEFAY (SEQ ID NO: 11); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTS (SEQ ID NO: 27).

6. The anti-EGFR antibody or antigen binding fragment thereof of embodiment 2, wherein the antibody comprises a heavy chain variable domain sequence comprising (1) a CDR-H1 comprising the amino acid sequence NYGVH (SEQ ID NO: 1); (2) a CDR-H2 comprising the amino acid sequence YATEFTSRF (SEQ ID NO: 7); and (3) a CDR-H3 comprising the amino acid sequence DYYDYE-FAY (SEQ ID NO: 11); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTS (SEQ ID NO: 27).

7. The anti-EGFR antibody or antigen binding fragment thereof of embodiment 2, wherein the antibody comprises a heavy chain variable domain sequence comprising (1) a CDR-H1 comprising the amino acid sequence NYGVH (SEQ ID NO: 1); (2) a CDR-H2 comprising the amino acid sequence YDDKFTSRF (SEQ ID NO: 6); and (3) a CDR-H3 comprising the amino acid sequence DYYDYE-FAY (SEQ ID NO: 11); and a light chain variable domain sequence comprising (1) a CDR-L1 comprising the amino acid sequence IGTNIH (SEQ ID NO: 15); (2) a CDR-L2 comprising the amino acid sequence KYASESIS (SEQ ID NO: 21); and (3) a CDR-L3 comprising the amino acid sequence NWPTS (SEQ ID NO: 27).

8. The anti-EGFR antibody or antigen binding fragment thereof of embodiment 2, wherein the antibody comprises a heavy chain variable domain sequence comprising (1) a CDR-H1 comprising the amino acid sequence TYGVH (SEQ ID NO: 3); (2) a CDR-H2 comprising the amino acid sequence YGNEFTSRF (SEQ ID NO: 8); and (3) a CDR-H3 comprising the amino acid sequence DYYDYE-FAY (SEQ ID NO: 11); and a light chain variable domain sequence comprising (1) a CDR-L1 comprising the amino acid sequence IRTNIH (SEQ ID NO: 16); (2) a CDR-L2 comprising the amino acid sequence KYGSESIS (SEQ ID NO: 22); and (3) a CDR-L3 comprising the amino acid sequence NWPTS (SEQ ID NO: 27).

9. The anti-EGFR antibody or antigen binding fragment thereof of embodiment 2, wherein the antibody comprises a heavy chain variable domain sequence comprising (1) a CDR-H1 comprising the amino acid sequence TYGVH (SEQ ID NO: 3); (2) a CDR-H2 comprising the amino acid sequence YGNEFTSRF (SEQ ID NO: 8); and (3) a CDR-H3 comprising the amino acid sequence DYYDYE-FAY (SEQ ID NO: 11); and a light chain variable domain sequence comprising (1) a CDR-L1 comprising the amino acid sequence ISTNIH (SEQ ID NO: 19); (2) a CDR-L2 comprising the amino acid sequence KYGSESIS (SEQ ID NO: 22); and (3) a CDR-L3 comprising the amino acid sequence NWPTS (SEQ ID NO: 27).

10. An aglycosylated CDR-H2 anti-epidermal growth factor receptor (EGFR) antibody or antigen binding fragment thereof comprising a heavy chain variable domain comprising a CDR-H2 selected comprising the amino acid sequence Y-A/G/D-D/N-K/E-FTSRF (SEQ ID NO: 31).

11. The aglycosylated CDR-H2 anti-EGFR antibody or antigen binding fragment thereof of embodiment 10, wherein the heavy chain variable domain further comprises a CDR-H1 comprising the amino acid sequence N/T/Q-YGVH (SEQ ID NO: 4) and a CDR-H3 comprising the amino acid sequence T/D-Y/L-YDY-E/N-FAY (SEQ ID NO: 14).

12. The aglycosylated CDR-H2 anti-EGFR antibody or antigen binding fragment thereof of embodiment 10 or embodiment 11, wherein the antibody or antigen binding fragment thereof further comprises a light chain variable domain sequence comprising a CDR-L1 comprising the amino acid sequence I-G/R/S-T/L/P-NIH (SEQ ID NO: 20); a CDR-L2 comprising the amino acid sequence KY-A/G-SE-S/T-I-S/R (SEQ ID NO: 24); and a CDR-L3 comprising the amino acid sequence NWPT-T/L/S/A/Y (SEQ ID NO: 30).

13. The anti-EGFR antibody or antigen binding fragment thereof according to any one of embodiments 1-12, wherein the antibody comprises an Fc sequence of a human IgG.

14. The antigen binding fragment of the anti-EGFR antibody according to any one of embodiments 1-13, wherein the antigen binding fragment is selected from the group consisting of a Fab, Fab', a F(ab)' 2, a single-chain Fv (scFv), an Fv fragment, a diabody, and a linear antibody.

15. The anti-EGFR antibody of any one of embodiments 1-13, wherein the antibody is a multispecific antibody.

16. The antibody according to any one of embodiments 1-15, wherein the antibody is an afucosylated antibody.

17. The anti-EGFR antibody or antigen binding fragment thereof according to any one of embodiments 1-16 conjugated to a therapeutic agent.

18. The anti-EGFR antibody or antigen binding fragment thereof according to any one of embodiments 1-16 conjugated to a label.

19. The antibody according to embodiment 18, wherein the label is selected from the group consisting of a radioisotope, a fluorescent dye, and an enzyme.

20. An isolated nucleic acid molecule that encodes the anti-EGFR antibody or antigen binding fragment thereof according to any one of embodiments 1-16.

21. An expression vector encoding the nucleic acid molecule of embodiment 20.

22. A cell comprising the expression vector of embodiment 21.

23. A method of producing an antibody comprising culturing the cell of embodiment 22 and recovering the antibody from the cell culture.

24. A composition comprising the anti-EGFR antibody or antigen binding fragment thereof according to any one of embodiments 1-17 and a pharmaceutically acceptable carrier.

25. A method of detecting an EGFR protein in sample from a patient by contacting the anti-EGFR antibody or antigen binding fragment thereof according to any one of embodiments 1-16 and 18-19 to the sample and detecting the anti-EGFR antibody bound to the EGFR protein.

26. The method according to embodiment 25, wherein the anti-EGFR antibody or antigen binding fragment thereof is used an immunohistochemistry assay (IHC) or in an ELISA assay.

27. A method of treating cancer in a subject, comprising administering an effective amount of the composition of embodiment 26 to the subject.

28. The method of embodiment 27, wherein the cancer is selected from throat cancer, colorectal cancer, lung cancer, and head and neck cancer.

29. The method of embodiment 27, wherein the subject is further administered a therapeutic agent selected from the group consisting of an anti-neoplastic agent, a chemotherapeutic agent, a growth inhibitory agent and a cytotoxic agent.

30. The method of embodiment 27, wherein the subject is further administered radiation therapy.

The invention claimed is:

1. An anti-epidermal growth factor receptor (EGFR) antibody comprising:
   a) a light chain variable domain comprising the amino acid sequence set forth in SEQ ID NO: 32, and a heavy chain variable domain comprising the amino acid sequence set forth in SEQ ID NO: 38;
   b) a light chain variable domain comprising the amino acid sequence set forth in SEQ ID NO: 32, and a heavy chain variable domain comprising the amino acid sequence set forth in SEQ ID NO: 37;
   c) a light chain variable domain comprising the amino acid sequence set forth in SEQ ID NO: 33, and a heavy chain variable domain comprising the amino acid sequence set forth in SEQ ID NO: 36;
   d) a light chain variable domain comprising the amino acid sequence set forth in SEQ ID NO: 34, and a heavy chain variable domain comprising the amino acid sequence set forth in SEQ ID NO: 36; or
   e) a light chain variable domain comprising the amino acid sequence set forth in SEQ ID NO: 35, and a heavy chain variable domain comprising the amino acid sequence set forth in SEQ ID NO: 39.

2. The anti-EGFR antibody of claim 1, comprising a light chain variable domain comprising the amino acid sequence set forth in SEQ ID NO: 32, and a heavy chain variable domain comprising the amino acid sequence set forth in SEQ ID NO: 38.

3. The anti-EGFR antibody of claim 1, comprising a light chain variable domain comprising the amino acid sequence set forth in SEQ ID NO: 32, and a heavy chain variable domain comprising the amino acid sequence set forth in SEQ ID NO: 37.

4. The anti-EGFR antibody of claim 1, comprising a light chain variable domain comprising the amino acid sequence set forth in SEQ ID NO: 33, and a heavy chain variable domain comprising the amino acid sequence set forth in SEQ ID NO: 36.

5. The anti-EGFR antibody of claim 1, comprising a light chain variable domain comprising the amino acid sequence set forth in SEQ ID NO: 34, and a heavy chain variable domain comprising the amino acid sequence set forth in SEQ ID NO: 36.

6. The anti-EGFR antibody of claim 1, comprising a light chain variable domain comprising the amino acid sequence set forth in SEQ ID NO: 35, and a heavy chain variable domain comprising the amino acid sequence set forth in SEQ ID NO: 39.

7. The anti-EGFR antibody of claim 1, wherein the antibody comprises a Fc sequence of a human IgG.

8. The anti-EGFR antibody of claim 1, wherein the antibody is in a form of a Fab, a Fab', a F(ab)'2, a single-chain Fv (scFv), a Fv fragment, a diabody or a linear antibody.

9. The anti-EGFR antibody of claim 1, wherein the antibody is a multispecific antibody.

10. The anti-EGFR antibody of claim 1, wherein the antibody is an afucosylated antibody.

11. The anti-EGFR antibody of claim 1, wherein the antibody is conjugated to a therapeutic agent.

12. The anti-EGFR antibody of claim 1, wherein the antibody is conjugated to a label.

13. The anti-EGFR antibody of claim 12, wherein the label is selected from the group consisting of a radioisotope, a fluorescent dye and an enzyme.

14. A composition comprising the anti-EGFR antibody of claim 1 and a pharmaceutically acceptable carrier.

* * * * *

SEQUENCE LISTING

<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asn Tyr Gly Val His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Gln Tyr Gly Val His
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Thr Tyr Gly Val His
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asn, Gln, or Thr

<400> SEQUENCE: 4

Xaa Tyr Gly Val His
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Tyr Asn Thr Pro Phe Thr Ser Arg Phe
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 6

Tyr Asp Asp Lys Phe Thr Ser Arg Phe
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Tyr Ala Thr Glu Phe Thr Ser Arg Phe
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Tyr Gly Asn Glu Phe Thr Ser Arg Phe
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Asn, Ala, Gly, or Asp
<220> FEATURE:
<221> NAME/KEY: VARIANT
<222> LOCATION: 3
<223> OTHER INFORMATION: Xaa = Thr, Asp, or Asn
<220> FEATURE:
<221> NAME/KEY: VARIANT
<222> LOCATION: 4
<223> OTHER INFORMATION: Xaa = Pro, Lys, or Glu

<400> SEQUENCE: 9

Tyr Xaa Xaa Xaa Phe Thr Ser Arg Phe
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Thr Tyr Tyr Asp Tyr Glu Phe Ala Tyr
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11
```

```
Asp Tyr Tyr Asp Tyr Glu Phe Ala Tyr
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Thr Tyr Tyr Asp Tyr Asn Phe Ala Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Thr Leu Tyr Asp Tyr Glu Phe Ala Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Thr or Asp
<220> FEATURE:
<221> NAME/KEY: VARIANT
<222> LOCATION: 2
<223> OTHER INFORMATION: Xaa = Tyr or Leu
<220> FEATURE:
<221> NAME/KEY: VARIANT
<222> LOCATION: 6
<223> OTHER INFORMATION: Xaa = Glu or Asn

<400> SEQUENCE: 14

Xaa Xaa Tyr Asp Tyr Xaa Phe Ala Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Ile Gly Thr Asn Ile His
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Ile Arg Thr Asn Ile His
1               5
```

```
<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Ile Gly Leu Asn Ile His
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Ile Gly Pro Asn Ile His
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19

Ile Ser Thr Asn Ile His
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Gly, Arg, or Ser
<220> FEATURE:
<221> NAME/KEY: VARIANT
<222> LOCATION: 3
<223> OTHER INFORMATION: Xaa = Thr, Leu, or Pro

<400> SEQUENCE: 20

Ile Xaa Xaa Asn Ile His
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Lys Tyr Ala Ser Glu Ser Ile Ser
1               5

<210> SEQ ID NO 22
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 22

Lys Tyr Gly Ser Glu Ser Ile Ser
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct

<400> SEQUENCE: 23

Lys Tyr Ala Ser Glu Thr Ile Arg
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ala or Gly
<220> FEATURE:
<221> NAME/KEY: VARIANT
<222> LOCATION: 6
<223> OTHER INFORMATION: Xaa = Ser or Thr
<220> FEATURE:
<221> NAME/KEY: VARIANT
<222> LOCATION: 8
<223> OTHER INFORMATION: Xaa = Ser or Arg

<400> SEQUENCE: 24

Lys Tyr Xaa Ser Glu Xaa Ile Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Asn Trp Pro Thr Thr
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Asn Trp Pro Thr Leu
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 27

Asn Trp Pro Thr Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct

<400> SEQUENCE: 28

Asn Trp Pro Thr Ala
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Asn Trp Pro Thr Tyr
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Thr, Leu, Ser, Ala, or Tyr

<400> SEQUENCE: 30

Asn Trp Pro Thr Xaa
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ala, Gly, or Asp
<220> FEATURE:
<221> NAME/KEY: VARIANT
<222> LOCATION: 3
<223> OTHER INFORMATION: Xaa = Asp or Asn
<220> FEATURE:
<221> NAME/KEY: VARIANT
<222> LOCATION: 4
<223> OTHER INFORMATION: Xaa = Lys or Glu

<400> SEQUENCE: 31

Tyr Xaa Xaa Xaa Phe Thr Ser Arg Phe
1               5

<210> SEQ ID NO 32
<211> LENGTH: 109
<212> TYPE: PRT
<213> ORGANISM: Artificial Sequence
```

<220> FEATURE:
<223> OTHER INFORMATION: Synthetic Construct

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Gly Gln Ala Pro Arg Leu Leu Ile
        35                  40                  45

Lys Tyr Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asn Asn Asn Trp Pro Thr
                85                  90                  95

Ser Phe Gly Gly Gly Thr Lys Val Glu Ile Lys Arg Thr
            100                 105

<210> SEQ ID NO 33
<211> LENGTH: 109
<212> TYPE: PRT
<213> ORGANISM: Artificial Sequence
<220> FEATURE:
<223> OTHER INFORMATION: Synthetic Construct

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Arg Thr Asn
            20                  25                  30

Ile His Trp Tyr Gln Gln Lys Pro Gly Gln Ala Pro Arg Leu Leu Ile
        35                  40                  45

Lys Tyr Gly Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asn Asn Asn Trp Pro Thr
                85                  90                  95

Ser Phe Gly Gly Gly Thr Lys Val Glu Ile Lys Arg Thr
            100                 105

<210> SEQ ID NO 34
<211> LENGTH: 109
<212> TYPE: PRT
<213> ORGANISM: Artificial Sequence
<220> FEATURE:
<223> OTHER INFORMATION: Synthetic Construct

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Asn
            20                  25                  30

Ile His Trp Tyr Gln Gln Lys Pro Gly Gln Ala Pro Arg Leu Leu Ile
        35                  40                  45

Lys Tyr Gly Ser Glu Ser Ile Ser Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Asn Asn Asn Trp Pro Thr
                 85                  90                  95

Ser Phe Gly Gly Gly Thr Lys Val Glu Ile Lys Arg Thr
            100                 105

<210> SEQ ID NO 35
<211> LENGTH: 108
<212> TYPE: PRT
<213> ORGANISM: Artificial Sequence
<220> FEATURE:
<223> OTHER INFORMATION: Synthetic Construct

<400> SEQUENCE: 35

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Ile Gly Thr Asn
                 20                  25                  30

Ile His Trp Tyr Gln Gln Lys Pro Gly Gln Ala Pro Arg Leu Leu Ile
             35                  40                  45

Lys Tyr Ala Ser Glu Ser Ile Ser Gly Ile Pro Ala Arg Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Asn Asn Asn Trp Pro Thr Thr
                 85                  90                  95

Phe Gly Gly Gly Thr Lys Val Glu Ile Lys Arg Thr
            100                 105

<210> SEQ ID NO 36
<211> LENGTH: 120
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ser Leu Thr Thr Tyr
                 20                  25                  30

Gly Val His Trp Val Arg Gln Ala Pro Gly Lys Gly Leu Glu Trp Leu
             35                  40                  45

Gly Val Ile Trp Ser Gly Gly Asn Thr Asp Tyr Gly Asn Glu Phe Thr
 50                  55                  60

Ser Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg Ala Leu Asp Tyr Tyr Asp Tyr Glu Phe Ala Tyr Trp Gly Gln Gly
                100                 105                 110

Thr Met Val Thr Val Ser Ser Ala
            115                 120

<210> SEQ ID NO 37
<211> LENGTH: 120
<212> TYPE: PRT
<213> ORGANISM: Artificial Sequence
```

```
<220> FEATURE:
<223> OTHER INFORMATION: Synthetic Construct

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Gly Asn Glu Phe Thr
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Asp Tyr Tyr Asp Tyr Glu Phe Ala Tyr Trp Gly Gln Gly
            100                 105                 110

Thr Met Val Thr Val Ser Ser Ala
        115                 120

<210> SEQ ID NO 38
<211> LENGTH: 120
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Ala Thr Glu Phe Thr
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Asp Tyr Tyr Asp Tyr Glu Phe Ala Tyr Trp Gly Gln Gly
            100                 105                 110

Thr Met Val Thr Val Ser Ser Ala
        115                 120

<210> SEQ ID NO 39
<211> LENGTH: 120
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30
```

-continued

```
Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
        50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Met Val Thr Val Ser Ser Ala
        115                 120
```